United States Patent
Pentelute et al.

(10) Patent No.: US 11,014,961 B2
(45) Date of Patent: May 25, 2021

(54) SELF-LABELING MINIPROTEINS AND CONJUGATES COMPRISING THEM

(71) Applicant: Massachusetts Institute of Technology, Cambridge, MA (US)

(72) Inventors: Bradley L. Pentelute, Cambridge, MA (US); Ethan Daniel Evans, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 9 days.

(21) Appl. No.: 16/480,199

(22) PCT Filed: Jan. 25, 2018

(86) PCT No.: PCT/US2018/015211
§ 371 (c)(1),
(2) Date: Jul. 23, 2019

(87) PCT Pub. No.: WO2018/140590
PCT Pub. Date: Aug. 2, 2018

(65) Prior Publication Data
US 2019/0382440 A1   Dec. 19, 2019

Related U.S. Application Data

(60) Provisional application No. 62/450,127, filed on Jan. 25, 2017.

(51) Int. Cl.
| | | |
|---|---|---|
| *C07K 1/13* | (2006.01) | |
| *C07K 1/02* | (2006.01) | |
| *C07K 1/107* | (2006.01) | |
| *C07K 14/00* | (2006.01) | |
| *C12P 21/06* | (2006.01) | |

(52) U.S. Cl.
CPC ............... *C07K 1/13* (2013.01); *C07K 1/02* (2013.01); *C07K 1/1075* (2013.01); *C07K 14/001* (2013.01); *C12P 21/06* (2013.01)

(58) Field of Classification Search
CPC .......... C07K 1/13; C07K 1/02; C07K 1/1075; C07K 14/001; C07K 14/00; C12P 21/06
See application file for complete search history.

(56) References Cited

U.S. PATENT DOCUMENTS

| 7,674,881 | B2 | 3/2010 | Kent et al. |
|---|---|---|---|
| 2013/0165389 | A1 | 6/2013 | Schellenberger et al. |
| 2014/0107043 | A1 | 4/2014 | Baleux et al. |
| 2014/0113871 | A1 | 4/2014 | Pentelute et al. |
| 2015/0266936 | A1 | 9/2015 | Cochran et al. |

OTHER PUBLICATIONS

Evans et al., "Discovery of a 29-Amino-Acid reactive Abiotic Peptide for Selective Cysteine Arylation," ACS Chem Biol, 13(3)527-532 (2017).
International Search Report and Written Opinion for International Application No. PCT/US2018/015211 dated Jun. 4, 2018.

*Primary Examiner* — Gregory S Emch
(74) *Attorney, Agent, or Firm* — Foley Hoag LLP; Dana M. Gordon; Lawrence P. Tardibono

(57) ABSTRACT

Disclosed are reactive miniproteins, and peptides comprising them. The miniproteins and peptides are amino acid sequences not found in nature that are able to undergo $S_NAr$ chemistry and other nucleophilic based reactions. Also disclosed are conjugates comprising at least one of the reactive miniproteins or peptides, and methods of forming these conjugates.

20 Claims, 26 Drawing Sheets

Specification includes a Sequence Listing.

SELF-LABELING MINIPROTEINS AND CONJUGATES COMPRISING THEM

RELATED APPLICATION

This application is a § 371 national stage application based on Patent Cooperation Treaty Application serial number PCT/US2018/015211, filed Jan. 25, 2018, which claims the benefit of priority to U.S. Provisional Patent Application Ser. No. 62/450,127, filed Jan. 25, 2017.

GOVERNMENT SUPPORT

This invention was made with Government support under Grant No. N66001-14-2-4058 awarded by the Space and Naval Warfare Systems Center, Grant No. 023504-001 awarded by the Defense Advanced Research Projects Agency. The Government has certain rights in the invention.

SEQUENCE LISTING

The instant application contains a Sequence Listing which has been submitted electronically in ASCII format and is hereby incorporated by reference in its entirety. Said ASCII copy, created on Jan. 22, 2018, is named MTV-168_25_SL.txt and is 110,494 bytes in size.

BACKGROUND

Nature has evolved over billions of years using a vast sequence space to design proteins for site-specific chemistry. For example, enzymes have high reactivity and selectivity with precise active site design. Amino acid reactivity can be modulated by tuning the $pK_a$, hydrogen bonding, alpha-helical placement, and proximal charges. However, enzymes are generally larger than 100 amino acids, and it is difficult to produce this synthetically in the lab. The ability to precisely conjugate small molecules to proteins of interest is a major field of current research.[1,2] For bioconjugation, the toolkit includes bioorthogonal methods via the use of non-natural amino acids[3-6], non-selective chemistry that stochastically labels proteogenic residues (maleimide and N-hydroxysuccinimide probes for instance), enzyme-assisted[7-9], and protein mediated approaches.[10-12] There remains a need to discover self-labeling variants for regioselective high yielding bioconjugation under mild, protein compatible conditions.

SUMMARY

Disclosed are reactive miniproteins. The miniproteins and peptides are amino acids sequences not found in nature that are able to undergo $S_NAr$ chemistry and other nucleophilic based reactions.

In one aspect, the present disclosure relates to a peptide consisting of an amino acid sequence selected from the group consisting of SEQ ID NOs: 1-158, or a peptide consisting of an amino acid sequence having at least 95% homology with a peptide selected from the group consisting of SEQ ID NOs: 1-158.

In another aspect, the disclosure relates to a conjugate comprising any one of the miniproteins or peptides disclosed herein and an antibody, a drug, a polypeptide, a protein, or a probe, or a combination thereof.

In still another aspect, the disclosure relates to a method of conjugating a peptide, wherein the peptide is any one of the miniproteins or peptides disclosed herein, to a reactive drug or a reactive probe.

In still another aspect, the disclosure relates to a method of conjugating a fusion protein, wherein the fusion protein comprises a protein and any one of the miniproteins or peptides disclosed herein and an antibody, a drug, a polypeptide, a protein, or a probe, or a combination thereof.

DETAILED DESCRIPTION

The selective modification of one side-chain functionality at one specific site in a protein is very challenging. This need for regio- and chemoselective bioconjugation reactions from only the natural 20 amino acids is of great importance especially for attachment of probes to proteins or to manufacture antibody-drug conjugates. For bioconjugation, the toolkit includes bioorthogonal methods via the use of non-natural amino acids[3-6], non-selective chemistry that stochastically labels proteogenic residues (maleimide and N-hydroxysuccinimide probes for instance), enzyme-assisted[7-9], and protein mediated approaches. Paralleling these reactions, the utility of $S_NAr$ chemistry for bioconjugation using perfluoroaromatics was demonstrated with a 4-residue peptide sequence, FCPF (SEQ ID NO: 164), capable of selectively self-labeling in the presence of other endogenous cysteines.[13] An approach leveraging mutation and conjugating additional canonical amino acid sequences to proteins is described herein. Exploring the large sequence space along with a selection procedure led to the discovery of artificial genetically encodable variants that displayed some of the profound chemistry already developed through evolution.

Large sequence diversity (>$10^9$ members) from in vitro selection techniques has been used to discover reactive biomolecules including functional RNA and peptides following the initial report of a self-alkylating ribozyme.[14] RNA sequences using various selection strategies have been found to covalently react with iodobiotin,[14] fluorescein iodoacetamide[15] in addition to genome-derived RNA capable of reacting with several electrophilic probes.[16] For peptides, a phage display experiment led to the discovery of 11-mer sequences containing a central homopropargylglycine that reacted with palladium-activated iodofluorescein.[17] Likewise, using an altered cDNA display protocol, Kawakami et al. isolated two short (13/14mer) peptides capable of self-labeling.[18]

Figure 1A:
FIG. 1A shows a random cysteine containing peptide with minimal reactivity toward the electrophile pentafluorophenyl sulfide.
Figure 1B:
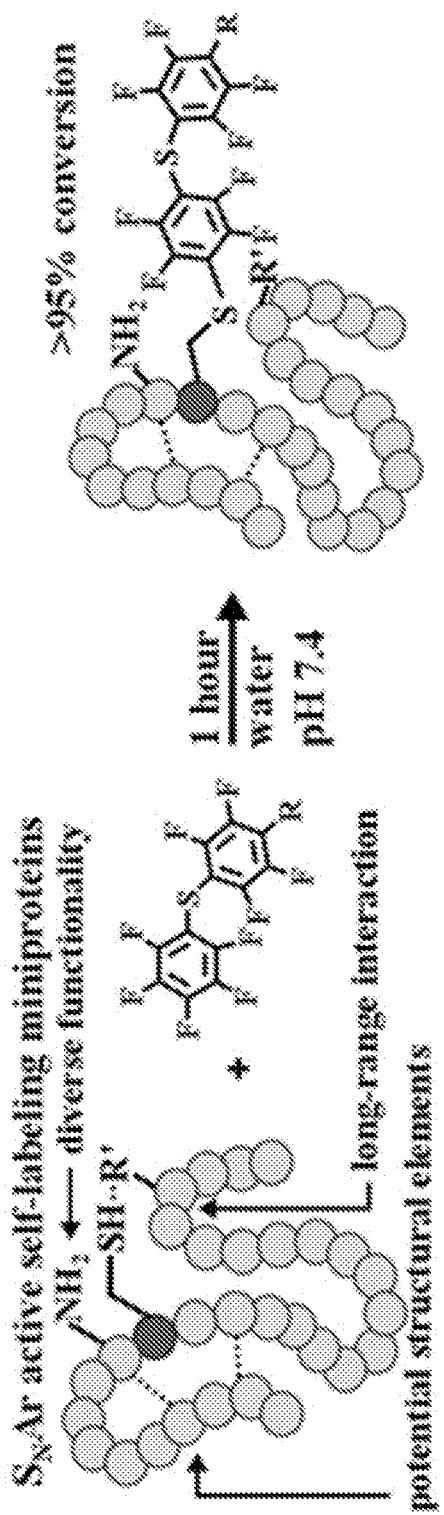
FIG. 1B shows a selected miniprotein with enhanced reactivity via several mechanisms.

Here, the focus shifted from short peptides to search the functional capabilities of larger, 30-mer miniproteins to accelerate self-labeling chemistry in mild aqueous conditions for regio- and chemoselective bioconjugation. In contrast to short peptides, using longer sequences allows for the discovery of new reactivity by alternative mechanisms of activation arising from long-range interactions, potential structural features and diverse functionality (FIGS. 1A and 1B). Possessing a defined function and suitable size—in the size range of known miniproteins (12-42 residues)[19-22]—such sequences are referred to as 'miniproteins' whether or not they possess a defined structure when put in context with the numerous examples of intrinsically disordered proteins.[23]

Enzymes can access many different mechanisms in order to facilitate rapid chemical transformations. Understanding these biopolymers requires, in part, knowledge of the reaction pathway along with a detailed description accounting for, potentially, numerous other residues in addition to solvation and ligand binding effects. Studies on enzymes have suggested a host of general reaction rate-enhancing mechanisms including: residue activation[24], reaction pathway preorganization[25], transition state stabilization[26] and reactant destabilization[27] among others. It has been proposed that such strategies rely on combinations of electrostatic interactions (proximal charges, dipole interaction and solvation)[28], steric effects[29], in addition to energies of substrate binding[27] and desolation[30] in order to achieve their rate enhancement. These mechanisms do not necessarily require a rigid active site as structural dynamics and coupled motions are often observed and suggested to play important roles[31-33]. In fact, enzymes displaying significant conformational dynamics have been reported[34] along with molten globule[35] and intrinsically disordered enzymes[36].

Compared to large enzymes, it is not obvious whether, when given the same set of monomers, small to midsized reactive peptides (≤30 amino acids, with or without substrate turnover) are capable of accessing similar activation mechanisms. Some of the smallest enzymes found naturally like lysozyme and barnase are still over 100 amino acids in length[37, 38]. Smaller still are 4-oxalocrotonate tautomerase (~62 residues, though it exists as a hexamer in solution)[39] or the 6 kDa mini-matrilysin enzyme fragment[40], yet these are still relatively large. From a purely size-based analysis, the diversity of possible structural features and substrate interaction mechanisms may be limiting. Add to this the difficulty of obtaining defined structural elements with around 30 amino acids—a size realm that often needs disulfide bonds or cyclization to impart stability[41]—and the possibility of obtaining mechanisms besides local, direct amino acid activation (tuning the pKa of a residue for example) may appear unlikely. However, the perceived difficulty peptides have of interacting with their substrate may be mitigated to an extent from studies in which short peptides have been developed to bind small molecules, a feature that may be needed for reactivity[42, 43]. Similarly, the need for structure may not be as critical in the context of conformationally dynamic enzymes.

Expanding on this, there are many examples of peptide and amino acid catalysts (though sometimes in nonaqueous conditions), providing evidence that short sequences can be successfully tuned for functions of interest[44, 45].

Knowledge of reactive peptides is perhaps less fleshed out simply due to the small number of such peptides—especially those that perform their role in water, under conditions similar to those used by nature. Research in this vein has been spurred by advancements from in vitro selection and screening protocols. These methods have provided a means to discover functional peptides not observed in nature. Many of these studies have focused on short peptides that covalently react with a target molecule and lack enzymatic turnover. Already, peptides that react with p-(chloromethyl) benzamide[18], palladium-activated iodofluorescein[17] and 2-cyanobenzothiazole[46] along with perfluoroaromatics[13] have been discovered. Much remains to be learned about such sequences undergo their respective transformations.

Figure 1C:
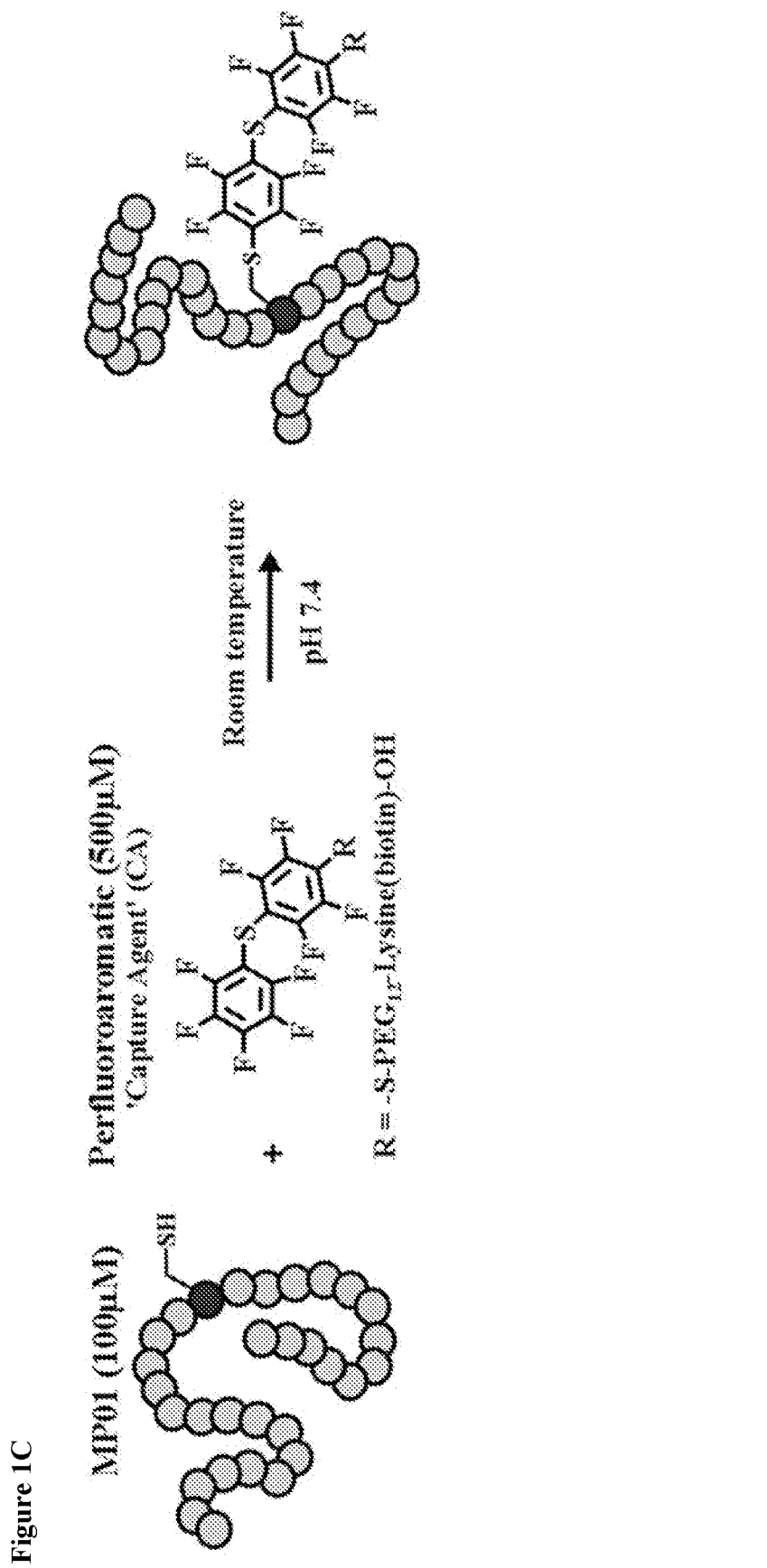
FIG. 1C shows a nucleophilic aromatic substitution reaction between an exemplary miniprotein MP01 and a perfluoroaromatic.

Here, the properties of one such midsized peptide (MP01, SEQ ID NO: 13) that is capable of reacting with a perfluoroaromatic probe (FIG. 1C) were investigated. Originally isolated from an mRNA display selection, MP01 (SEQ ID NO: 13) was shown to exhibit random coil-like secondary structure and displayed a sensitivity to severe truncation. Beyond this, the functional requirements of the sequence were not known. Its amino acid requirements and mutational tolerability along with its conformational properties and small molecule interactions were studied. An alanine scan in addition to modeling its structural landscape using Rosetta ab initio prediction[47] were performed. Combining insights from these two methods several directed point mutations were made to probe MP01's (SEQ ID NO: 13) reactivity. The modified peptides were studied using structural and biochemical means, uncovering a probe mediated secondary structure alteration with improved protease stability in the presence of the small molecule.

Miniproteins and Peptides

The miniproteins and peptides are amino acids sequences not found in nature that are able to undergo $S_NAr$ chemistry and other nucleophilic based reactions. In some embodiments of the peptides disclosed herein, the amino acid sequence uses the 20 natural amino acids.

In one aspect, the present disclosure provides a peptide consisting of an amino acid sequence selected from the group consisting of SEQ ID NOs: 1-158, or a peptide consisting of an amino acid sequence having at least 95% homology with a peptide selected from the group consisting of SEQ ID NOs: 1-158. In some embodiments, the peptide consisting of an amino acid sequence selected from Table 1.

TABLE 1

Exemplary sequences of miniproteins and peptides

| SEQ ID NO. | Sequence | Name |
|---|---|---|
| 1 | MHQKYKMTKDCFFSFLAHHKQRKLYPMSG | |
| 2 | MHQKYKMTKDCFFSFLAHRKKRKLYPMSG | |
| 3 | MHQKYKMTKDCFFPFLAHHKKRKLYPMSG | |
| 4 | MHQKYKMTKDCFFSFLAHHKMRKLYPMSG | |
| 5 | MHQKYKMTKDCFFSFLAHHKKRKLYPMSG | |
| 6 | MHQKYKVTKDCFFSFLAHHKKRKLYPMSG | |
| 7 | MHRKYKMTKDCFFSFLAHHKKRKLYPMSG | |
| 8 | MHQKYKMTKDCFFSFLAHHKKRKLYPMGG | |
| 9 | MHQKYKMTKDCFFSFLAHHKKRKSYPMSG | |
| 10 | MHQKYKMTKDCFFSSLAHHKKRKLYPMSG | |
| 11 | MHQKYKMTKDCFFSFLSHHKKRKLYPMSG | |
| 12 | MHQKYKMAKDCFFSFLAHHKKRKLYPMSG | MP01-T8A |
| 13 | MHQKYKMTKDCFFSFLAHHKKRKLYPMSG | MP01/MP01-C |
| 14 | MHRKYKMKKDCFFSFLAHHKKRKLYPMSG | |
| 15 | MHRKYEMTKDCFFSFLAHHKKRKLYPMSG | |
| 16 | MYQKYKMTKDCFFSFLAHHKKRKLYPMSG | |
| 17 | MHQKHKMTKDCFFSFLAHHKKRKLYPMSG | |
| 18 | MHQKYKMTEDCFFSFLAHHKKRKLYPMSG | |
| 19 | MHQKYKMTRDCFFSFLAHHKKRKLYPMSG | |
| 20 | MHQKYKMTKNCFFSFLAHHKKRKLYPMSG | |
| 21 | MHQKYKITKDCFFSFLAHHKKRKLYPMSG | |
| 22 | MHQKYKMTKDCFFSFLAHHKKRKLYPMNG | |
| 23 | MHQKYKMTKDCFFSFLAHHKKRKLYPTSG | |
| 24 | MHQKYKMTKDCFFSFLAYEKKRKLYPMSG | |
| 25 | MQQKYKMTKDCFFSFLAHHKKRKLYPMSG | |
| 26 | MHQKCKMTKDCFFSFLAHHKKRKLYPMSG | |
| 27 | MHQKYKMTKDCFFSFLAHHKKRRLYPMSG | |

TABLE 1 -continued

Exemplary sequences of miniproteins and peptides

| SEQ ID NO. | Sequence | Name |
|---|---|---|
| 28 | MHQKYKMTKDCFFSFLTHHKKRKLYPMSG | |
| 29 | MHQKYKMTKDCFLSFLAHHKKRKLYPMSG | |
| 30 | MHQKYKMTKDCFFSFLAHHKKRKLYPVSG | |
| 31 | MHQKYKMTKDCFSSFLAHHKKRKLYPMSG | |
| 32 | MHQKYKMTKDCFFSFLAHHKKRKLHPMSG | |
| 33 | MRQKYKMTKDCFFSFLAHHKKRKLYPMSG | |
| 34 | MHQKYKMTKDCFFSFLAHHKKGKLYPMSG | |
| 35 | MPNYGPLSPSQPSRGYTFWMVPIWDNSHNAAG | |
| 36 | MPNHGPLSPSQPSHGYTFWMVPIWDNSHNAAG | |
| 37 | MPNYGLLSPSQPSHGYTFWMVPIWDNSHNAAG | |
| 38 | MPNYGPLSPSQPSHGYTFWMVPIWDNSHSAAG | |
| 39 | MPNYGPLSPSQPSHGYTFWMVPIWDNSHNAAG | MP02 |
| 40 | MTSVTASLLMHFCPIRAHITNKPSFNPSG | MP03 |
| 41 | MTSVTASPLMHLCPIRAHITNKPSFNPSG | |
| 42 | MRTPIKFAPRLSQPFCPFRKQHQLHLHPLIEG | MP04 |
| 43 | MRTPIKFAPRLSQPFCPFRKQRQLHLHPLIEG | |
| 44 | MRPCARRDRTLWCPFDSPAWFLLSGFSCG | MP05 |
| 45 | MRPCARRGRTLWCPFDSPAWFLLSGFSCG | |
| 46 | MGIVHNATRFPKRCFYSFIATRQSMNSIRVSG | |
| 47 | MGIVHNATRFPKRCFYSFIATRQSKDSIRVSG | |
| 48 | MGIVHNATRLPKRCFYSFIATRQSKNSIRVSG | |
| 49 | MGIVHNATRFPKRCFYSFIATRQSKNSIRVSG | MP06 |
| 50 | MRTFSSDQRFSKKCYRIYFHKLRQRNRNTSVG | |
| 51 | MKTFSSDQRFSKKCYRIYFHKLRQGNHNTSVG | |
| 52 | MKTFSSDQRFSKKCYRIYFHKLRQRNHNTSVG | MP07 |
| 53 | MQHEDLCTWYGFCPSGNFTPRNLRGDSDG | MP08 |
| 54 | MRYIYVLRLKSWCGGASARSPPRSCATKLLG | |
| 55 | MRVYVLRLKSWCGGASARSSPRSCATKLLG | |
| 56 | MRYIYVLRLKSWCGGASARSSPRSCATKLLG | MP09 |
| 57 | MRYIYVLRLKSWCGGASARSPPRSCATKLLG | |
| 58 | MHSAYLRKSMRQLCYSRRTLHNIHVMSHRG | |
| 59 | MHNAYLRKSMRQLCYFRRTLHNIHVMSHRG | MP10 |
| 60 | MHQKYKMIKDCFFSFLAHAKKRKLYPMSG | |
| 61 | MHQKYKMTKDCFFSFLAHVKKRKLYPMSG | MP01-H19V |
| 62 | MHQKYKMTKDCFFSFLAHLKKRKLYPMSG | MP01-H19L |
| 63 | MHQKYKMTKDCFFAFLAHHKKRKLYPMSG | MP01-S14A |
| 64 | MHQKYKMTKACFFSFLAHHKKRKLYPMSG | MP01-D10A |
| 65 | MHQKYKMAKDCFFSFLAHHKKRKLYPMSG | |
| 66 | MHQKYKMAKACFFSFLAHHKKRKLYPMSG | MP01-T8/D10A |
| 67 | MHQKYKMAKDCFFAFLAHHKKRKLYPMSG | MP01-T8/S14A |
| 68 | MHQKYKMIKACFFAFLAHHKKRKLYPMSG | |
| 69 | MHQKYKMAKACFFAFLAHHKKRKLYPMSG | 3 Ala, MP01-T8/D10/S14A |
| 70 | MHQKYKMAKACFFAFLAHAKKRKLYPMSG | 4 Ala, MP01-T8/D10/S14/H19A |
| 71 | MHQKYKMAKACFFAFLAHLKKRKLYPMSG | MP01-T8/D10/S14A, H19L (MP01-Gen 2; 3A, 1L) |
| 72 | MHQKYKMAKACFLAFLAHLKKRKLYPMSG | |
| 73 | MHQKFKMAKACFFAFLAHLKKRKLYPMSG | |
| 74 | MHQKYKMAAACFFAFLAHLKKRKLYPMSG | |
| 75 | MHQKYKMAKACFFAFLAHLKKRKLYPVSG | |
| 76 | MHAKYKMAKACFFAFLAHLKKRKLYPMSG | |
| 77 | MHQKYKMARACFFAFLAHLKKRKLYPMSG | |
| 78 | MRQKYKMAKACFFAFLAHLKKRKLYPMSG | |
| 79 | MHQKYKMAKACFFAFLAYLKKRKLYPMSG | |
| 80 | MTHYRDNYYLQLQCTT | |
| 81 | MHQKYKMTKDCFFSFLAHHKKRKLYPMSGSGS LGHEIREIHHRL | MP01-Full |
| 82 | MPNYGPLSPSQPSHGYTFWMVPIWDNSHNAAG SGSLGHHHHHHRL | MP02-Full |
| 83 | AHQKYKMTKDCFFSFLAHHKKRKLYPMSG | MP01-M1A |
| 84 | MAQKYKMTKDCFFSFLAHHKKRKLYPMSG | MP01-H2A |
| 85 | MHAKYKMTKDCFFSFLAHHKKRKLYPMSG | MP01-Q3A |
| 86 | MHQAYKMTKDCFFSFLAHHKKRKLYPMSG | MP01-K4A |
| 87 | MHQKAKMTKDCFFSFLAHHKKRKLYPMSG | MP01-Y5A |
| 88 | MHQKYAMTKDCFFSFLAHHKKRKLYPMSG | MP01-K6A |
| 89 | MHQKYKATKDCFFSFLAHHKKRKLYPMSG | MP01-M7A |
| 90 | MHQKYKMTADCFFSFLAHHKKRKLYPMSG | MP01-K9A |
| 91 | MHQKYKMTKDSFFSFLAHHKKRKLYPMSG | MP01-C11S |
| 92 | MHQKYKMTKDCAFSFLAHHKKRKLYPMSG | MP01-F12A |
| 93 | MHQKYKMTKDCFASFLAHHKKRKLYPMSG | MP01-F13A |
| 94 | MHQKYKMTKDCFFSALAHHKKRKLYPMSG | MP01-F15A |
| 95 | MHQKYKMTKDCFFSFAAHHKKRKLYPMSG | MP01-L16A |
| 96 | MHQKYKMTKDCFFSFLAAHKKRKLYPMSG | MP01-H18A |
| 97 | MHQKYKMTKDCFFSFLAHAKKRKLYPMSG | MP01-H19A |

TABLE 1 -continued

Exemplary sequences of miniproteins and peptides

| SEQ ID NO. | Sequence | Name |
|---|---|---|
| 98 | MHQKYKMTKDCFFSFLAHHAKRKLYPMSG | MP01-K20A |
| 99 | MHQKYKMTKDCFFSFLAHHKARKLYPMSG | MP01-K21A |
| 100 | MHQKYKMTKDCFFSFLAHHKKAKLYPMSG | MP01-R22A |
| 101 | MHQKYKMTKDCFFSFLAHHKKRALYPMSG | MP01-K23A |
| 102 | MHQKYKMTKDCFFSFLAHHKKRKAYPMSG | MP01-L24A |
| 103 | MHQKYKMTKDCFFSFLAHHKKRKLAPMSG | MP01-Y25A |
| 104 | MHQKYKMTKDCFFSFLAHHKKRKLYAMSG | MP01-P26A |
| 105 | MHQKYKMTKDCFFSFLAHHKKRKLYPASG | MP01-M27A |
| 106 | MNQKYKMTKDCFFSFLAHHKKRKLYPMSG | MP01-H2N |
| 107 | MHEKYKMTKDCFFSFLAHHKKRKLYPMSG | MP01-Q3E |
| 108 | MHQKYKKTKDCFFSFLAHHKKRKLYPMSG | MP01-M7K |
| 109 | MHQKYKMTKDCFFSFLEHHKKRKLYPMSG | MP01-A17E |
| 110 | MHQKYKMTKDCFFSFLAHLKKRKLYPMSG | MP01-H19L |
| 111 | LHQKYKMTKDCFFSFLAHHKKRKLYPMSG | MP01-M1L |
| 112 | MHQKYKMTKACFFAFLAHHKKRKLYPMSG | MP01-D10/S14A |
| 113 | LHAKYKMTKDCFFSFLAHHKKRKLYPMSG | MP01-M1L, Q3A |
| 114 | LHQKYKMAKACFFAFLEHLKKRKLYPMSG | |
| 115 | LHQKYKMAKACFFAFLAHLKKRKLYPMSG | Gen 2-M1L |
| 116 | MHQKYKMAKACFFAFLEHLKKRKLYPMSG | Gen 2-A17E (MP01-Gen 3_1) |
| 117 | MHEKYKMAKACFFAFLAHLKKRKLYPMSG | Gen 2-Q3E |
| 118 | MHAKYKMAKACFFAFLAHLKKRKLYPMSG | Gen 2-Q3A |
| 119 | MHQKYKMAAACFFAFLAHLKKRKLYPMSG | Gen 2-K9A |
| 120 | MHQKYKMAKACFFAFLAHLAKRKLYPMSG | Gen 2-K20A |
| 121 | MNQKYKMAKACFFAFLAHLKKRKLYPMSG | Gen 2-H2N (MP01-Gen 3-2) |
| 122 | MHEKYKMAKACFFAFLEHLKKRKLYPMSG | Gen 3_1-Q3E |
| 123 | MHEKYKKAKACFFAFLEHLKKRKLYPMSG | Gen3_1-Q3E/M7K |
| 124 | MHQKYKMAKACFFAFLEHLKKRKLYPMS | Gen3_1 (-G) |
| 125 | MHQKYKMAKACFFAFLEHLKKRKLYPM | Gen3_1 (-SG) |
| 126 | MHQKYKMAKACFFAFLEHLKKRKLYP | Gen3_1 (-MSG) |
| 127 | MHQKYKMAKACFFAFLEHLKKRKLY | Gen3_1 (-PMSG (SEQ ID NO: 326)) |
| 128 | MHQKYKMAKACFFAFLEHLKKRKL | Gen3_1 (-YPMSG (SEQ ID NO: 327)) |
| 129 | MHQKYKMAKACFFAFLEHLKKRK | Gen3_1 (-LYPMSG (SEQ ID NO: 328)) |
| 130 | HQKYKMAKACFFAFLEHLKKRKLYPMSG | Gen3_1 (-M) |
| 131 | QKYKMAKACFFAFLEHLKKRKLYPMSG | Gen3_1 (-MR)/Gen4 (-MN) |
| 132 | KYKMAKACFFAFLEHLKKRKLYPMSG | Gen3_1 (-MHQ)/Gen4 (-MNQ) |
| 133 | MNQKYKMAKACFFAFLEHLKKRKLYPMSG | MP01-Gen 4 |
| 134 | MNQKYKMAKAAFFAFLEHLKKRKLYPMSG | Gen 4 (C11A) |
| 135 | MNQKYKMAKASFFAFLEHLKKRKLYPMSG | Gen 4 (C11S) |
| 136 | NQKYKMAKACFFAFLEHLKKRKLYPMSG | Gen4 (-M) |
| 137 | YKMAKACFFAFLEHLKKRKLYPMSG | Gen4 (-MNQK (SEQ ID NO: 329)) |
| 138 | MNQKYKMAKACFFAFLEHLKKRKLYPMS | Gen4 (-G) |
| 139 | MNQKYKMAKACFFAFLEHLKKRKLYPM | Gen4 (-SG) |
| 140 | MNQKYKMAKACFFAFLEHLKKRKLYP | Gen4 (-MSG) |
| 141 | MNQKYKMAKACFFAFLEHLKKRKLY | Gen4 (-PMSG (SEQ ID NO: 326)) |
| 142 | MNQKYKMAKACFFAFLEHLKKRKL | Gen4 (-YPMSG (SEQ ID NO: 327)) |
| 143 | MNQKYKMAKACFFAFLEHLKKRK | Gen4 (-LYPMSG (SEQ ID NO: 328)) |
| 144 | MVKLSGKERTTRNCFFSFLASRRTKKFNNLSG | MP12 |
| 145 | MGHLHICMVWRVNTSGHILSVGHKSYSSHKTG | MP13 |
| 146 | MSSGTHYGILNMVIRCHLVKNQTSQMVVLTTG | MP14 |
| 147 | MHHYCSKMKRRILMHYLFANTMAHRDLGTNG | MP15 |
| 148 | MHLRMIRYLNRRRHLCHVVEIRHGLFASREIG | MP16 |
| 149 | MNGHYPCYLITSVLVGATTSGVPVVVHLRVG | MP17 |
| 150 | MRHYHLTCFQGFRIFRRTVDSLEMEISLG | MP18 |
| 151 | MHMHKTTSYRIRVLVGVDVYRMSHTCLTSSSG | MP19 |
| 152 | MHTSLRSRAKSHSRSFGKCASIYTRYLKMG | MP20 |
| 153 | MQNSKHRPRRCLRLLPLLRGHLHRMFRERG | MP21 |
| 154 | MRSTHQRVRRPRNLCSFKHKWLIKFLKTLTG | MP22 |
| 155 | MRRTPSTRARGRVFLLPTLRFFITLCNLNG | MP24 |
| 156 | MNRIFHKRSTYQMVFGRCSDFTSTYHVLISYG | MP25 |

TABLE 1 -continued

Exemplary sequences of miniproteins and peptides

| SEQ ID NO. | Sequence | Name |
|---|---|---|
| 157 | MTATSSSTSRGCRPSTAQVVQRLRGLLLVVG | MP26 |
| 158 | MLFMRLTKKTMATKFCPFRRKRKHRERRALYG | MP27 |
| 159 | KMTKDCFFSFL | MP01-T |

In some embodiments, the peptide consists of an amino acid sequence selected from the group consisting of SEQ ID NOs: 1-33.

In some embodiments, the peptide consists of an amino acid sequence selected from the group consisting of SEQ ID NOs: 1-34.

In some embodiments, the peptide consists of an amino acid sequence selected from the group consisting of SEQ ID NOs: 34-66.

In some embodiments, the peptide consists of an amino acid sequence selected from the group consisting of SEQ ID NOs: 35-59.

In some embodiments, the peptide consists of an amino acid sequence selected from the group consisting of SEQ ID NOs: 67-98.

In some embodiments, the peptide consists of an amino acid sequence selected from the group consisting of SEQ ID NOs: 63-160.

In some embodiments, the peptide consists of an amino acid sequence selected from the group consisting of SEQ ID NOs: 12, 13, 61-64, 66, 67, 69-71, 81-113, and 115-158.

In some embodiments, the peptide consists of an amino acid sequence having at least 90% homology with a peptide selected from the group consisting of SEQ ID NOs: 1-158.

In some embodiments, the peptide consists of an amino acid sequence having at least 95% homology with a peptide selected from the group consisting of SEQ ID NOs: 1-158.

In some embodiments, the peptide consists of an amino acid sequence having at least 95% homology with a peptide selected from the group consisting of SEQ ID NOs: 1-33.

In some embodiments, the peptide consists of an amino acid sequence having at least 95% homology with a peptide selected from the group consisting of SEQ ID NOs: 1-34.

In some embodiments, the peptide consists of an amino acid sequence having at least 95% homology with a peptide selected from the group consisting of SEQ ID NOs: 34-66.

In some embodiments, the peptide consists of an amino acid sequence having at least 95% homology with a peptide selected from the group consisting of SEQ ID NOs: 35-59.

In some embodiments, the peptide consists of an amino acid sequence having at least 95% homology with a peptide selected from the group consisting of SEQ ID NOs: 67-98.

In some embodiments, the peptide consists of an amino acid sequence having at least 95% homology with a peptide selected from the group consisting of SEQ ID NOs: 60-158.

In some embodiments, the peptide consists of an amino acid sequence having at least 95% homology with a peptide selected from the group consisting of SEQ ID NOs: 12, 13, 61-64, 66, 67, 69-71, 81-113, and 115-158.

In some embodiments, the peptide consists of an amino acid sequence selected from the group consisting of SEQ ID NOs: 12, 13, 61-64, 66, 67, 69-71, 81, 82, 90, 97, 98, 104, 106-113, 115-123, 133, and 144-158.

In some embodiments of the peptides disclosed herein, the peptide consists of an amino acid sequence having at least 90%, at least 91%, at least 92%, at least 93%, at least 94%, at least 95%, at least 96%, at least 97%, at least 98%, or at least 99% with a peptide selected from the group consisting of SEQ ID NOs: 1-158, or a subset thereof. In some embodiments, the peptide consists of an amino acid sequence having at least 95%, at least 96%, at least 97%, at least 98%, or at least 99% with a peptide selected from the group consisting of SEQ ID NOs: 1-158, or a subset thereof.

In some embodiments of the peptides disclosed herein, the amino acid sequence has at least 95% homology. In some embodiments, the amino acid sequence has at least 96% homology. In some embodiments, the amino acid sequence has at least 97% homology. In some embodiments, the amino acid sequence has at least 98% homology. In some embodiments, the amino acid sequence has at least 99% homology.

In some embodiments, the homology is 95%, 96%, 97%, 98%, 99%, or 100%. In some embodiments, the homology is 100%.

In some embodiments of the peptides disclosed herein, the amino acid sequence comprises one or more cysteine residues. In some embodiments, the amino acid sequence comprises one, two, three, or four cysteine residues. In some embodiments, the amino acid sequence comprises one cysteine residue.

In some embodiments of the peptides disclosed herein, the amino acid sequence comprises a motif selected from the group consisting of FCHF (SEQ ID NO: 160), FCAF (SEQ ID NO: 161), FGPF (SEQ ID NO: 162), FCPL (SEQ ID NO: 163), FCPF (SEQ ID NO: 164), FCSF (SEQ ID NO: 165), CPFR (SEQ ID NO: 166), FCLF (SEQ ID NO: 167), LLLL (SEQ ID NO: 168), FCTF (SEQ ID NO: 169), LCPF (SEQ ID NO: 170), FRPF (SEQ ID NO: 171), FSPF (SEQ ID NO: 172), and FCRF (SEQ ID NO: 173). In some embodiments, the amino acid sequence comprises a motif selected from the group consisting of FCHF (SEQ ID NO: 160), FCAF (SEQ ID NO: 161), FGPF (SEQ ID NO: 162), FCPL (SEQ ID NO: 163), FCPF (SEQ ID NO: 164), FCPS (SEQ ID NO: 174), SFCP (SEQ ID NO: 175), FCSF (SEQ ID NO: 165), VCPF (SEQ ID NO: 176), CPFL (SEQ ID NO: 177), CPFS (SEQ ID NO: 178), CPFR (SEQ ID NO: 166), FCLF (SEQ ID NO: 167), RFCP (SEQ ID NO: 179), FCTF (SEQ ID NO: 169), LCPF (SEQ ID NO: 170), FRPF (SEQ ID NO: 171), FSPF (SEQ ID NO: 172), FCRF (SEQ ID NO: 173), and CCPF (SEQ ID NO: 180). In some embodiments, the amino acid sequence comprises a motif selected from the group consisting of FCPF (SEQ ID NO: 164), FCPI (SEQ ID NO: 181), WCPF (SEQ ID NO: 182), and FCPS (SEQ ID NO: 174). In some embodiments, the amino acid sequence comprises a FCPF motif (SEQ ID NO: 164). In some embodiments, the FCPF motif (SEQ ID NO: 164) is reactive.

In some embodiments of the peptides disclosed herein, the amino acid sequence did not converge outside of the FCPF motif (SEQ ID NO: 164).

In some embodiments, the peptide consists of an amino acid sequence having 1, 2, 3, 4, 5, or 6 point mutations compared to a peptide selected from the group consisting of SEQ ID NOs: 1-158. In some embodiments, the peptide consists of an amino acid sequence having 1, 2, or 3 point mutations compared to a peptide selected from the group consisting of SEQ ID NOs: 1-158. In some embodiments, the peptide consists of an amino acid sequence having 1 point mutation compared to a peptide selected from the group consisting of SEQ ID NOs: 1-158. In some embodiments, the peptide consists of an amino acid sequence having 2 point mutations compared to a peptide selected from the group consisting of SEQ ID NOs: 1-158. In some embodiments, the peptide consists of an amino acid sequence having 3 point mutations compared to a peptide selected from the group consisting of SEQ ID NOs: 1-158. In some embodiments, the peptide consists of an amino acid sequence having 4 point mutations compared to a peptide selected from the group consisting of SEQ ID NOs: 1-158. In some embodiments, the peptide consists of an amino acid sequence having 5 point mutations compared to a peptide selected from the group consisting of SEQ ID NOs: 1-158. In some embodiments, the peptide consists of an amino acid sequence having 6 point mutations compared to a peptide selected from the group consisting of SEQ ID NOs: 1-158.

In some embodiments, the peptide consists of an amino acid sequence having 1, 2, 3, 4, 5, or 6 point mutations compared to a peptide of SEQ ID NO: 13 (MP01). In some embodiments, the peptide consists of an amino acid sequence having 1, 2, or 3 point mutations compared to a peptide of SEQ ID NO: 13.

In some embodiments, the point mutations are one or more of M1A, M1L, H2A, H2N, Q3A, Q3E, K4A, Y5A, K6A, M7A, M7K, T8A, K9A, D10A, C11A, C11S, F12A, F13A, S14A, F15A, L16A, A17E, H18A, H19A, H19V, H19L, K20A, K21A, R22A, K23A, L24A, Y25A, P26A, and M27A. In some embodiments, the peptide consists of an amino acid sequence having one point mutation where one amino acid reside is replaced by an alanine compared to a peptide of SEQ ID NO: 13.

In some embodiments, the point mutations are one or more of M1L, H2N, Q3E, M7K, T8A, K9A, D10A, S14A, A17E, H19A, H19V, H19L, K20A, and P26A. In some embodiments, the point mutations are one or more of M1L, H2N, Q3E, M7K, T8A, D10A, S14A, A17E, and H19L. In some embodiments, the peptide consists of an amino acid sequence having one or more point mutations selected from the group consisting of T8A, D10A, S14A, and H19L. In some embodiments, the peptide consists of an amino acid sequence having one or more point mutations selected from the group consisting of T8A, D10A, S14A, and H19L compared to a peptide of SEQ ID NO: 13. In some embodiments, the peptide consists of an amino acid sequence having one or more point mutations selected from the group consisting of H2N, T8A, D10A, S14A, A17E, and H19L compared to a peptide of SEQ ID NO: 13. In some embodiments, the peptide consists of an amino acid sequence having point mutations T8A, D10A, S14A, and H19L compared to a peptide of SEQ ID NO: 13 (MP01) to give SEQ ID NO: 71 (MP01-Gen2). In some embodiments, the peptide consists of an amino acid sequence having point mutations H2N, T8A, D10A, S14A, A17E, and H19L compared to a peptide of SEQ ID NO: 13 (MP01) to give SEQ ID NO: 133 (MP01-Gen4).

In some embodiments, the peptide consists of an amino acid sequence having one or more point mutations selected from the group consisting of M1L, H2N, Q3E, and A17E. In some embodiments, the peptide consists of an amino acid sequence having one or more point mutations selected from the group consisting of M1L, H2N, Q3A, Q3E, K9A, A17E, and K20A compared to a peptide of SEQ ID NO: 71 (MP01-Gen2). In some embodiments, the peptide consists of an amino acid sequence having one or more point mutations selected from the group consisting of M1L, H2N, Q3E, and A17E compared to a peptide of SEQ ID NO: 71 (MP01-Gen2). In some embodiments, the peptide consists of an amino acid sequence having a point mutation of A17E compared to a peptide of SEQ ID NO: 71 (MP01-Gen2) to give SEQ ID NO: 116 (MP01-Gen3_1).

In some embodiments, the peptide consists of an amino acid sequence having one or more point mutations selected from the group consisting of H2N, Q3E, M7K, and A17E. In some embodiments, the peptide consists of an amino acid sequence having one or more point mutations selected from the group consisting of H2N, Q3E, and M7K compared to a peptide of SEQ ID NO: 71 (MP01-Gen2). In some embodiments, the peptide consists of an amino acid sequence having a point mutation of H2N compared to a peptide of SEQ ID NO: 71 (MP01-Gen2) to give SEQ ID NO: 121 (MP01-Gen3_2).

In some embodiments, the peptide consists of an amino acid sequence having one or more truncations compared to a peptide selected from the group consisting of SEQ ID NOs: 1-158. In some embodiments, the truncations are N-terminal truncations. In some embodiments, the N-terminal truncations are selected from the group consisting of deletion of 1, 2, 3, and 4 amino acid residues from the N-terminus. In some embodiments, the truncations are C-terminal truncations. In some embodiments, the C-terminal truncations are selected from the group consisting of deletion of 1, 2, 3, 4, 5, or 6 amino acid residues from the C-terminus. In some embodiments, the peptide consists of an amino acid sequence having one or more truncations compared to a peptide of SEQ ID NO: 116 (MP01-Gen3_1). In some embodiments, the peptide consists of an amino acid sequence selected from the group consisting of SEQ ID NOs: 124-132. In some embodiments, the peptide consists of an amino acid sequence having one or more truncations compared to a peptide of SEQ ID NO: 133 (MP01-Gen4). In some embodiments, the peptide consists of an amino acid sequence selected from the group consisting of SEQ ID NOs: 136-143. In some embodiments, the peptide consists of an amino acid sequence selected from the group consisting of SEQ ID NOs: 124-132 and 136-143.

In some embodiments of the peptides disclosed herein, the peptide forms an alpha helix.

In some embodiments of the peptides disclosed herein, the cysteine is at the N-terminus of the alpha helix.

Conjugates Comprising a Miniprotein or Peptide

Most existing self labeling technologies rely on either unnatural amino acids or large proteins that must be added onto the protein one wishes to study or label. Unnatural amino acids can be difficult to incorporate into select proteins. The methods and miniproteins disclosed herein can overcome this challenge. In some embodiments of the methods and peptides disclosed herein, the amino acid sequence uses the 20 natural amino acids. Other self-labeling strategies that rely on large proteins (Halo tag, CLIP tag etc.) are large (>100 amino acid) proteins. Attaching large proteins to the protein of interest can disrupt the function and folding (and potentially trafficking) of the protein of interest and thus the methods and miniproteins disclosed herein are alternatives to overcome these issues.

The miniproteins and peptides are amino acids sequences that are able to undergo nucleophilic based reactions. In some embodiments, the nucleophilic based reaction is $S_NAr$ chemistry.

The miniproteins and peptides are amino acids sequences not found in nature which are capable of reacting with electrophilic probes to covalently label themselves. The application of these peptides is to selectively label themselves with a small molecule in the presence of other reactive amino acids. When attached to other biomolecules of interest, the miniproteins can be used for site specific labeling.

In some embodiments of the miniproteins and peptides disclosed herein, the miniprotein or peptide reacts with an electrophilic probe at a rate greater than 0 $M^{-1}$ $s^{-1}$. In some embodiments, the reaction rate ranges from about 0.01 $M^{-1}$ $s^{-1}$ to about 250 $M^{-1}$ $s^{-1}$. In some embodiments, the reaction rate ranges from about 0.01 $M^{-1}$ $s^{-1}$ to about 50 $M^{-1}$ $s^{-1}$. In some embodiments, the reaction rate ranges from about 0.2 $M^{-1}$ $s^{-1}$ to about 35 $M^{-1}$ $s^{-1}$. In some embodiments, the reaction rate ranges from about 0.01 $M^{-1}$ $s^{-1}$ to about 30 $M^{-1}$ $s^{-1}$. In some embodiments, the reaction rate ranges from about 0.29 $M^{-1}$ $s^{-1}$ to about 29.7 $M^{-1}$ $s^{-1}$. In some embodiments, the reaction rate ranges from about 0.04 $M^{-1}$ $s^{-1}$ to about 1.8 $M^{-1}$ $s^{-1}$.

In some embodiments of the miniproteins and peptides disclosed herein, the peptide with a larger reaction rate constant is selected for further optimization.

In some embodiments, antibody-drug conjugates (or any general protein-drug conjugate as the miniproteins can be genetically, or chemically attached to any protein of interest) may be used for designing a therapeutic and experimental tool, protein-fluorophore conjugates for studying in vivo/in cellulo expression, localization and other properties of the protein of interest.

In another aspect, the disclosure relates to a conjugate comprising any one of the miniproteins or peptides disclosed herein and an antibody, a drug, a polypeptide, a protein, or a probe, or a combination thereof. In some embodiments, the conjugation reaction occurs under mild, protein compatible conditions. In some embodiments, the conjugation reaction further comprised a reducing agent, such as 1,4-dithio-DL-threitol (DTT) or tris(2-carboxyethyl)phosphine (TCEP).

In some embodiments, the conjugate comprises a peptide and a drug. In some embodiments, the drug is selected from the group consisting of amanitin, anthramycin, auristatin E, auristatin F, calicheamicin, camptothecin, CC-1065 (and related duocarmycins), dolastatin 10, doxorubicin, duocarmycin A, maytansine (and derivatives including DM1 and DM4), monomethylauristatin E, monomethylauristatin F, N-acetyl-γ-calicheamicin dimethyl hydrazide, pyrrolobenzodiazepine (PBD) dimer, SG2000 (SJG-136), SG2202, SN-38 (and prodrug irinotecan), and TZT-1027 In some embodiments, the conjugate comprises a peptide and a polypeptide.

In some embodiments, the conjugate comprises a peptide and a protein. In some embodiments, the peptide is attached to the protein at the C-terminus or at the N-terminus. In some embodiments, the peptide is attached to the protein at the N-terminus.

In some embodiments, the protein is selected from the group consisting of sortase A, c-Myc, glutathione S-transferase (GST), hemagglutinin (HA), and maltose-binding protein. In some embodiments, the protein is sortase A.

In some embodiments, a cleavable motif is inserted between the miniproteins or peptides disclosed herein and a protein. In some embodiments the cleavable motif is a tobacco etch virus motif.

In some embodiments, the protein is an antibody. In some embodiments, the antibody is selected from the group consisting of protein A, protein G, protein A/G, and protein L. In some embodiments, the antibody targets a protein selected from the group consisting of CD19, CD20, CD22, CD30, CD33, CD44, CD49, CD79, CEACAM-5, epidermal growth factor receptor (EGFR), human epidermal growth factor receptor II (HER2), glycoprotein nonmetastatic melanoma protein B (gpNMB), and TROP-2.

In some embodiments, the conjugate comprises any one of the miniproteins or peptides disclosed herein, an antibody, and a drug. In some embodiments, the antibody and the drug form an antibody-drug conjugate (ADC). In some embodiments, the antibody-drug conjugate is selected from the group consisting of ado-trastuzumab emtansine (containing DM1 and targeting human epidermal growth factor receptor II), BR96-doxorubicin, brentuximab vedotin (containing MMAE and targeting CD30), gemtuzumab ozogamicin (containing calicheamicin and targeting CD33), glembatumumab vedotin (containing MMAE and targeting gpNMB), inotuzamab ozogamicin (containing calicheamicin and targeting CD22), γ-calicheamicin ADC, CL2A-SN-38 ADC, MC-MMAF ADC (e.g., containing MMAF and targeting HER2), MCC-DM1 ADC (e.g., containing DM1 and targeting CD20, protein G, or HER2), SPDB-DM4 ADC (containing DM1 and targeting CD19), VA-pyrrolobenzodiazepine ADC (containing pyrrolobenzodiazepine and targeting CD33), VC-Duo ADC (SYD985 containing duocarmycin targeting HER2), and VC-MMAE ADC (e.g., containing MMAE and targeting MSLN).

In some embodiments, the conjugate comprises a peptide, and a probe.

In some embodiments, the conjugate comprises a peptide, a protein, and a probe.

In some embodiments of the conjugates disclosed herein, the probe is a capture agent. In some embodiments, the capture agent comprises a moiety selected from the group consisting of biotin, avidin, streptavidin, and histidine-tag. In some embodiments, the capture agent comprises a biotin moiety. In some embodiments, the capture agent comprises a In some embodiments, the capture agent comprises a biotin moiety, a polyethylene glycol (PEG), and a pentafluorophenyl sulfide. In some embodiments, the capture agent comprises a polyethylene glycol (PEG) and a pentafluorophenyl sulfide. In some embodiments, the capture agent comprises a biotin moiety, an amino acid residue (e.g., lysine), a polyethylene glycol (PEG), and a pentafluorophenyl sulfide.

In some embodiments of the conjugates disclosed herein, the probe is a fluorophore. In some embodiments, the fluorophore comprises a moiety selected from the group consisting of ALEXA FLUOR® 350, ALEXA FLUOR® 405, ALEXA FLUOR® 430, ALEXA FLUOR® 488, ALEXA FLUOR® 514, ALEXA FLUOR® 532, ALEXA FLUOR® 546, ALEXA FLUOR® 555, ALEXA FLUOR® 568, ALEXA FLUOR® 594, ALEXA FLUOR® 610, ALEXA FLUOR® 633, ALEXA FLUOR® 635, ALEXA FLUOR® 647, ALEXA FLUOR® 660, ALEXA FLUOR® 680, ALEXA FLUOR® 700, ALEXA FLUOR® 750, ALEXA FLUOR® 790, AMCA, bimane, BODIPY, BODIPY 530/550, BODIPY 558/568, BODIPY 564/570, BODIPY 576/589, BODIPY 581/591, BODIPY 630/650, BODIPY 650/665, BODIPY FL, BODIPY R6G, BODIPY TMR, BODIPY TR, cascade blue dye, cascade yellow dye, dansyl, dapoxyl dye, dialkylaminocoumarin, 2',7'-dichloro-fluorescein, 4',5'-dichloro-2',7'-dimethoxy-fluorescein (JOE), eosin, fluorescein, hydroxycoumarin, lissamine rhodamine B, malachite green, marina blue dye, methoxycoumarin, naphthofluorescein, NBD, Oregon green 488, Oregon green 514, pacific blue dye, pacific orange dye, pyMPO, pyrene, QSY 7, QSY 9, QSY 35, QSY 21, rhodamine 6G, rhodamine green dye, rhodamine red dye, Texas red dye, tetramethyl-rhodamine (TMR), and X-rhodamine.

In some embodiments of the conjugates disclosed herein, the probe is a dye. In some embodiments, the dye comprises Coomassie blue.

In some embodiments of the conjugates disclosed herein, the probe is covalently bound to a cysteine residue. In some embodiments of the conjugates disclosed herein, the probe is covalently bound to a cysteine residue in the presence of other endogenous cysteine residues.

Methods of Conjugating a Peptide or a Fusion Protein

In yet another aspect, the present disclosure provides a method of conjugating any one of the miniproteins or peptides disclosed herein and an antibody, a drug, a polypeptide, a protein, or a probe.

In some embodiments, provided herein is a method of conjugating a peptide, comprising:

providing an aqueous solution comprising a peptide consisting of an amino acid sequence selected from the group consisting of SEQ ID NOs: 1-158, or a peptide consisting of an amino acid sequence having at least 95% homology with a peptide selected from the group consisting of SEQ ID NOs: 1-158;

adding to the solution a reactive drug or a reactive probe;

thereby covalently binding the drug or the probe to the peptide at one amino acid residue to produce a conjugated peptide.

In some embodiments, the present disclosure provides a method of conjugating a fusion protein, comprising:

providing an aqueous solution comprising a fusion protein, wherein the fusion protein comprises a protein and a peptide consisting of an amino acid sequence selected from the group consisting of SEQ ID NOs: 1-158, or a protein and a peptide consisting of an amino acid sequence having at least 95% homology with a peptide selected from the group consisting of SEQ ID NOs: 1-158;

adding to the solution a reactive drug or a reactive probe;

thereby covalently binding the drug or the probe to the fusion protein at one amino acid residue to produce a conjugated fusion protein.

In some embodiments of the methods disclosed herein, the conjugates are as described above.

Definitions

Unless otherwise defined herein, scientific and technical terms used in this application shall have the meanings that are commonly understood by those of ordinary skill in the art. Generally, nomenclature used in connection with, and techniques of, chemistry described herein, are those well-known and commonly used in the art.

For convenience, certain terms employed in the specification, examples, and are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

EXAMPLES

The invention now being generally described, it will be more readily understood by reference to the following examples, which are included merely for purposes of illustration of certain aspects and embodiments of the present invention, and are not intended to limit the invention.

Example 1: General Procedures

Chemicals and Enzymes

Pentafluorophenyl sulfide was purchased from Santa Cruz Biotechnology (Dallas, Tex.). 1,4-Dithio-DL-threitol (DTT), 1-[Bis(dimethylamino)methylene]-1H-1,2,3-triazolo[4,5-b]pyridinium 3-oxid hexafluorophosphate (HATU), Fmoc-L-Ala-OH, Fmoc-L-Cys(trt)-OH, Fmoc-L-Asp(tBu)-OH, Fmoc-L-Glu(tBu)-OH, Fmoc-L-Phe-OH, Fmoc-Gly-OH, Fmoc-L-His(Boc)-OH, Fmoc-L-Ile-OH, Fmoc-L-Lys(Boc)-OH, Fmoc-L-Leu-OH, Fmoc-L-Met-OH, Fmoc-L-Asn(Trt)-OH, Fmoc-L-Pro-OH, Fmoc-L-Gln (Trt)-OH, Fmoc-L-Arg(Pbf)-OH, Fmoc-L-Ser(tBu)-OH, Fmoc-L-Thr(tBu)-OH, Fmoc-L-Val-OH, Fmoc-L-Trp(Boc)-OH, Fmoc-L-Tyr(tBu)-OH, Fmoc-L-Lys(biotin)-OH, 2-chlorotrityl chloride resin were purchased from Chem-Impex International (Wood Dale, Ill.). H-rink-amide CHEMMATRIX® Hyr resin was obtained from PCAS BioMatrix, Inc (Quebec, Canada). (7-Azabenzotriazol-1-yloxy)tripyrrolidinophosphonium hexafluorophosphate (PyAOP) was purchased from P3 BioSystems (Lousiville, Ky.). Tris(2-carboxyethyl)phosphine hydrochloride was purchased from Hampton Research (Aliso Viejo, Calif.). Carboxy-PEG12-thiol was purchased from Thermo Fisher Scientific. SuperScript II reverse transcriptase and RNase OUT were purchased from Invitrogen (Carlsbad, Calif.), while Taq polymerase and T7 RNA polymerase (and their associated buffers) were obtained from New England Biolabs (Ipswich, Mass.). Flexi rabbit reticulocyte lysate along with rNTPs and dNTPs were purchased from Promega (Madison, Wis.). Biotechnology grade proteinase K was obtained from Amresco. N, N-dimethylformamide (DMF), acetonitrile (ACN), diethyl ether were purchased from VWR (Radnor, Pa.). Trifluoroacetic acid (TFA) was obtained from Sigma-Aldrich. Other chemicals listed were purchased from either Sigma-Aldrich or VWR and used as received.

Liquid Chromatography-Mass Spectrometry (LC-MS)

Solvent A refers to water with 0.1% (v/v) TFA, while B refers to acetonitrile with 0.1% (v/v) TFA. Solvent C refers to water with 0.1% (v/v) FA, and solvent D refers to acetonitrile with 0.1% (v/v) FA. TIC refers to total ion current in the LC-MS chromatogram. LC-MS chromatograms and mass spectra were obtained using either an Agilent 6520 ESI-Q-TOF mass spectrometer or an Agilent 6550 iFunnel Q-TOF mass spectrometer (MS/MS analysis was conducted on an Agilent 6550 iFunnel Q-TOF mass spectrometer). Software used for LCMS analysis and integration was the Agilent MassHunter package, and deconvolution was performed using maximum entropy.

Method 1 (Agilent 6520 ESI-Q-TOF mass spectrometer):
LC method: 0-2 minutes 5% B, 2-11 minutes 5-65% B linear ramp, 11-12 minutes 65% B, 0.8 mL/min flow rate.
Column: Zorbax 300SB C3 column (2.1×150 mm, 5 μm), 40° C.
MS parameters: positive electrospray ionization (ESI).

Method 2:
LC method: 0-3 minutes 5% B, 3-17 minutes 5-95% B linear ramp, 17-18 minutes 95% B, 0.8 mL/min flow rate.
Column: Zorbax 300SB C18 column (2.1×150 mm, 5 μm), 40° C.
MS parameters: positive ESI Method 3:
LC method: 0-3 minutes 5% B, 3-15 minutes 5-80% B linear ramp, 15-16 minutes 80% B, 0.8 mL/min flow rate.
Column: Zorbax 300SB C18 column (2.1×150 mm, 5 μm), 40° C.
MS parameters: positive ESI, MS off at 11 minutes Method 4 (Agilent 6520 ESI-Q-TOF mass spectrometer):
LC method: 0-2 minutes 95% C and 5% D, 2-11 minutes 5-65% D linear ramp, 11-12 minutes 65% B, 0.8 mL/min flow rate.
Column: Zorbax 300SB C3 column (2.1×150 mm, 5 μm), 40° C.
MS parameters: positive electrospray ionization (ESI).

Figure 2A:
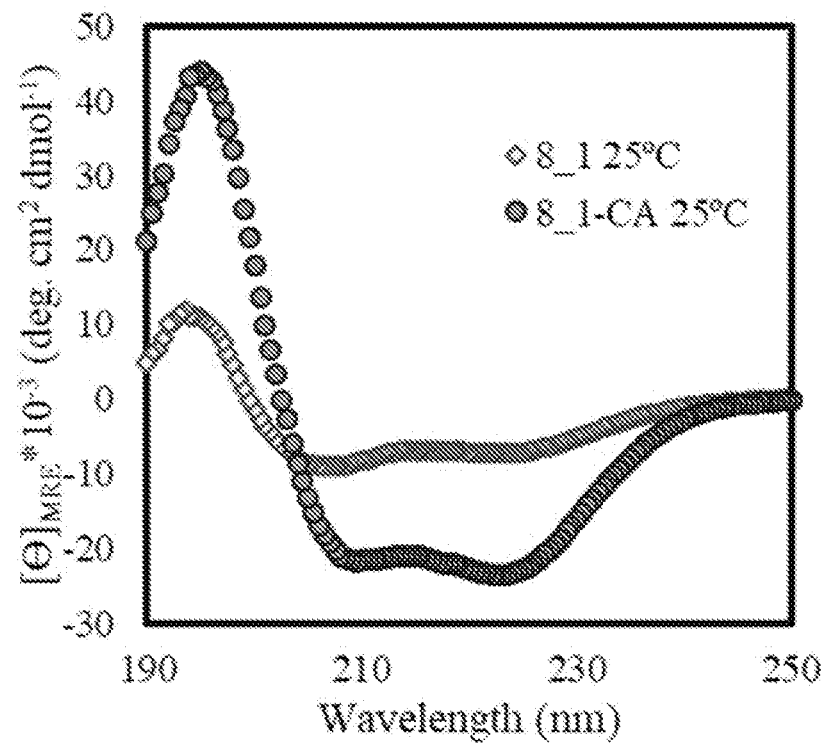
FIG. 2A shows CD spectra of an exemplary miniprotein (Gen4 variant, 8_1) and the CA labeled Gen4 (8_1-CA) at room temperature.
Figure 2B:
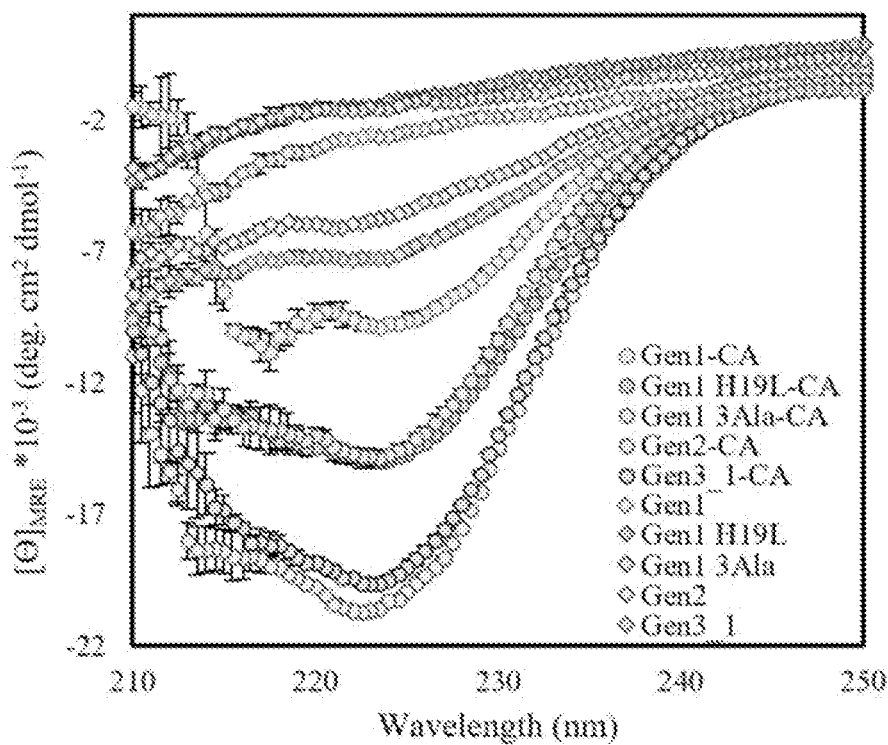
FIG. 2B shows CD spectra of exemplary miniproteins.

Method 5 (Agilent 6550 iFunnel Q-TOF mass spectrometer):
LC method: 0-4 minutes 99% C and 5% D, 4-17.5 minutes 1-61% D linear ramp, 17.5-18 minutes 61% D, 0.4 mL/min flow rate.
Column: Poroshell 300SB-$C_3$ column (1×75 mm, 5 μm), 40° C.
MS parameters: positive ESI, MS off at 10 minutes Circular Dichroism Room temperature circular dichroism (CD) spectroscopy of the unlabeled Gen4 (8_1, SEQ ID NO: 133) showed a mix of random coil and alpha helix (FIG. 2A). The CA labeled version displayed a significantly increased alpha helical signature. To determine whether this structural alteration was unique to Gen4 (SEQ ID NO: 133) or had emerged from the selection used to obtain Gen1 (MP01, SEQ ID NO: 13), CD measurements were conducted on select previous generations. All versions analyzed displayed enhanced alpha helicity upon reaction with the CA relative to their unlabeled forms (FIG. 2B). Nuclear magnetic resonance (NMR) characterization of Gen4 (SEQ ID NO: 133) revealed concentration and temperature-dependent structural elements. At lower concentrations and temperatures, the amide proton region displayed increased signal intensities. Along with this, Gen4 (SEQ ID NO: 133) possesses several aromatic-to-aliphatic NOE cross peaks, indicative of side chain interactions. A structure could not be obtained due to apparent aggregation at high concentrations for both Gen4 (SEQ ID NO: 133) and its CA labeled version.

All experiments were performed at room temperature (~23.5° C.) using a Jasco J-1500 spectrometer at MIT's Biophysical Instrumentation Facility (BIF). General conditions used were 10 mM sodium phosphate buffer at pH 7.45 with 5 mM TCEP (if a cysteine was present) with 50 μM peptide. CD measurements with C11S and C11A versions of Gen4 (SEQ ID NOs: 138 and 137, respectively) used the same conditions, without TCEP but with varying amount of CA (50 μM up to 500 μM depending on the desired mole ratio). Temperature melt data was obtained using a 0.5° C./minute ramp with data collected at 222 nm. For the various constructs these data were then normalized between 0 and 1 and plotted. For CD of Gen 1 (MP01; SEQ ID NO: 13), Gen1 H19L (MP01-H19L; SEQ ID NO: 62), Gen1 3 ala (MP01-T8/D10/S14A; SEQ ID NO: 69), Gen2 (MP01-Gen2; SEQ ID NO: 71) and Gen3_1 (MP01-Gen3_1; Gen 2-A17E; SEQ ID NO: 116) in their labeled and nonlabeled states, data was obtained in 12.5 mM HEPES, 50 mM NaCl, 2.5 mM $MgCl_2$ and 2.5 mM $CaCl_2$ at pH 7.45 with 5 mM TCEP at 50 M peptide with or without ~55 μM CA that had reacted for ~2 days at room temperature. The CA labeled versions were not purified post reaction and were analyze in their reaction mixture.

Protease Digestions

Figure 3A:
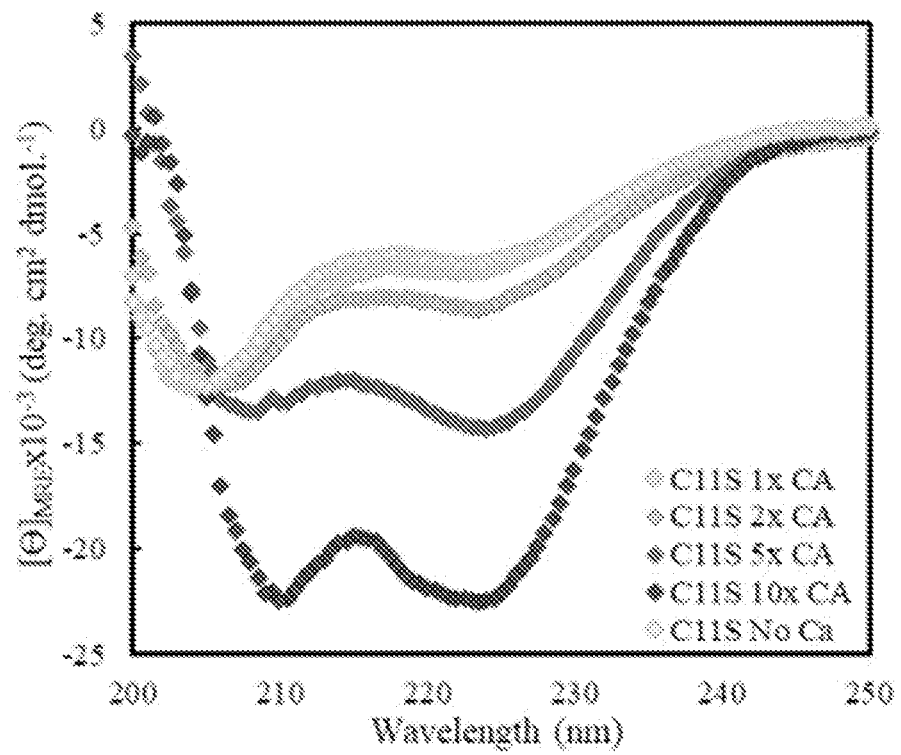
FIG. 3A shows CD analysis of an exemplary miniprotein (Gen4(C11S) with the CA at varying concentrations.
Figure 3B:
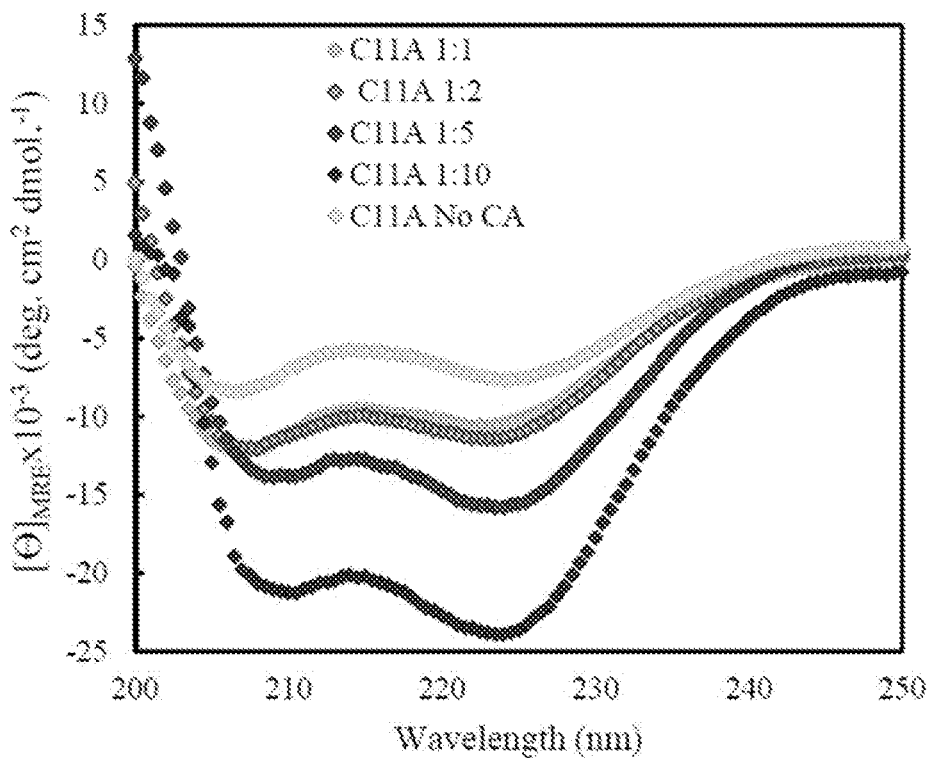
FIG. 3B shows CD analysis of an exemplary miniprotein (Gen4(C11A) with the CA at varying concentrations.
Figure 3C:
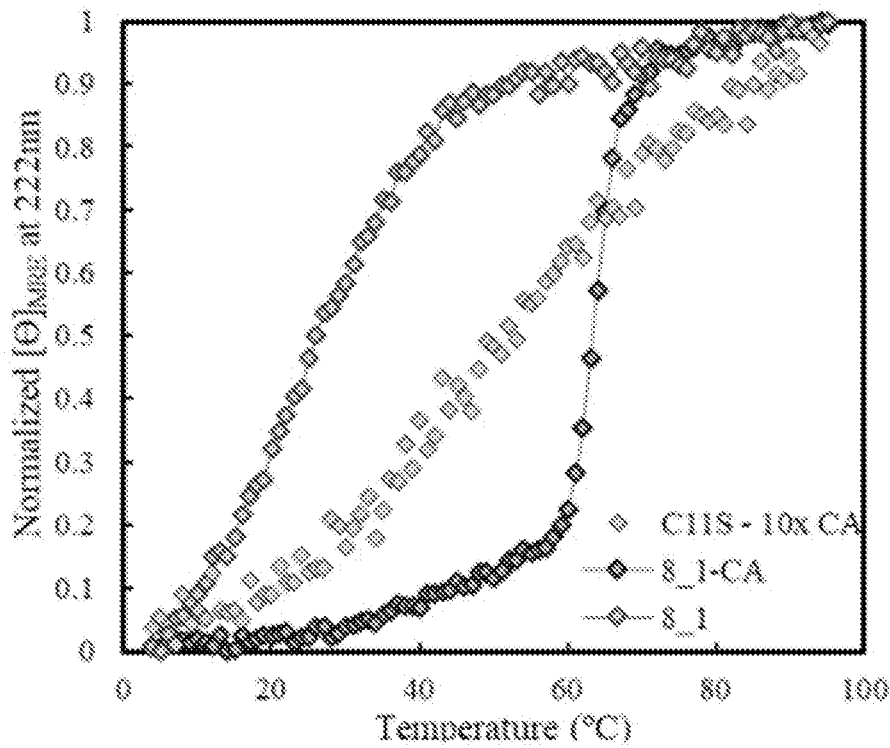
FIG. 3C shows thermal melting for an exemplary miniprotein without Cys with 10×CA (C11A-10×CA) compared to an exemplary miniprotein with Cys (Gen4, 8_1) and a CA labeled exemplary miniprotein with Cys (Gen4-CA, 8_1-CA).
Figure 3D:
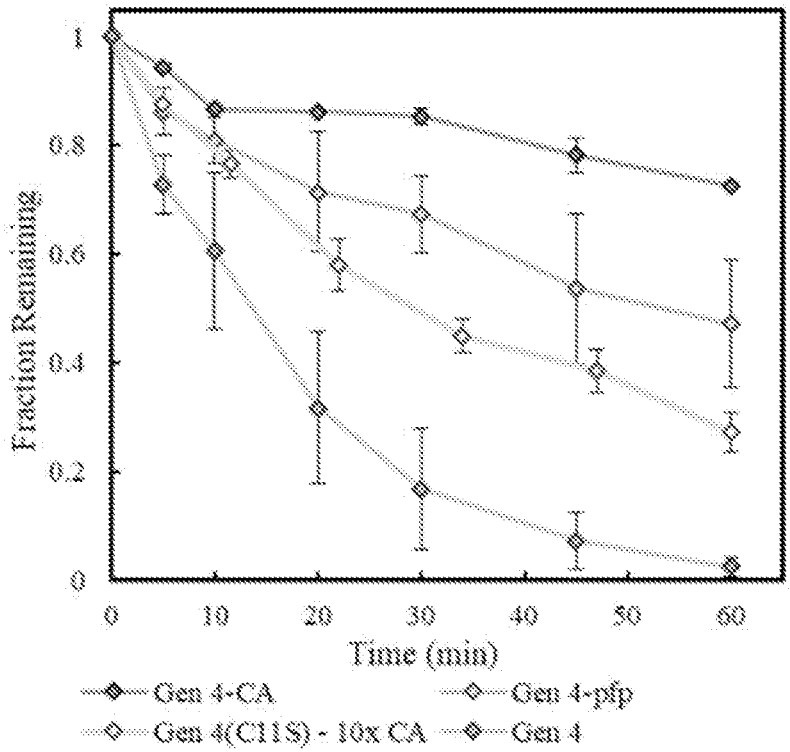
FIG. 3D shows protease stability of to an exemplary miniprotein with Cys (Gen4), a CA labeled exemplary miniprotein with Cys (Gen4-CA), an exemplary miniprotein without Cys with 10×CA (Gen4(C11S) with 10×CA), and an exemplary miniprotein with Cys bound to only the perfluoroaromatic portion of the CA (Gen4-pfp).

MP01-Gen4 (SEQ ID NO: 133) showed CA-mediated structural alterations and increased protease stability even when rendered nonreactive. Lacking an apparent cysteine $pK_a$ modulation, the basis for Gen4's high reactivity again came into question. Both C11A (SEQ ID NO: 134) and C11S (SEQ ID NO: 135) variants were synthesized and assayed them for CA-mediated structural alteration via CD. Both displayed CA concentration-dependent secondary structural alterations, approaching the secondary structure displayed by the covalently labeled Gen4-CA construct (FIGS. 3A-3C). Thermal melting of labeled and unlabeled Gen4 peptides (C11 present, followed from 4-95° C. at 222 nm via CD) displayed a sharp unfolding transition for the CA-labeled version near 64° C. whereas the unlabeled version displayed a broad, gradually increasing trend (FIG. 3C). Noncovalently interacting Gen4(C11S) (SEQ ID NO: 135) at 50 µM with 10×CA (500 µM) likewise showed a gradually increasing CD signal albeit with a shift to higher temperatures than that seen in Gen4 (SEQ ID NO: 133) alone (FIG. 3C). Compounding on the altered structure, the CA labeled Gen4 displayed significantly increased protease resistance relative to the unlabeled Gen4 (FIG. 3D). In line with the results from CD, Gen4(C11A and S) (with 10×CA) displayed an improved protease stability relative to Gen4 (SEQ ID NO: 133) alone but was not as stable as the covalently bound form (FIG. 3D). To probe the role of the CA in protease stability a pentafluorophenyl sulfide (pfp) labeled Gen4 was synthesized, lacking the bulky PEG-lysine-biotin of the CA. This variant displayed relatively high stability but was slightly diminished when compared to the full CA version.

Reactions were performed using 100 µM peptide with 0.5 g/mL of proteinase K for general cleavage with the addition of 1 mM CA for C11A and C11S digestions. Reactions were quenched with 49.75% water, 49.75% ACN and 0.5% TFA at selection time point and analyzed by LCMS. TIC-based integrated peak areas were used to determine the amount of material in a given time point normalized to the starting amount. These normalized values there then concerted to fraction remaining and plotted as shown.

NMR Analysis

Experiments were conducted with variable concentrations of MP01-Gen4 (SEQ ID NO: 133) in 10 mM phosphate pH 7.0. Non CA labeled peptide was reduced with 1 mM d-TCEP. NMR data were collected on Bruker Avance III 750 and 500 spectrometers with cryogenic probes.

Example 2: Miniprotein and Peptide Synthesis, Cleavage, and Purification

Peptides and miniproteins were synthesized using an automated flow peptide synthesizer built in house on a 0.09 mmol scale using Fmoc-SPPS chemistry on H-rink amide CHEMMATRIX® Hyr resin. General synthesis was performed at 90° C. using the following protocol with a 80 mL/min flow rate: 15 s amino acid coupling (0.14 µM HATU, 0.2 µM amino acid, 10% (v/v) N,N-diisopropylethylamine (DIEA), 4.8 mL total), 38 s 12 mL DMF wash, 34 s 11.2 mL 20% piperidine (v/v) in DMF, and deprotection with a final 38 s 12.8 mL DMF wash. Deviations from this protocol included: Arg and Phe couplings that were completed using PyAOP as the activating agent instead of HATU and the HHHHHHRL (SEQ ID NO: 183) sequence found on MP01-full and MP02-full that was synthesized using a 40 mL/min coupling at 70° C. with all other parameters the same. Following synthesis, miniproteins and peptides were cleaved from the resin and side-chain deprotected using a mixture of 94% TFA, 2.5% (v/v) 1,2-ethanedithiol (EDT), 2.5% (v/v) water and 1% (v/v) triisopropylsilane for 7 minutes at 60° C. Alternatively, cleavage consisted of using a mixture of 82.5% TFA, 2.5% (v/v) 1,2-ethanedithiol (EDT), 5% (v/v) water and 5% (v/v) thioanisole and 5% (v/v) phenol for 7 minutes at 60° C. Peptides were there triturated three times using cold diethyl ether. The resulting precipitate was then dissolved in 50% A: 50% B and lyophilized.

Crude peptides were then dissolved in the minimal amount of 95% A: 5% B and purified by reverse phase (RP) HPLC using an Agilent Zorbax C3 column (21.2×250 mm, 7 m) using a linear gradient from 95% A: 5% B to 55% A: 45% B over 120 minutes at a flow rate of 7 mL/min or at a flow rate of 4 mL/min. In general, fractions were analyzed for purify by RP-LCMS using method 1.

Exemplary miniproteins and peptides chemically synthesized as C-terminal amides using a rink linker as described above (Table 2).

TABLE 2

Name, sequence, calculated and observed mass of miniproteins and peptides.

| Name | Sequence | Calculated mass | Observed mass |
| --- | --- | --- | --- |
| MP01-Full | MHQKYKMTKDCFFSFLAHHKKRKL YPMSGSGSLGHEIHEIFIHRL (SEQ ID NO: 81) | 5078.5 | 5078.6 |
| MP01-C | MHQKYKMTKDCFFSFLAHHKKRKL YPMSG (SEQ ID NO: 13) | 3585.8 | 3585.7 |
| MP02-Full | MPNYGPLSPSQPSHGYTFWMVPIW DNSHNAAGSGSLGHHHHHHRL (SEQ ID NO: 82) | 5049.3 | 5049.3 |
| MP03 | MTSVTASLLMHFCPIRAHITNKPS FNPSG (SEQ ID NO: 40) | 3155.6 | 3155.7 |
| MP04 | MRTPIKFAPRLSQPFCPFRKQHQL HLHPLIEG (SEQ ID NO: 42) | 3821.1 | 3821.2 |
| MP05 | MRPCARRDRTLWCPFDSPAWFLLS GFSCG (SEQ ID NO: 44) | 3373.6 | 3373.7 |
| MP06 | MGIVHNATRFPKRCFYSFIATRQS KNSIRVSG (SEQ ID NO: 49) | 3669.9 | 3670.0 |
| MP07 | MKTFSSDQRFSKKCYRIYFHKLRQ RNHNTSVG (SEQ ID NO: 52) | 3961.0 | 3961.1 |
| MP08 | MQHEDLCTWYGFCPSGNFTPRNLR GDSDG (SEQ ID NO: 53) | 3301.4 | 3301.5 |
| MP09 | MRYIYVLRLKSWCGGASARSSPRS CATKLLG (SEQ ID NO: 56) | 3428.8 | 3428.8 |
| MP10 | MHNAYLRKSMRQLCYFRRTLHNIH VMSHRG (SEQ ID NO: 59) | 3753.9 | 3754.0 |
| GCPG | GCPGGLLKNK (SEQ ID NO: 184) | 984.6 | 984.6 |
| S-pep-1 | YALPSTGG (SEQ ID NO: 185) | 763.4 | 763.4 |
| S-pep-2 | GGGGGAGYLLGKINLKALAALAKK IL (SEQ ID NO: 186) | 2465.5 | 2465.5 |
| MP01-T | KMTKDCFFSFL (SEQ ID NO: 159) | 1364.7 | 1364.7 |

Example 3: Capture Agent Synthesis

Conjugation of Carboxy-PEG-Thiol to Pentafluorophenyl Sulfide

A solution consisting of 5 mM carboxy-(PEG)$_{12}$-thiol, 500 mM pentafluorophenyl sulfide, 20 mM triphenylphosphine and 230 mM DIEA in acetonitrile was vortexed and left at room temperature for 4 hours. The reaction was then diluted with 10.6× volume of 95% A: 5% B, solid phase extracted and lyophilized. The resulting material was analyzed by LCMS (method 2). This product will later be referred to as mCA (modified CA).

Conjugation of CT-Peg-Pfp Sulf to Lys(Bio)-2-Chloro Trityl Choloride Resin 17.7 mg of 2-chlorotrityl chloride resin (0.6-0.7 mmol/g) was reacted with 51.4 mg Fmoc-L-Lys(biotin)-COOH in 1 mL DMF with 71 µL DIEA. The solution was sparged with argon and left overnight. The resin was washed with DMF, DCM and dried. The Fmoc group was removed with 500 µL of a 20% piperidine in DMF solution for 30 minutes at room temperature followed by DMF washes. 20.43 mg of pentafluorophenyl sulfide-PEG-COOH was coupled to the 32.3 mg of dried lysine attached resin with 490 µL DMF, 0.4 µM HATU and 98 µl DIEA. This was left for 2 hours at room temperature and then washed and dried in vacuo. The capture agent was cleaved from the resin with a two hour, room temperature treatment of 95% TFA, 2.5% water, 2.5% TIPS; the cleavage cocktail was evaporated and then 4 mL of 50% A:50% B was added and the resulting solution lyophilized. Crude mass obtained=17.5 mg (method 2).

The capture agent was purified on a C3 with the following method: 10 minutes at 95% A:5% B, 30 minutes of a 1% B increase per minutes to 65% A:35% B, followed by a 150 min, 0.25% B per minute gradient to 35% A:65% B. Fractions were analyzed by LCMS, pure fractions were combined, lyophilized and the final material was characterized by LCMS (method 1).

Capture Agent NMR

A resynthesized stock of the CA was diluted in DMSO-d6 and analyzed by NMR using either 282 or 500 MHz.

$^{19}$F NMR (282 MHz, DMSO-d6) δ −135.46 (d, J=24.4 Hz), −135.97 (dd, J=26.2, 10.7 Hz), −136.67 (dd, J=27.3, 9.8 Hz), −153.35 (t, J=22.5 Hz), −163.58 (t, J=22.8 Hz).

$^{13}$C NMR (150 MHz, DMSO) δ 173.73, 171.87, 170.17, 162.76, 158.13 (d, J=31.4 Hz), 147.90, 147.20 (d, J=14.9 Hz), 146.28, 145.62, 145.52, 142.89, 141.18, 137.33 (d, J=247.0 Hz), 117.23 (t, J=20.6 Hz), 111.27-108.75 (m), 107.20-104.61 (m), 99.56, 69.94, 69.81, 69.75, 69.72, 69.67, 69.60, 69.53, 66.77, 61.08, 59.25, 55.45, 51.71, 39.87, 38.20, 35.82, 35.24, 33.80, 30.87, 28.81, 28.26, 28.07, 25.35, 22.87.

$^{1}$H NMR (500 MHz, DMSO-d6) δ 12.54 (s, 1H), 8.09 (d, J=7.8 Hz, 1H), 7.76 (t, J=5.6 Hz, 1H), 6.43 (s, 1H), 6.37 (s, 1H), 4.30 (dd, J=7.8, 4.9 Hz, 1H), 4.14 (ddd, J=12.1, 7.9, 4.9 Hz, 2H), 2.53-2.47 (m, 1H), 3.65-3.32 (m, 52H), 3.16 (t, J=5.9 Hz, 2H), 3.13-3.05 (m, 1H), 3.05-2.93 (m, 2H), 2.82 (dd, J=12.4, 5.0 Hz, 1H), 2.57 (d, J=12.4 Hz, 1H), 2.46-2.27 (m, 2H), 2.04 (t, J=7.4 Hz, 2H), 1.78-1.13 (m, 11H).

Example 4: mRNA Display

Figure 4:
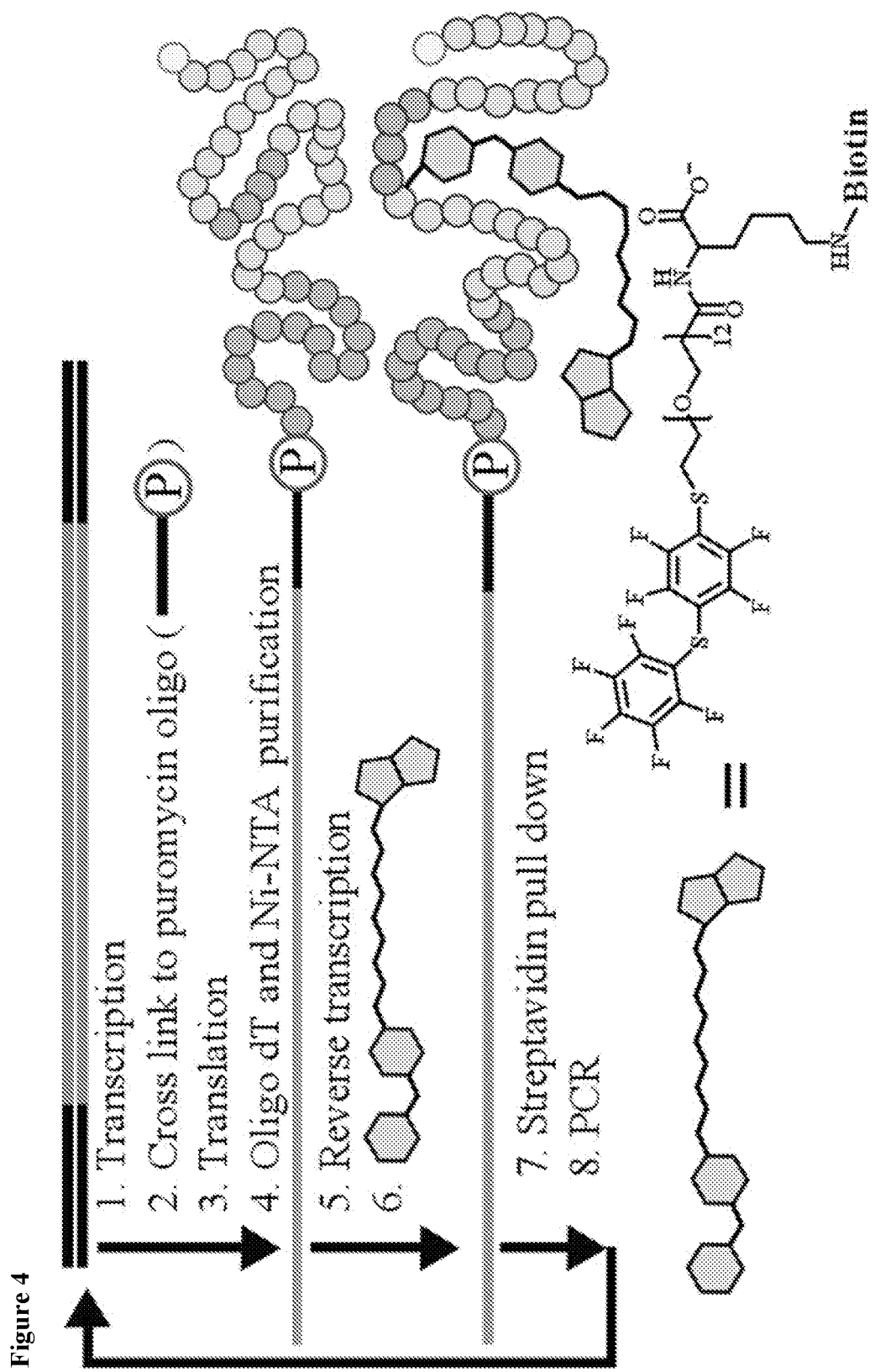
FIG. 4 shows selection scheme with the capture agent (CA) and library design. An mRNA display selection scheme and an embodiment of the water-soluble CA is shown as a cartoon and chemical structure.
Figure 5:
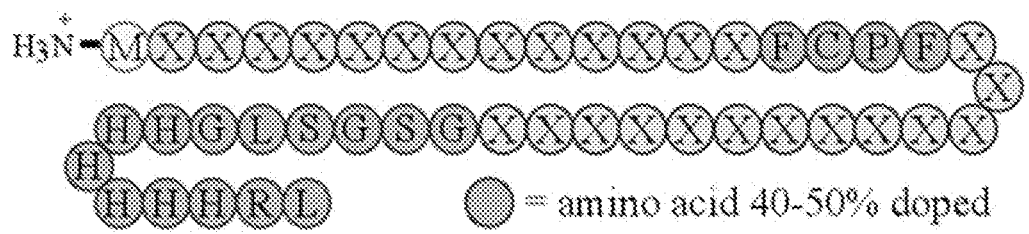
FIG. 5 shows a miniprotein library design sequence (SEQ ID NO: 331) depicting the random region with the doped FCPF (SEQ ID NO: 164) and the C-terminal constant region.
Figure 6:
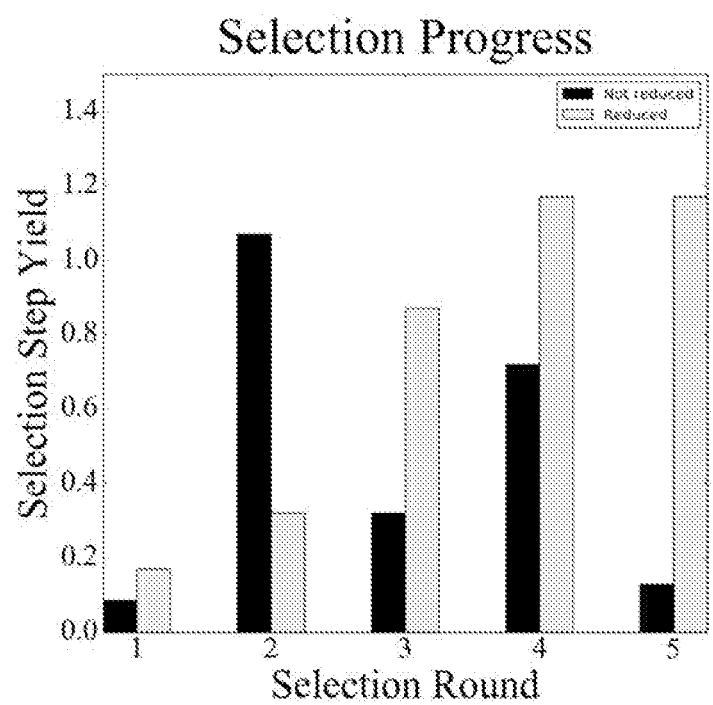
FIG. 6 shows qPCR based selection round yield for both libraries.

To find reactive miniproteins, an mRNA display[48] platform was implemented in which 30-mer sequences were selected to react with a water soluble pentafluorophenyl sulfide-containing, peg- and biotinylated capture agent (CA, FIG. 4). This perfluoroaromatic was chosen due to its sluggish reaction kinetics in water with cysteine containing peptides and its ability to make electron rich electron poor π-π interactions.[49] The GCPG control peptide (SEQ ID NO: 184) was used for measuring the background rate of reaction. Guided from the literature for library design,[50, 51] the library encoded a 30-mer random region with the central 4 amino acids, 40-50% individually doped with the amino acids of the FCPF motif (SEQ ID NO: 164) (2.56-6.25% for the full motif, FIG. 5). This prior knowledge motif slightly biased the library for functional members and allowed testing of its relevance in the context of a miniprotein. The selection commenced with ~5×10$^{13}$ unique miniproteins (measured by qPCR). Following the initial incubation with the CA in non-reducing conditions and streptavidin pull-down, the unreacted library was re-incubated with the CA in the presence of 2 mM 1,4-dithio-DL-threitol (DTT). Thus producing two separate libraries for all of the remaining rounds: one reduced, the other not. The selection proceeded for five rounds with the CA reaction time (FIG. 4, step 6) decreased from either 15 (reduced) or 18 (non-reduced) hours to 30 minutes with a combination of positive and negative selections. The progress of the selection was monitored by qPCR which revealed a gradual increase in the selection round yield for the reduced library and no detectable trend for the non-reduced library (FIG. 6).

Figure 7:
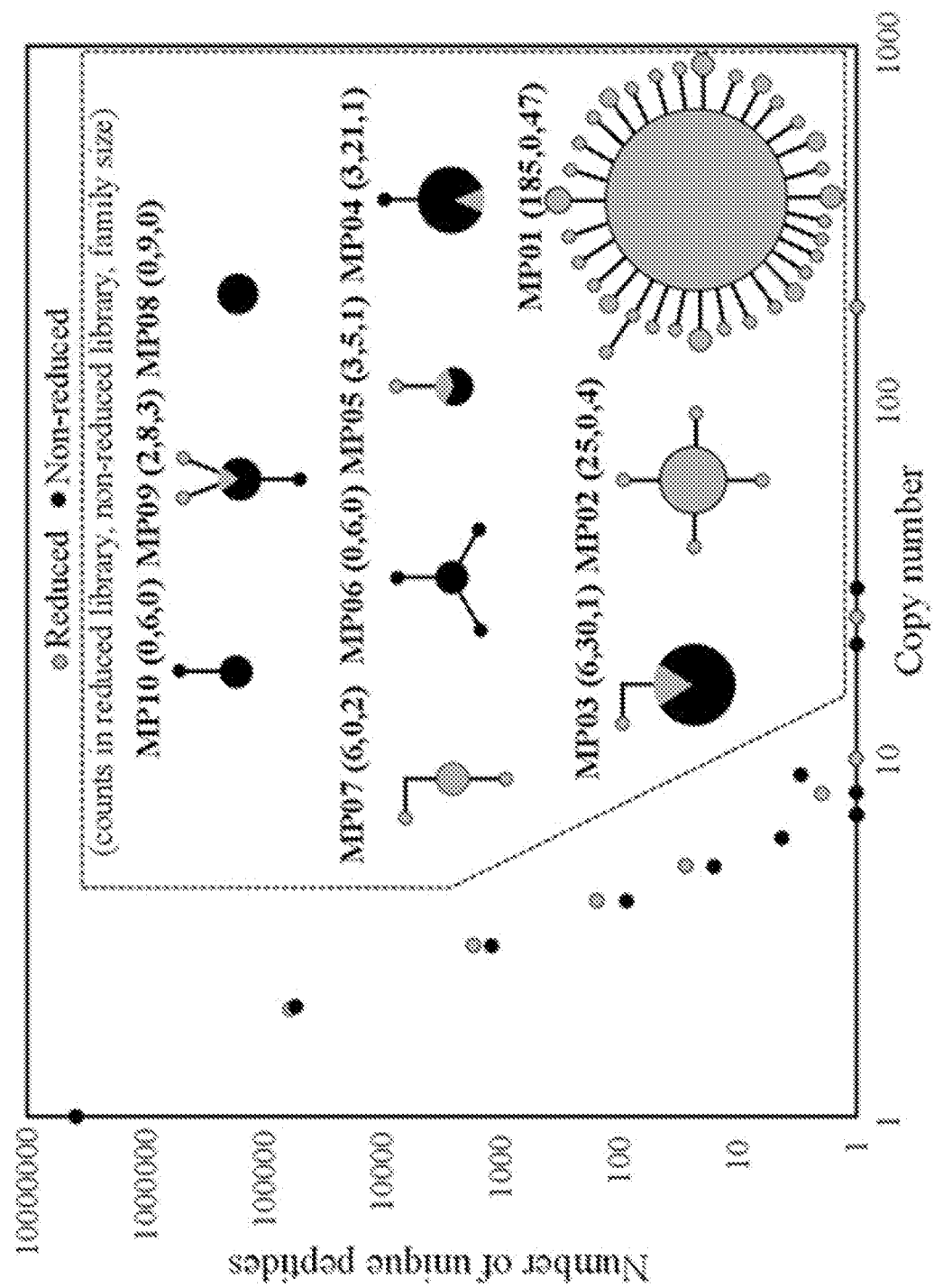
FIG. 7 shows a summary of key NGS data depicting the distributions of unique sequences appearing at discrete copy numbers. Inset is an edit distance family analysis (sequences <7 residues different were considered in the same family) on 10 selected miniproteins. Circles represents a single sequence, the area of which depicts its copy number. Lines connecting circles represent single amino acid difference in the sequence.
Figure 8A:
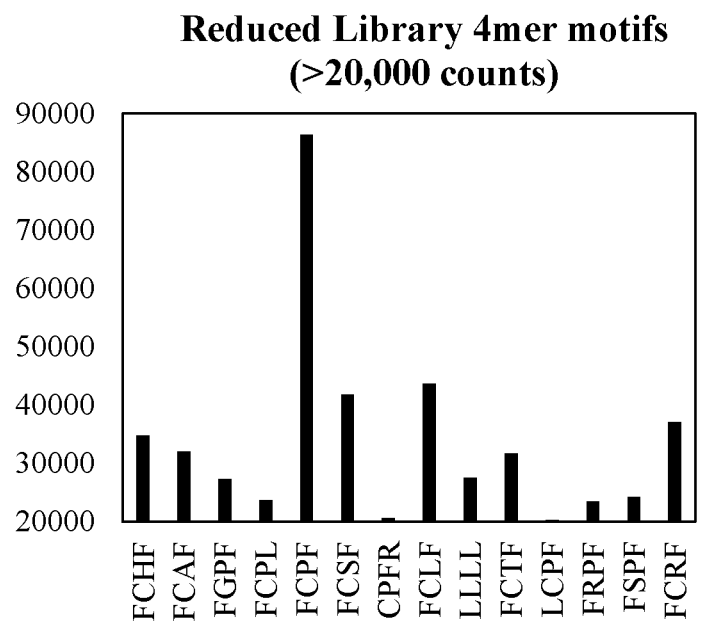
FIG. 8A shows motif analysis for the reduced library depicting the most frequent 4mer motifs (SEQ ID NOs: 160-173, respectively, in order of appearance from left to right).
Figure 8B:
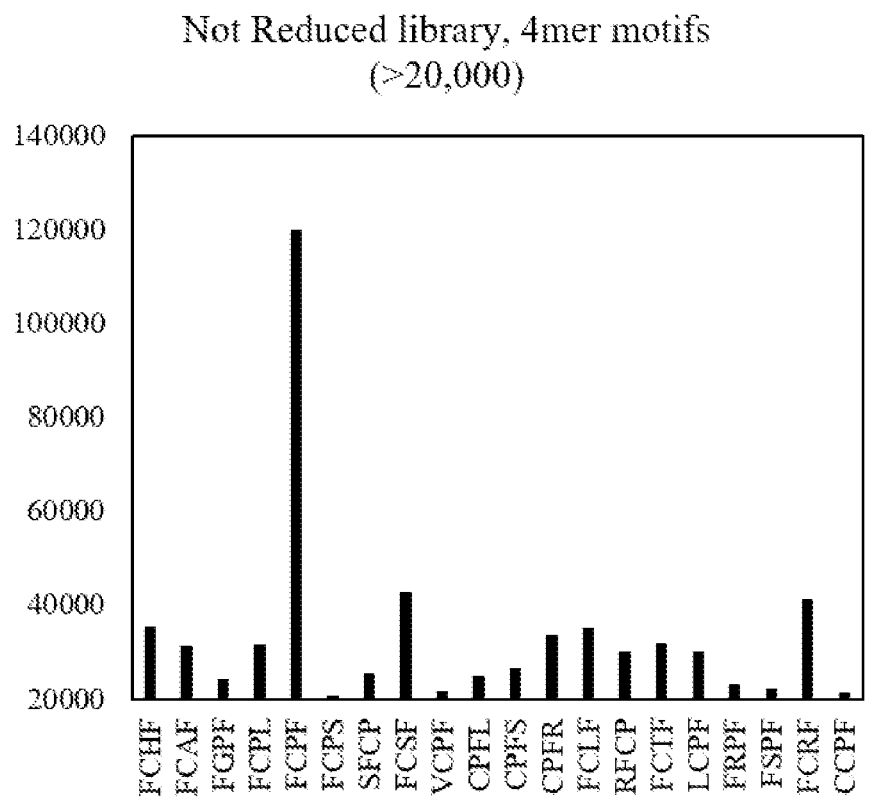
FIG. 8B shows motif analysis for the not reduced library depicting the most frequent 4mer motifs (SEQ ID NOs: 160-164, 174, 175, 165, 176-178, 166, 167, 179, 169-173, and 180, respectively, in order of appearance from left to right).
Figure 9A:
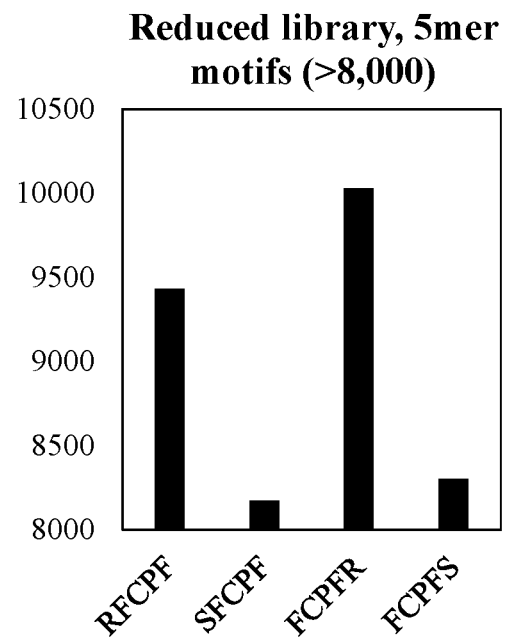
FIG. 9A shows motif analysis for the reduced library depicting the most frequent 5mer motifs (SEQ ID NOs: 196-199, respectively, in order of appearance from left to right).
Figure 9B:
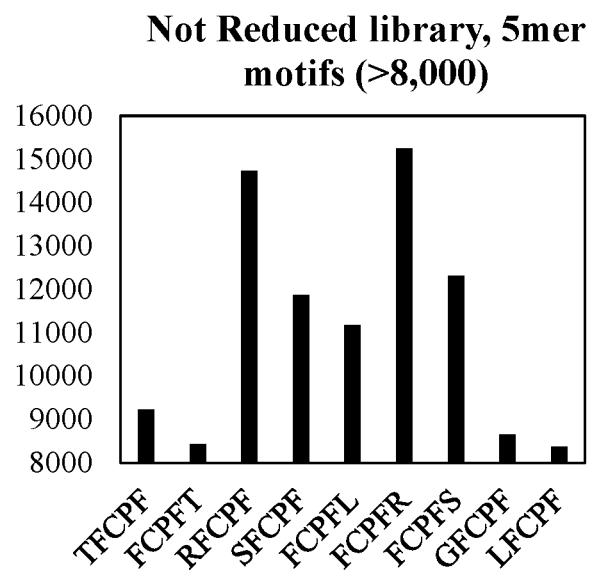
FIG. 9B shows motif analysis for the not reduced library depicting the most frequent 5mer motifs (SEQ ID NOs: 200-208, respectively, in order of appearance from left to right).
Figure 10A:
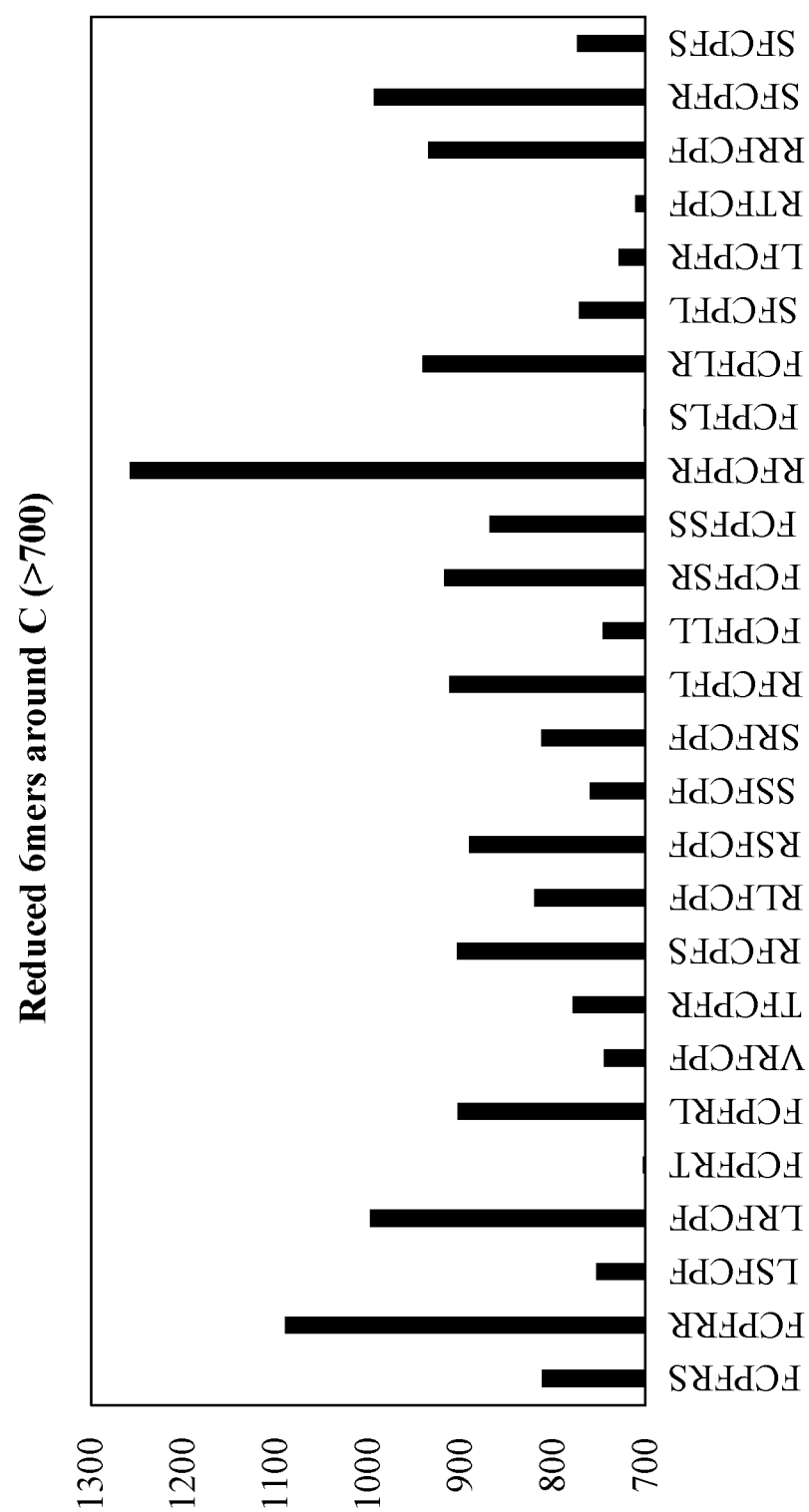
FIG. 10A shows motif analysis for the reduced library depicting the most frequent 6mer motifs (SEQ ID NOs: 209-234, respectively, in order of appearance from left to right).
Figure 10B:
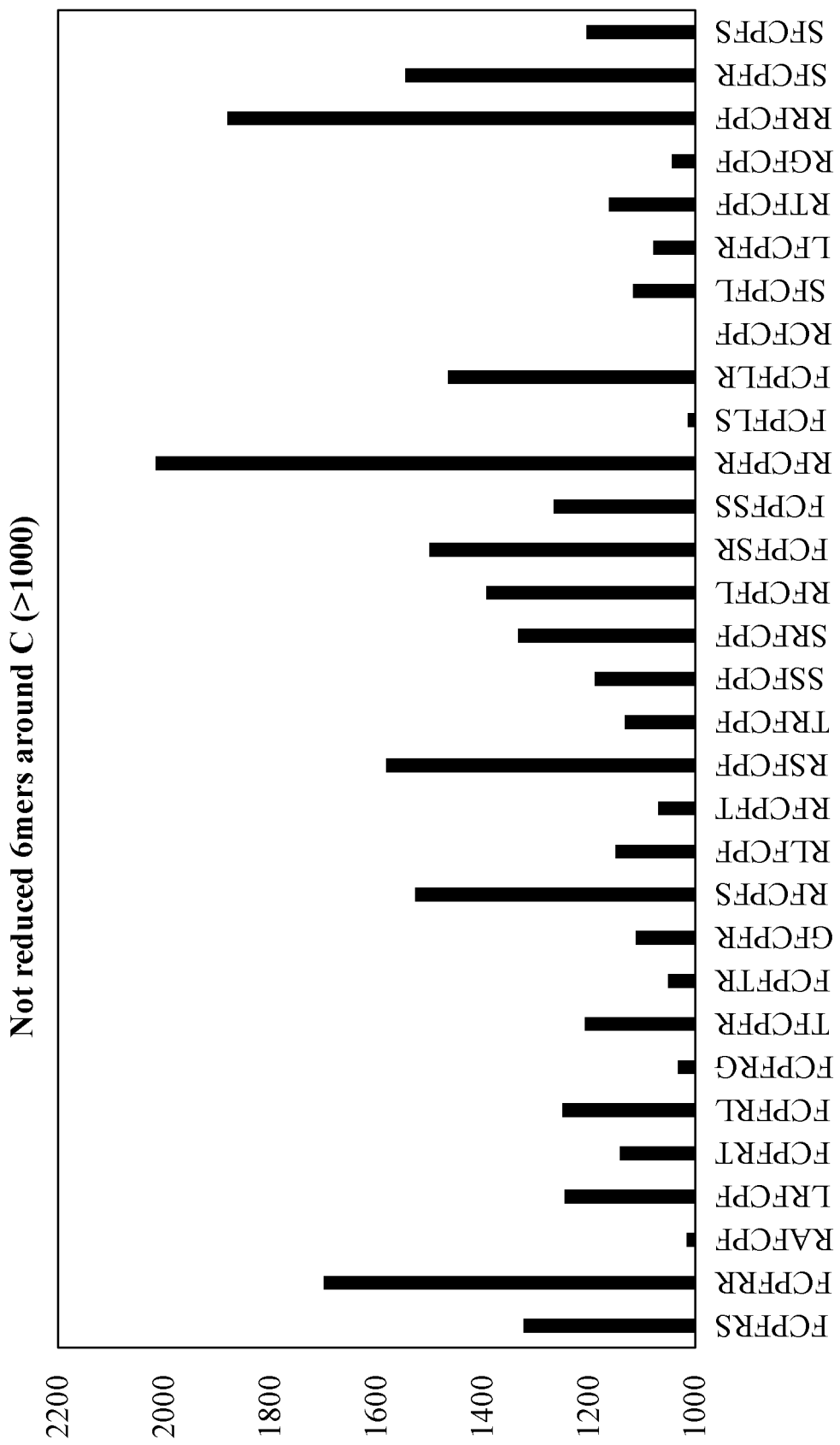
FIG. 10B shows motif analysis for the not reduced library depicting the most frequent 6mer motifs (SEQ ID NOs: 235-265, respectively, in order of appearance from left to right).
Figure 11A:
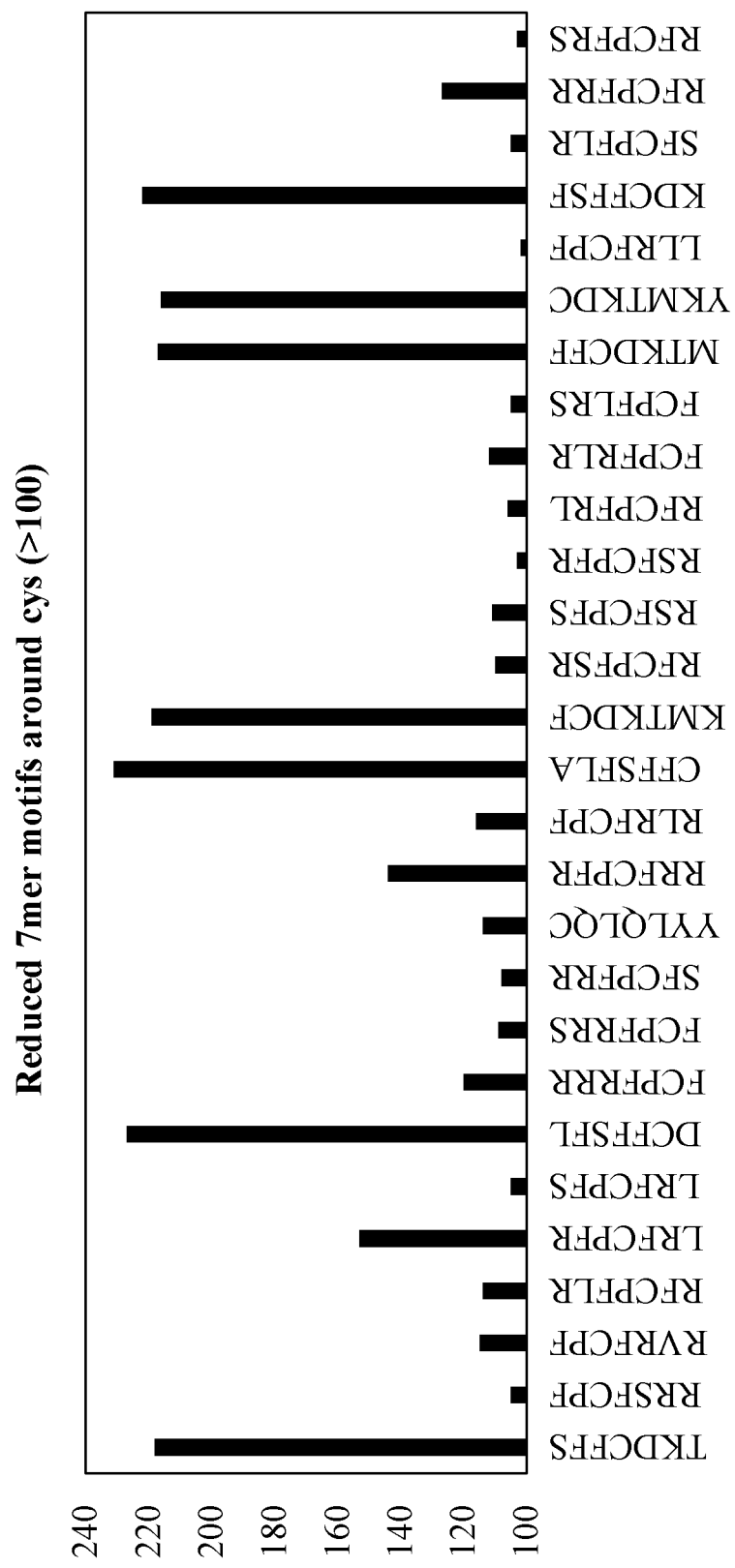
FIG. 11A shows motif analysis for the reduced library depicting the most frequent 7mer motifs (SEQ ID NOs: 266-293, respectively, in order of appearance from left to right).
Figure 11B:
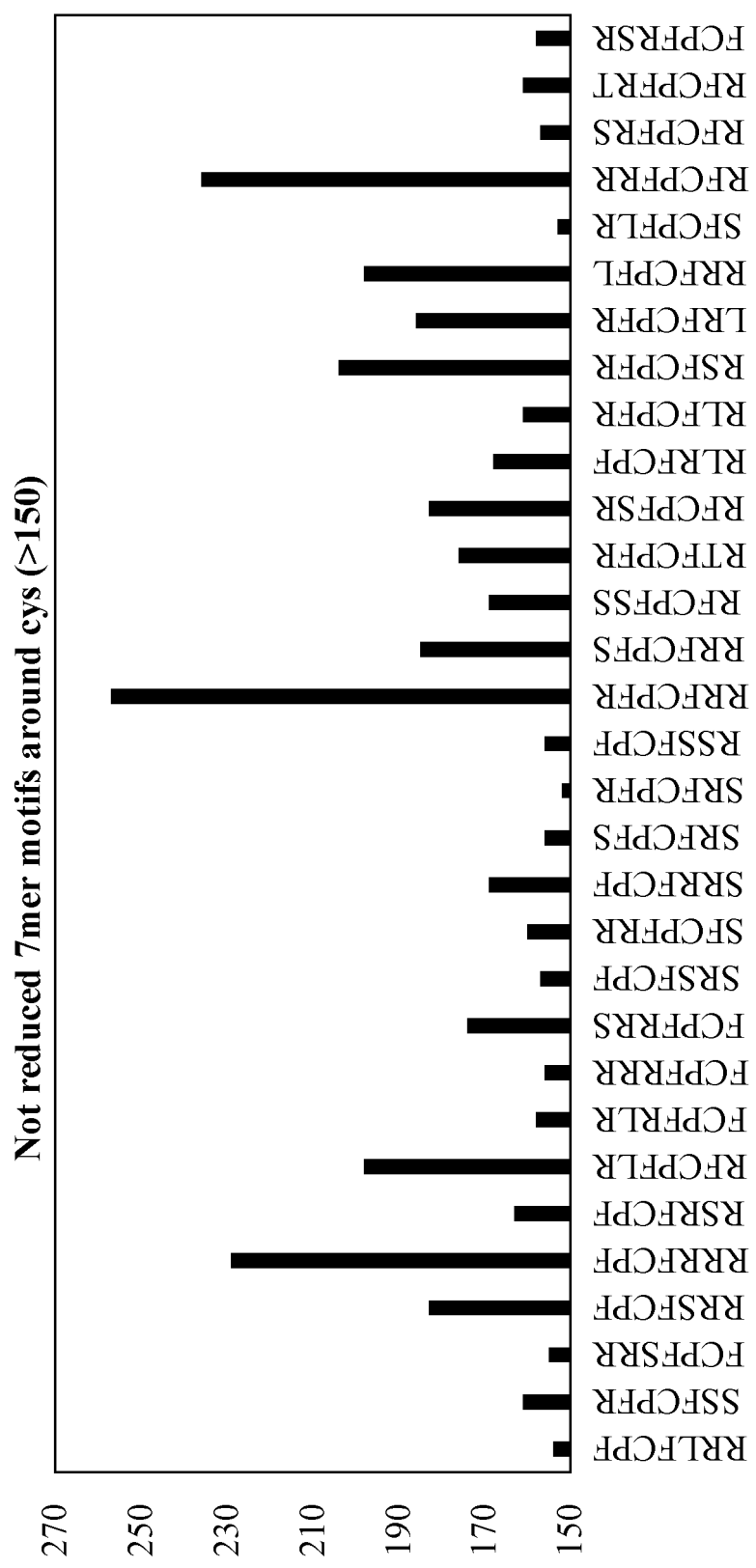
FIG. 11B shows motif analysis for the not reduced library depicting the most frequent 7mer motifs (SEQ ID NOs: 294-324, respectively, in order of appearance from left to right).

To hasten the selection process, NGS was performed on the DNA library following round 5. NGS is heavily utilized in selection processes,[52, 53] allowing researchers to understand population dynamics between rounds,[54, 55] to measure high-throughput dissociation constants[56] or rapidly identify functional biomolecules, even after a single round of selection.[57] The initial library size was >10$^{13}$ and therefore sequencing after a single round was not possible. However, stagnation of the qPCR yield observed for the reduced library between rounds 4 and 5 prompted us to perform Illumina MiSeq sequencing. NGS revealed libraries still in the beginning phases of winnowing and enrichment since the majority of the ~3.9 million sequences only appeared one time (FIG. 7). Following a Pareto-like distribution, the number of sequences with higher copy numbers rapidly dropped off. Analysis of the amino acid frequencies for both libraries revealed there was minimal bias in the dispersion of amino acids in the library and the prevalence of the individual amino acids in the FCPF motif (SEQ ID NO: 164) heavily dropped off as the sequence copy number increased. These above findings in conjunction with the fact that the FCPF motif (SEQ ID NO: 164) was only observed ~2-3% of the time for both libraries, suggests this motif may not be ideal in the center of the miniprotein as it was not enriched for (it was however conserved relative to theoretical preselection levels from doping). Short motif analysis yielded no new, major motifs surrounding cysteine, as most 4-mer motifs possessed components of FCPF (SEQ ID NO: 164) (FIGS. 8A and 8B). Longer motifs only suggested that the FCPF sequence (SEQ ID NO: 164) may favor being flanked by either Arg, Ser, and to a lesser extent Leu as these were slightly overrepresented in 5, 6, and 7-mer subsequences surrounding the cysteine (FIGS. 9A-11B).

Contrary to short motifs, full-length peptide families appeared (FIG. 7 inset). To extract putative miniprotein sequences (MPs) for validation, sequences were analyzed from the tail of the distribution possessing either high copy numbers, large edit distance families (all sequences which differ in <7 amino acid positions were considered in the same family), or those appearing in both libraries. By analyzing the composition of the sequence families, several putative sequences were captured at the start of their evolution. In particular, MP01 which appeared 185 times and possessed a large family of related miniproteins (47 members), 46 of which were a single amino acid substitution different and one that was two amino acids different. Of the 10 sequences selected for further analysis, four appeared in both libraries, all but one possessed small families, and several contained two or even three cysteines (Table 3). The most prevalent sequence (MP01; SEQ ID NO: 13) possessed no major motifs seen elsewhere in the library, MP02 (SEQ ID NO: 39) contained no cysteine, and only one sequence (MP04; SEQ ID NO: 42) contained the FCPF motif (SEQ ID NO: 164). MP03 (SEQ ID NO: 40), MP05 (SEQ ID NO: 44), and MP08 (SEQ ID NO: 53) contained neighboring FCPI (SEQ ID NO: 181), WCPF (SEQ ID NO: 182) and FCPS (SEQ ID NO: 174) subsequences respectively.

TABLE 3

Reaction rates for identified self-labeling miniprotein sequences and truncated MP01, corresponding to SEQ ID NOS: 13, 39, 40, 42, 44, 49, 52, 53, 56, 59, and 159, respectively in order of appearance.

| Peptide | Sequence | Second order rate constant ($M^{-1}$ $s^{-1}$) |
|---|---|---|
| MP01 | MHQKY KMTKD[10] CFFSF LAHHK[20] KRKLY PMSG | 0.34 ± 0.06[a]/ 0.28 ± 0.02[b] |
| MP02 | MPNYG PLSPS[10] QPSHG YTFWM[20] VPIWD NSHNA[30] AG | No Reaction[b] |
| MP03 | MTSVT ASLLM[10] HPCPI RAHIT[20] NKPSF NPSG | 0.04 |
| MP04 | MRTPI KFAPR[10] LSQPF CPFRK[20] QHQLH LHPLI[30] EG | 0.24 ± 0.01 |
| MP05 | MRPCA RRDRT[10] LWCPF DSPAW[20] FLLSG FSCG | 0.93 ± 0.11[c] |
| MP06 | MGIVH NATRF[10] PKRCF YSFIA[20] TRQSK NSIRV[30] SG | 0.11 ± 0.01 |
| MP07 | MKTFS SDQRF[10] SKKCY RIYFH[20] KLRQR NHNTS[30] VG | 0.91 ± 0.14[a] |
| MP08 | MQHWD LCTWY[10] GFCPS GNFTP[20] RNLPG DSDG | 0.04[d] |
| MP09 | MRYIY VLRLK[10] SWCGG ASARS[20] SPRSC ATKLL[30] G | 0.52 ± 0.01[d] |
| MP10 | MHNAY LRKSM[10] RQLCY FRRTL[20] HNIHV MSHRG[30] | 1.66 ± 0.48[a] |
| MP01-T | KMTKD CFFSF[10] L | 0.06 |

Second order rates constants were measured via LC-MS total ion current (TIC) peak integration for the reaction between the MP (0.1 mM) and CA (0.5 mM). Bolded cysteines are trypsin/chymotrypsin digest-LC-MS/MS observed labeling locations. For example, a fragment DC*FF (SEQ ID NO: 332), where * is the covalently bound CA, was observed in the digested MP01 post-labeling. For example, a fragment QLC*Y (SEQ ID NO: 325), where * is the covalently bound CA, was observed in the digested MP10 post-labeling. [a]Constant calculated from averaging of three, different starting MP concentrations. [b]Data obtained using the full length C-terminal region from the library design (-SGSLGHHHHHHRL; SEQ ID NO: 187). [c]Labeled 1-3 times, [d]Labeled 1-2 times.

All 10 putative self-labeling MPs were chemically synthesized (MP01 and MP02 were additionally made with the full C-terminal constant region). To determine the importance of the C-terminal tag, a kinetic analysis on MP01 was conducted comparing the sequence with and without the tag. Using 0.1 mM MP and 0.5 mM CA with 5 mM tris (2-carboxyethyl)phosphine (TCEP) and 1× selection buffer, pH 7.4 at room temperature (RT, conditions used for all kinetics data), both MP01 constructs (SEQ ID NOs: 81 and 13) were shown to possess similar rate constants (0.34 and 0.28 $\mu M^{-1}$ $s^{-1}$), suggesting that the reactivity was conferred by the selected region. MP02 (SEQ ID NOs: 82 and 39) appeared to be a false positive as it did not react over the course of 8 hours, despite the high copy number. The remainder of the MPs all reacted with varying second order rate constants and to differing product distributions from multiple cysteine labeling sites (Table 3). MP07 (SEQ ID NO: 52) and MP10 (SEQ ID NO: 59) both showed rate constants greater than MP01 (SEQ ID NO: 13), demonstrating the absolute sequence count is not an indicative readout for predicting function as has been suggested.[56, 58] These sequences delivered high conversion in one hour, with MP10 (SEQ ID NO: 59) displaying a ~529× rate enhancement over a non-selected Cys peptide. Of the sequences containing multiple cysteines, all reacted to differing extents. En route to being labeled twice, MP09 (SEQ ID NO: 56) displayed biphasic kinetics with an initial rate of 0.52 $M^{-1}$ $s^{-1}$. On the other hand, MP08 (SEQ ID NO: 53) reacted sluggishly (0.04 $\mu M^{-1}$ $s^{-1}$) to produce singly and doubly labeled species. The sole sequence containing three cysteines, MP05 (SEQ ID NO: 44), yielded a mixture of labeled species within an 8-hour reaction—primarily existing with either 2 or 3 labels with a rapid initial labeling process (0.93±0.11 $\mu M^{-1}$ $s^{-1}$). Finally, MP01, 07 and 10 (SEQ ID NOs: 13, 52, and 59, respectively) were probed via proteolytic digest-LC-MS/MS analysis, this confirmed that the cysteines were labeled and not an alternative amino acid. To determine whether the lysine and biotin on the CA were required for labeling, MP01 and 10 (SEQ ID NOs: 13 and 59, respectively) were reacted with a modified CA (mCA) and shown to possess similar conversions for both probes (91 CA/96% mCA conversions for MP10 and 83 CA/91 mCA % for MP01). These data suggest that the two moieties are not required for labeling. Conditions used were 0.5 mM CA, 0.1 mM MP, 5 mM TCEP, 1× selection buffer, pH 7.4. For MP01, the selection capture agent displayed an 83% conversion while the modified CA showed a 91% conversion based on integrated area of the TIC peak for the starting material. Likewise, for MP10 (SEQ ID NO: 59), the selection CA displayed a 91% conversion while the modified CA showed a 96% conversion.

Three sequences (MP01, 07 and 10; SEQ ID NOs: 13, 52, and 59, respectively) did not contain the FCPF motif (SEQ ID NO: 164), suggesting that the functional landscape for $S_NAr$-active MPs is much larger than initially anticipated. In line with the dearth of FCPF motifs (SEQ ID NO: 164) present in the NGS analysis, the majority of MPs with the FCPF (SEQ ID NO: 164) or similar sequences possessed a decreased rate constant relative to sequences lacking the motif. To begin to test whether MP01 possesses a small motif (similar to FCPF; SEQ ID NO: 164) or requires longer-range interactions, the rate constant was measured with a truncated version MP01-T. This sequence displayed a severely diminished activity (Table 3) suggesting that full reactivity requires a larger sequence and it is not a small motif.

TABLE 4

Reaction rates for exemplary self-labeling miniprotein sequences, corresponding to SEQ ID NOs: 144-158, respectively in order of appearance.

| SEQ ID NO: | Sequence | Rate ($M^{-1}$ $s^{-1}$) | Name |
|---|---|---|---|
| 144 | MVKLSGKERTTRNCFFSFLASRRTKKFNNLSG | 0.23 | MP12 |
| 145 | MGHLHICMVWRVNTSGHILSVGHKSYSSHKTG | 2.41 | MP13 |
| 146 | MSSGTHYGILNMVIRCHLVKNQTSQMVVLTTG | 0.12 | MP14 |

TABLE 4 -continued

Reaction rates for exemplary self-labeling mini-protein sequences, corresponding to SEQ ID NOs: 144-158, respectively in order of appearance.

| SEQ ID NO: | Sequence | Rate ($M^{-1} s^{-1}$) | Name |
|---|---|---|---|
| 147 | MHHYCSKMKRRILMHYLFANTMAHRDLGTNG | 10.09 | MP15 |
| 148 | MHLRMIRYLNRRRHLCHVVEIRHGLFASREIG | 0.19 | MP16 |
| 149 | MNGHYPCYLITSVLVGATTSGVPVVVHLRVG | 0.11 | MP17 |
| 150 | MRHYHLTCFQGFRIFRRTVDSLEMEISLG | 0.17 | MP18 |
| 151 | MHMHKTTSYRIRVLVGVDVYRMSHTCLTSSSG | 0.21 | MP19 |
| 152 | MHTSLRSRAKSHSRSFGKCASIYTRYLKMG | 1.22 | MP20 |
| 153 | MQNSKHRPRRCLRLLPLLRGHLHRMFRERG | 2.00 | MP21 |
| 154 | MRSTHQRVRRPRNLCSFKHKWLIKFLKTLTG | 4.94 | MP22 |
| 155 | MRRTPSTRARGRVFLLPTLRFFITLCNLNG | 0.02 | MP24 |
| 156 | MNRIFHKRSTYQMVFGRCSDFTSTYHVLISYG | 0.25 | MP25 |
| 157 | MTATSSSTSRGCRPSTAQVVQRLRGLLLVVG | 0.07 | MP26 |
| 158 | MLFMRLTKKTMATKFCPFRRKRKHRERRALYG | 0.61 | MP27 |

Library Design

The library was designed to display a 30mer random miniprotein with the 14th-17th amino acids being doped as 40-50% FCPF (SEQ ID NO: 164) with the following 188mer DNA sequence:

(SEQ ID NO: 188)
5'-TAA TAC GAC TCA CTA TAG GGA CAA TTA CTA TTT ACA

ATT ACA ATG NNS NNS NNS NNS NNS NNS NNS NNS NNS

NNS NNS NNS NNS WWZ WYZ XXZ WWZ NNS NNS NNS NNS

NNS NNS NNS NNS NNS NNS NNS NNS NNS GGC TCC GGT

AGC TTA GGC CAC CAT CAC CAT CAC CAC CGG CTA TAG

GTA GCT AG-3'

The doped FCPF (SEQ ID NO: 164) was created with the following A:T:G:C ratios during DNA synthesis: W-(1:7:1:1), X-(1:1:1:7), Y-(1:1:7:1) while the G:C ratio for Z was (1:9). For this selection the following primers and oligonucleotides were purchased and used:

Library[a]:
(SEQ ID NO: 189)
5'-TCA CTA TAG GGA CAA TTA CTA TTT ACA ATT ACA

ATG NNS NNS NNS NNS NNS NNS NNS NNS NNS NNS NNS

NNS NNS WWZ WYZ XXZ WWZ NNS NNS NNS NNS NNS NNS

NNS NNS NNS NNS NNS NNS NNS GGC TCC GGT AGC TTA

GGC-3'

F1[b]:
(SEQ ID NO: 190)
5'-TAA TAC GAC TCA CTA TAG GGA CAA TTA CTA TTT

ACA ATT ACA-3'

R1[b]:
(SEQ ID NO: 191)
5'-CTA GCT ACC TAT AGC CGG TGG TGA TGG TGA TGG

TGG CCT AAG CTA CCG GAG CC-3'

RT[b]:
(SEQ ID NO: 192)
5'-TTT TTT TTT TTT TTT GTG ATG GTG ATG GTG GCC

TAA-3'

Psoralen Oligo[a]:
(SEQ ID NO: 193)
5'-Psoralen C6-(uag ccg gug)2'-OMe-AAA AAA AAA AAA AAA-2x Spacer9-ACC-Puromycin-3'
Oligos were purchased from either the Keck
Oligonucleotide Synthesis facility at Yale[a]
(New Haven, CT) or Integrated DNA Technologies[b]
(Coralville, IA)

Selection Round Protocols

Initial Library Construction:

The single stranded DNA library was converted to the desired length dsDNA library in 10 mL of PCR reaction (6 cycles of 30 s 52° C. annealing, 1 min 72° C. extension, 30 s 95° C. denaturing): 25 nM library, 1 μM F1 and R1 primers, 0.2 mM dNTPs, 1× thermo pol buffer and 2.5 U/μL Taq in individual 100 μl total. The library was then phenol/chloroform extracted, 1-butanol concentrated and ethanol precipitated.

TABLE 5

General library statistics

| Reduced library | | Not reduced library | |
|---|---|---|---|
| Total count | 3945597 | Total count | 3923881 |
| Library size with cysteine | 2457256 | Library size with cysteine | 3061270 |
| Library size without cysteine | 1488341 | Library size without cysteine | 862611 |
| Counts of FCPF (SEQ ID NO: 164) | 86277 | Counts of FCPF (SEQ ID NO: 164) | 120081 |

1st Round Transcription:

A reaction containing 50 nM dsDNA template, 1 mM ATP, CTP, UTP, GTP, T7 buffer (1×), 0.4 U/μL RNase OUT and 3 U/μL T7 polymerase (carrying forward~$7.6 \times 10^{13}$ sequences) was left at 37° C. for ~15 hours. This was then purified by 6% denaturing PAGE and passively eluted. The eluted RNA was concentrated with 1-butanol and ethanol precipitated.

1st Round Crosslinking:

Crosslinking was performed with the following reaction: 3 μM RNA, 7.5 μM psoralen oligo, 1× XL buffer (100 mM KCl, 1 mM spermidine, 1 mM EDTA, 20 mM HEPES pH 7.5) as previously described.[51, 59] The mixture was heated to 70° C. for 5 minutes, cooled to RT slowly, then place on ice for >1 min. Then 100 μL reactions were crosslinked in individual wells of a 96-well plate at 4 C with 365 nm light for 20 minutes. All samples were then combined, concentrated with 1-butanol and run on 6% denaturing purification gel. For the first round, ~$1.28 \times 10^{-8}$ moles of RNA were input into the crosslinking reaction; thus, assuming a 2% recovery between crosslinking and input into the selection step along with a 3× oversampling, this amount will produce roughly $5.2 \times 10^{13}$ unique sequences for the first round.

1st Round Translation:

A bulk translation was performed using the following salt optimized mixture: 28 nM XL-RNA, 12.5 µM amino acid mixture without met (AA-met), 12.5 µM AA-leu, 3.5 mM DTT, ~1 mM Mg(OAc)$_2$, 140 mM KCl, min. 0.2 U/µl RNase OUT and 40% rabbit reticulocyte lysate. This was left at 30° C. for 1.5 hours, subsequently salts were added to give ~50 mM Mg$^{2+}$ and 550 mM K$^+$, the reaction was then left for 42 minutes at room temperature, and finally placed in a ~20° C. freezer for 14 hours.

1st Round Oligo dT Purification:

6×, 1 mL suspensions of oligo d(T)25 (SEQ ID NO: 330) magnetic beads (New England Biolabs), were used to purification. The total round 1 translation was split evenly and the same protocol was performed for each of the six bead slurries. The translation mixture was combined with ~6× of dT binding buffer (20 mM tris pH 7.5, 500 mM NaCl, 1 mM EDTA, 0.1% tween 20), added to a bead sample and rocked at room temperature for 1.5 hours. The beads were then washed 1× with 15 mL binding buffer, 3×10 mL wash buffer (20 mM tris pH 7.5, 500 mM NaCl, 1 mM EDTA) and 1×10 mL low salt buffer (20 mM tris pH 7.5, 200 mM NaCl, 1 mM EDTA, each 'wash' incorporated a 15 min incubation). Finally, 1 mL of 20 mM tris (pH 7.5) was added per bead suspension and all six were combined. This final mixture was placed at 65° C. for 4 minutes upon which time the supernatant was removed. Then 5 mL, 10 mM tris buffer were added to beads and the heating protocol was repeated. The two supernatants were combined and the concentration was RNA was determined by UV-vis spectrophotometry. The solution was filtered through a 0.22 m filter, concentrated on a 10K Amicon Ultra centrifugal filter (EMD Millipore) and ethanol precipitated.

1st Round Reverse Transcription:

Reverse transcription was performed with the following conditions: 0.5 mM dNTPs, 1.5 µM RT primer, 10 mM DTT, 1×1st strand buffer, 2 U/µl RNase OUT, 5 U/µl SSII and the suspended mRNA-miniprotein. The RNA and primer were heated together at 65° C. for 5 min first, then cooled to room temperature and finally placed on ice. Then the rest of the components were added and the mixture was incubated at 42° C. for 55 min.

1st Round Ni-NTA:

Two mL Ni-NTA agarose bead slurry were combined with the reverse transcription reaction along with 12 mL of Ni-NTA binding buffer (100 mM NaH$_2$PO$_4$, 6 µM Guan HCl, 0.2% triton X-100, 5 mM β-mercaptoethanol, pH 8) and rocked at 4° C. for 1 hour. The resin was washed 3×10 mL wash buffer (100 mM NaH$_2$PO$_4$, 0.2% triton X-100, 5 mM β-mercaptoethanol, 300 mM NaCl). Then 1 mL aliquots of elution buffer (50 mM NaH$_2$PO$_4$, 300 mM NaCl, 5 mM β-mercaptoethanol, 250 mM imidazole) were added 8 times, each with a 5 min incubation. The elutions were combined, concentrated on a 10K filter and ethanol precipitated.

1st Round Selection:

The pellet was diluted in the round one selection mixture (1 mL total) containing: 1× selection buffer (25 mM HEPES-KOH pH 7.5, 100 mM NaCl, 5 mM CaCl$_2$, 5 mM MgCl$_2$, 0.01% triton X-100), and 50 µM capture agent at ~80 nM RNA-miniprotein—this was termed the non-reduced library. This reacted 15 hours at room temperature, likewise a sample for qPCR was removed (for round 1 input cDNA). The reaction was washed on a 10K filter until the concentration of free capture agent was ~0.12 µM in 550 µl. The concentrated selection mixture was added to ~1 mg preblocked (1× selection buffer and 2 mg/mL yeast tRNA (Roche, Switzerland)) Pierce streptavidin magnetic beads and rotated at room temp for 1 hour. The supernatant was removed and the beads were washed twice with 200 µl, 1× selection buffer, these two washes were then combined with the first supernatant (giving a total volume of ~950 µl) to which 50 µl of 1 mM capture agent and 2 µl of 1 µM DTT (giving ~2 mM) were added. This new, reduced reaction was left at room temperature for 18 hours—likewise an 'input' cDNA sample was removed for qPCR. Following concentration and capture agent dilution, the reduced library was similarly pulled down with ~0.8 mg streptavidin beads. To elute both the reduced and non-reduced libraries from the beads following the initial pulldown, 1 mL washes of 1× selection buffer were performed ten times, then the cDNA was eluted 4× with 100 µl of 10 mM tris pH 7.45 at 95° C. for 3 min each and combined. This cDNA was used for the 'output' of round one.

1st Round PCR:

Standard PCR conditions were used (30 s at 95° C., 30 s at 58° C., and 35 s at 72° C.) and both libraries were amplified for 16 rounds using the F1 and R1 primers. The mixture was then phenol and chloroform extracted, 1-butanol concentrated and ethanol precipitated. The pellet was then diluted in 10 mM tris, 50 mM NaCl and quantified by native PAGE densitometry.

Round 2:

Selection steps through Ni-NTA purification were performed in a similar manner to the first round for both the reduced and non-reduced selections. However, for all steps scaled down reaction sizes were used as it was no longer necessary to carry the entire volume of each step through.

This round diverged from the previous one in the selection step. The precipitated libraries were suspended in 1× selection buffer with or without 2 mM DTT and a sample of round 2 'input' cDNA was removed. These mixtures were then added to 0.15 mg blocked streptavidin magnetic beaded and incubated for 1 hour. The supernatant was removed and combined with the supernatants of four washes of the beads (all using 1× selection buffer), to this, capture agent was added, giving a 50 µM final concentration and ~2.8 µM RNA-miniprotein. The resulting mixture was left for 1 hour at room temperature. The capture agent concentration was then reduced using a 10K filter. For the pull down, 1 mg streptavidin magnetics beads and washed and blocked and finally the selection mixture was added and incubated at RT for 1 hour. The beads were then washed 6×1 mL of 10 mM tris at RT, then 4×1 mL 10 mM tris with a 1 min incubation at 40° C. cDNA was eluted 4×, 50 µl 10 mM tris at 95° C. and then PCR amplified.

Round 3:

Round three proceeded similarly to the previous rounds through the oligo dT purification step. Subsequently, excess salts from the dT purification were removed on a 10K concentrator, and the entire mixture for each selection was spun to 40 µl. To this was added µl 5× selection buffer, 35 µl water and 5 µl 1 mM capture agent, this mixture sat 30 min at room temperature (the 'reduced' library selection step did not have any DTT). This mixture was washed four times with water on a 10K filter; however, before the third spin, the entire solution (plus water wash) was removed from the filter and heated to 65° C. for 2 min (to help remove excess capture agent) and then spun.

After the selection step a standard reverse transcription and Ni-NTA purification (both scaled appropriately) were performed and the final solution was then filtered until the imidazole was ~0.131 µM. Here an 'input' cDNA sample was removed from the non-reduced library. The reduced library was reselected in the same final volume, concentration and time as before but with 2 mM DTT, an 'input' cDNA sample was also removed. This 'redo' selection step was spun on a 10K to remove excess capture agent. Then both libraries were added to 0.2 mg of prewashed and blocked streptavidin magnetic beads and incubated for 1 hour. These beads were then washed 5×1 mL at RT, 5×1 mL with 1 min at 40° C. then eluted 4×, 50 µl 3 min elutions at 95° C. The two libraries were then PCR amplified.

Round 4:

The round four transcription was performed with 70 nM template for 5 hours. This was then gel purified, crosslinked and translated. A standard oligo dT purification was done and then samples were concentrated. Next a solution of 1× selection buffer, 100 µM capture agent and ±3 mM DTT (depending on the library) was created. After 30 minutes, excess capture agent was removed and a standard reverse transcription and Ni-NTA purified were performed. Following this, the solutions were spin filtered until there was only ~0.12 µM imidazole. 'Input' samples for qPCR were then taken. Next 0.25 mg streptavidin magnetic beads were added and incubated for 1 hour. The beads were then washed 3×1 mL 10 mM tris and 50 mM NaCl at room temperature, 7×1 mL with a 1 min 42° C. incubation. Finally, four elutions of 50 µl at 95° C. were performed, and the cDNA was PCR amplified.

Round 5:

Round five followed a scaled down version of round one until the selection step. The libraries were suspended in 1× selection buffer, and the reduced selection received 2 mM TCEP (instead of DTT), these mixtures were then added to prewashed beads for a negative selection and left for 15 min at room temperature. The supernatant was again incubated with a fresh batch of blocked beads for 15 minutes. The supernatant was removed, and both resins was washed with 1× buffer which was then combined with the original supernatant to which was added capture agent to a final concentration of 50 µM; this reacted for 30 minutes. Following excess capture agent removal on a spin filter, round 'input' qPCR samples were removed. The remaining solution was added 1 mg of washed and blocked streptavidin beads for 1 hour. The beads were then washed 4×1 mL at room temperature, 6×1 mL at 42° C. with 1 min incubation, the cDNA was eluted and PCR amplified like normal.

qPCR Analysis

Quantitative PCR was performed at MIT's BioMicroCenter on a Light Cycler 480 II Real-Time PCR machine. To create a standard curve for each round, a sample of known concentration, reverse transcribed RNA was diluted to give a range of DNA concentrations (~4 orders of magnitude). PCR mixes were composed of 1 µM primers, 50% (2×) SYBR Green PCR Master Mix (Applied Biosystems, Foster City, Calif.), DNA template and water. Each reaction was split into three wells for triplicate measurements of $C_p$ values, which were then averaged. Selection round yields were determined using the $C_p$ values from samples of the selection step input and cDNA elution. A yield for each round was determined based off the known volumes of each step and the standard curve correlating $C_p$ and standard DNA concentration.

NGS Data Analysis

Following round 5, the PCR amplified dsDNA was sent to GENEWIZ (South Plainfield, N.J.) for MiSeq (2×150 bp) Illumina sequencing. The FASTQ data was analyzed via custom python scripts that first combined pairs and filtered out DNA sequences possessing less than 85% Q30 Phred scores with ambiguous bases being determined by the higher Q-score base of the pair. Sequence were then translated into amino acid sequences, filtered again based off length and the presence of part of the C terminal fixed region. Sequences were then analyzed according to frequency and size of Levenshtein families with an edit distance less than 5.

Levenshtein clusters (edit distance=6), showing sequence, gray point mutants relative to the cluster parent sequence and number of times each miniprotein appeared in the sequencing.

MP01-Reduced:
MHQKYKMTKDCFFSFLAHHKQRKLYPMSG
(SEQ ID NO: 1): 1,

MHQKYKMTKDCFFSFLAHRKKRKLYPMSG
(SEQ ID NO: 2): 2,

MHQKYKMTKDCFFPFLAHHKKRKLYPMSG
(SEQ ID NO: 3): 1,

MHQKYKMTKDCFFSFLAHHKMRKLYPMSG
(SEQ ID NO: 4): 1,

MHQKYKMTKDCFFSFLAHHRKRKLYPMSG
(SEQ ID NO: 5): 1,

MHQKYKVTKDCFFSFLAHHKKRKLYPMSG
(SEQ ID NO: 6): 1,

MHRKYKMTKDCFFSFLAHHKKRKLYPMSG
(SEQ ID NO: 7): 1,

MHQKYKMTKDCFFSFLAHHKKRKLYPMSG
(SEQ ID NO: 8): 1,

MHQKYKMTKDCFFSFLAHHKKRKSYPMSG
(SEQ ID NO: 9): 1,

MHQKYKMTKDCFFSSLAHHKKRKLYPMSG
(SEQ ID NO: 10): 1

MHQKYKMTKDCFFSFLSHHKKRKLYPMSG
(SEQ ID NO: 11): 1,

MHQKYKMAKDCFFSFLAHHKKRKLYPMSG
(SEQ ID NO: 12): 4

MHQKYKMTKDCFFSFLAHHKKRKLYPMSG
(SEQ ID NO: 13): 185,

MHRKYKMKKDCFFSFLAHHKKRKLYPMSG
(SEQ ID NO: 14): 1

MHQKYEMTKDCFFSFLAHHKKRKLYPMSG
(SEQ ID NO: 15): 1,

MYQKYKMTKDCFFSFLAHHKKRKLYPMSG
(SEQ ID NO: 16): 1

MHQKHKMTKDCFFSFLAHHKKRKLYPMSG
(SEQ ID NO: 17): 2,

MHQKYKMTEDCFFSFLAHHKKRKLYPMSG
(SEQ ID NO: 18): 1

MHQKYKMTRDCFFSFLAHHKKRKLYPMSG
(SEQ ID NO: 19): 3,

MHQKYKMTKNCFFSFLAHHKKRKLYPMSG
(SEQ ID NO: 20): 1

MHQKYK1TKDCFFSFLAHHKKRKLYPMSG
(SEQ ID NO: 21): 1,

MHQKYKMTKDCFFSFLAHHKKRKLYPMNG
(SEQ ID NO: 22): 1

MHQKYKMTKDCFFSFLAHHKKRKLYPTSG
(SEQ ID NO: 23): 2,

```
MHQKYKMTKDCFFSFLAYHKKRKLYPMSG
(SEQ ID NO: 24): 2

MQQKYKMTKDCFFSFLAHHKKRKLYPMSG
(SEQ ID NO: 25): 1,

MHQKCKMTKDCFFSFLAHHKKRKLYPMSG
(SEQ ID NO: 26): 1

MHQKYKMTKDCFFSFLAHHKKRRLYPMSG
(SEQ ID NO: 27): 1,

MHQKYKMTKDCFFSFLTHHKKRKLYPMSG
(SEQ ID NO: 28): 1

MHQKYKMTKDCFLSFLAHHKKRKLYPMSG
(SEQ ID NO: 29): 3,

MHQKYKMTKDCFFSFLAHHKKRKLYPVSG
(SEQ ID NO: 30): 3

MHQKYKMTKDCFSSFLAHHKKRKLYPMSG
(SEQ ID NO: 31): 1,

MHQKYKMTKDCFFSFLAHHKKRKLHPMSG
(SEQ ID NO: 32): 1

MRQKYKMTKDCFFSFLAHHKKRKLYPMSG
(SEQ ID NO: 33): 2,

MHQKYKMTKDCFFSFLAHHKKGKLYPMSG
(SEQ ID NO: 34): 1

MP02-Reduced:
MPNYGPLSPSQPSRGYTFWMVPIWDNSHNAAG
(SEQ ID NO: 35): 1,

MPNHGPLSPSQPSHGYTFWMVPIWDNSHNAAG
(SEQ ID NO: 36): 1,

MPNYGLLSPSQPSHGYTFWMVPIWDNSHNAAG
(SEQ ID NO: 37): 1,

MPNYGPLSPSQPSHGYTFWMVPIWDNSHSAAG
(SEQ ID NO: 38): 1,

MPNYGPLSPSQPSHGYTFWMVPIWDNSHNAAG
(SEQ ID NO: 39): 25

MP0-Reduced:
MTSVTASLLMHFCPIRAHITNKPSFNPSG
(SEQ ID NO: 40): 6,

MTSVTASPLMHLCPIRAHITNKPSFNPSG
(SEQ ID NO: 41): 1

Not reduced:
MTSVTASLLMHFCPIRAHITNKPSFNPSG
(SEQ ID NO: 40): 30

MP04-Reduced:
MRTPIKFAPRLSQPFCPFRKQHQLHLHPLIEG
(SEQ ID NO: 42): 3

Not reduced:
MRTPIKFAPRLSQPFCPFRKQRQLHLHPLIEG
(SEQ ID NO: 43): 1,

MRTPIKFAPRLSQPFCPFRKQHQLHLHPLIEG
(SEQ ID NO: 42): 21

MP05-Reduced:
MRPCARRDRTLWCPFDSPAWFLLSGFSCG
(SEQ ID NO: 44): 3,

MRPCARRG-RTLWCPFDSPAWFLLSGFSC
(SEQ ID NO: 45): 1

Not reduced:
MRPCARRDRTLWCPFDSPAWFLLSGFSCG
(SEQ ID NO: 44): 5

MP06-not reduced:
MGIVHNATRFPKRCFYSFIATRQSMNSIRVSG
(SEQ ID NO: 46): 1,

MGIVHNATRFPKRCFYSFIATRQSKDSIRVSG
(SEQ ID NO: 47): 1,

MGIVHNATRLPKRCFYSFIATRQSKNSIRVSG
(SEQ ID NO: 48): 1,

MGIVHNATRFPKRCFYSFIATRQSKNSIRVSG
(SEQ ID NO: 49): 6

MP07-Reduced:
MRTFSSDQRFSKKCYRIYFHKLRQRNRNTSVG
(SEQ ID NO: 50): 1,

MKTFSSDQRFSKKCYRIYFHKLRQGNHNTSVG
(SEQ ID NO: 51): 1,

MKTFSSDQRFSKKCYRIYFHKLRQRNHNTSVG
(SEQ ID NO: 52): 6

MP08-Not reduced:
MQHEDLCTWYGFCPSGNFTPRNLRGDSDG
(SEQ ID NO: 53): 9

MP09-Reduced:
MRYIYVLRLKSWCGGASARSPPRSCATKLLG
(SEQ ID NO: 54): 1,

MRYVYVLRLKSWCGGASARSSPRSCATKLLG
(SEQ ID NO: 55): 1,

MRYIYVLRLKSWCGGASARSSPRSCATKLLG
(SEQ ID NO: 56): 2

Not reduced:
MRYIYVLRLKSWCGGASARSPPRSCATKLLG
(SEQ ID NO: 57): 1,

MRYIYVLRLKSWCGGASARSSPRSCATKLLG
(SEQ ID NO: 56): 8

MP10-Not reduced:
MHSAYLRKSMRQLCYSRRTLHNIEVMSHRG
(SEQ ID NO: 58): 1,

MHNAYLRKSMRQLCYFRRTLHNIHVMSHRG
(SEQ ID NO: 59): 6
```

Kinetics Data Analysis

Five μl kinetics time point samples were made to capture the initial reaction rate and quenched with the addition of 95 μl of 49.75% $H_2O$, 49.75% Acetonitrile and 0.5% TFA. Following LC-MS analysis, time points within the linear range of the instrument were used for kinetics analysis by integrating the peak area of the starting peptide during the reaction time course. A second order kinetics rate constant ($k_2$) was extracted by fitting the data to the following equation:

$$k_2(A_0 - B_0)t = \ln\left(\frac{B_0 A_t}{A_0 B_t}\right)$$

For this, $A_0$ refers to the initial capture agent concentration, $A_t$ is its concentration at the given time point (for kinetics data, this was determined using $A_0 - B_t$ as the CA peak intensity was outside the linear range of the LC-MS). $B_0$ is the initial miniprotein or peptide concentration and $B_t$ signifies the miniprotein or peptide concentration when the sample was taken. For MP01, 07 and 10 the rate constant is an average of three measurements at different concentration (here error is estimated from the deviation in the three point estimates) while for the rest of the sequences it is estimated from a single MP concentration (for these samples, error bars represent the error determined from a linear regression fit).

Figure 12:
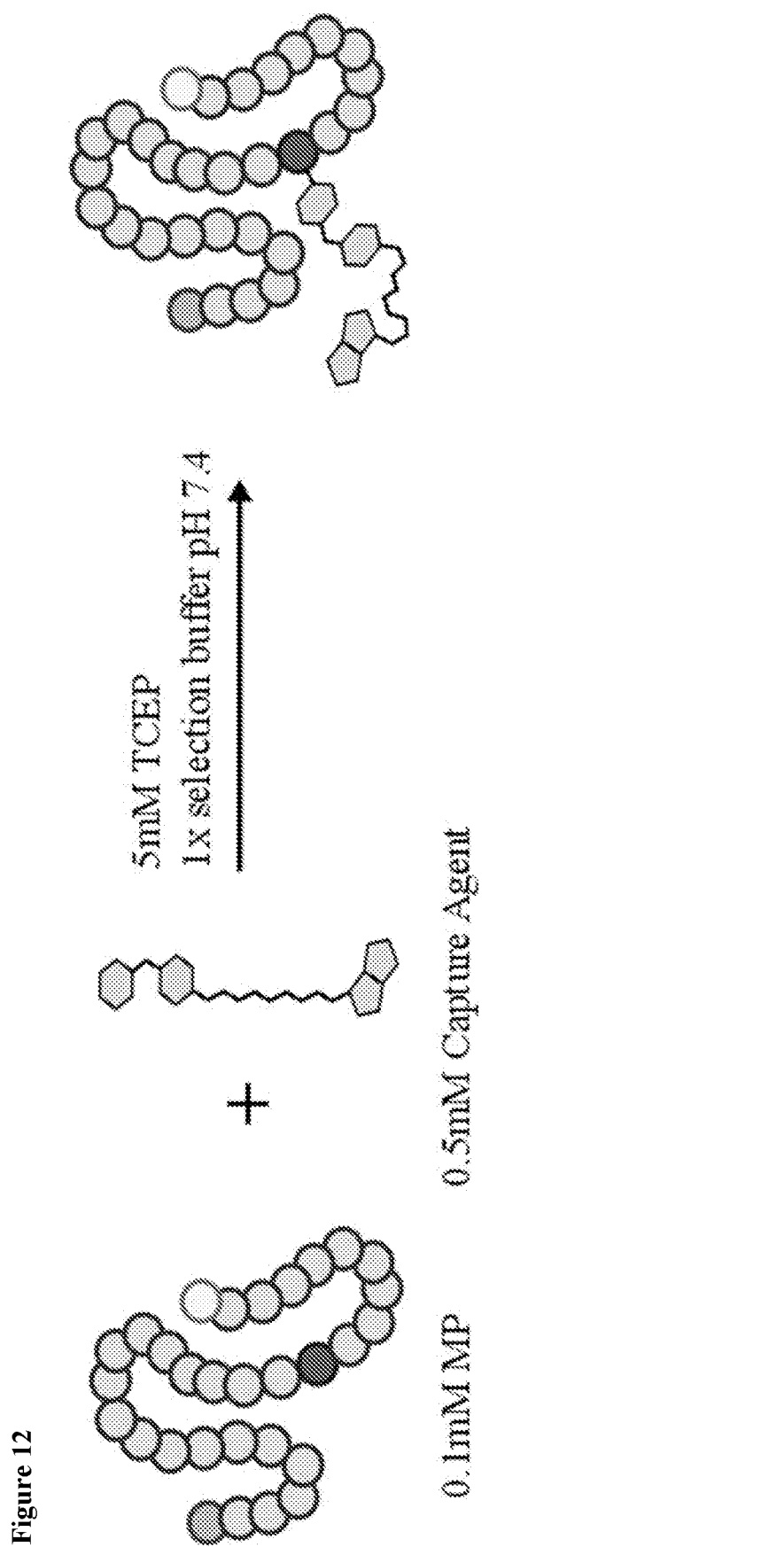
FIG. 12 shows a cartoon depiction of the kinetics measurement reactions.

As an example, below are the times and integrated areas for MP01's kinetics analysis. A cartoon depiction of the kinetics measurement reactions is shown in FIG. 12. Some reactions were performed with 0.1 mM MP, 0.5 mM CA, 5 mM TCEP and 1× selection buffer pH 7.4 at room temperature. Reactions used 100 µM peptide, 500 µM CA, 5 mM TCEP, 1× selection buffer (25 mM pH 7.45 2-[4-(2-hydroxyethyl)piperazin-1-yl]ethanesulfonic acid (HEPES), 100 mM NaCl, 5 mM $CaCl_2$ and 5 mM $MgCl_2$) and were allowed to react at room temperature for selected times. A 5 µl reaction aliquot was quenched at select time points with either 95 µl or 195 µl of quench solution (49.75% water, 49.75% acetonitrile, 0.5% trifluoroacetic acid) depending on whether the analysis was performed using a Agilent 6520 ESI-Q-TOF mass spectrometer or an Agilent 6550 iFunnel Q-TOF mass spectrometer LCMS respectively. An example of data for MP01 (SEQ ID NO: 13) is shown in Table 6.

TABLE 6

Kinetics Data for MP01.

| time (min) | integrated area |
| --- | --- |
| 0 | 138480673 |
| 15 | 123113873 |
| 30 | 101461475 |
| 60 | 79632567 |
| 120 | 45981205 |
| 240 | 27644389 |
| 360 | 8301823 |
| 480 | No peak |

Figure 13:
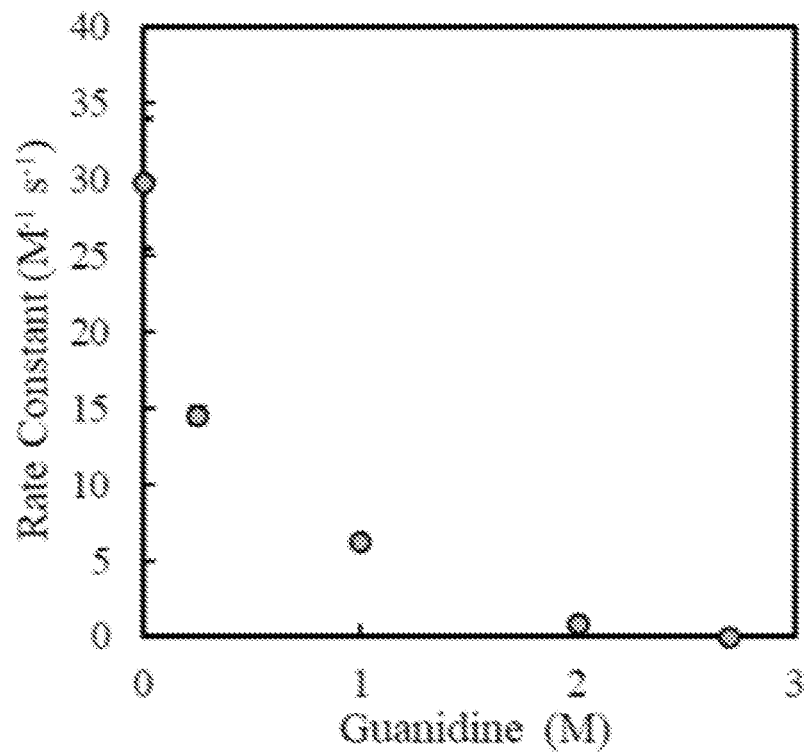
FIG. 13 shows the kinetics of an exemplary miniprotein (Gen4) using standard reaction conditions with the addition of denaturant.
Figure 14A:
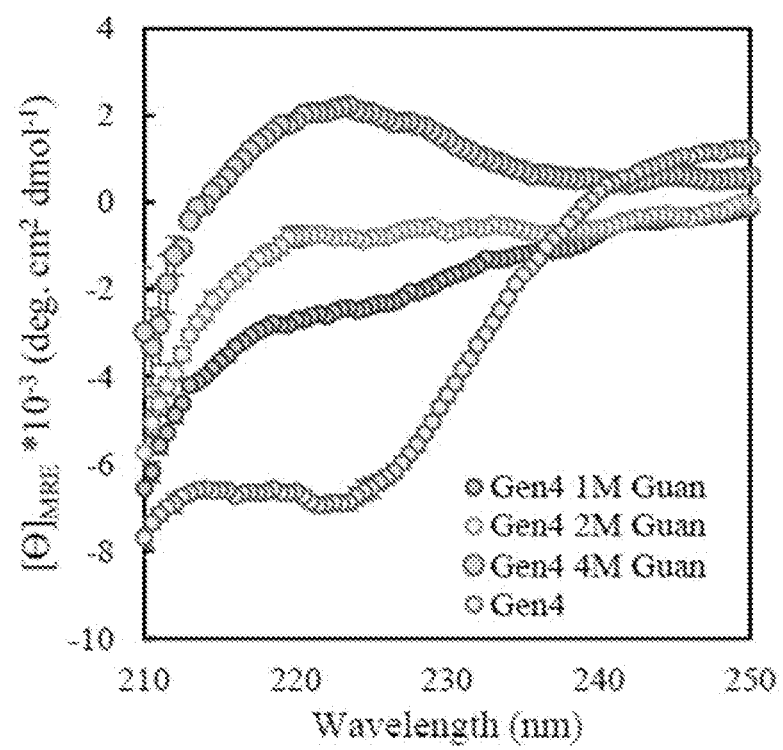
FIG. 14A shows CD analysis of an exemplary miniprotein (Gen4) in the presence and absence of guanidinium chloride.
Figure 14B:
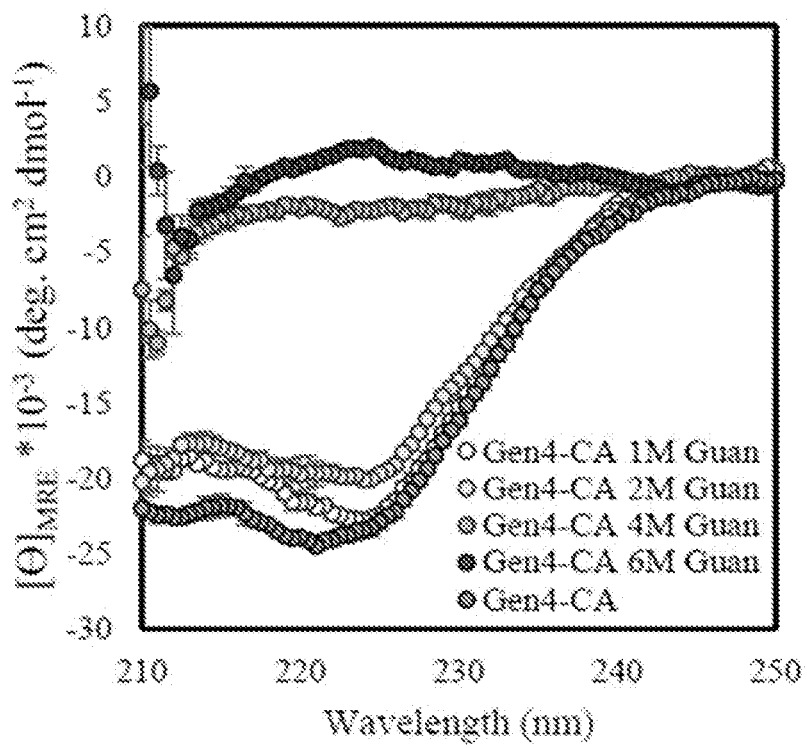
FIG. 14B shows CD analysis of an exemplary CA-bound miniprotein (Gen4-CA) in the presence and absence of guanidinium chloride.
Figure 15:
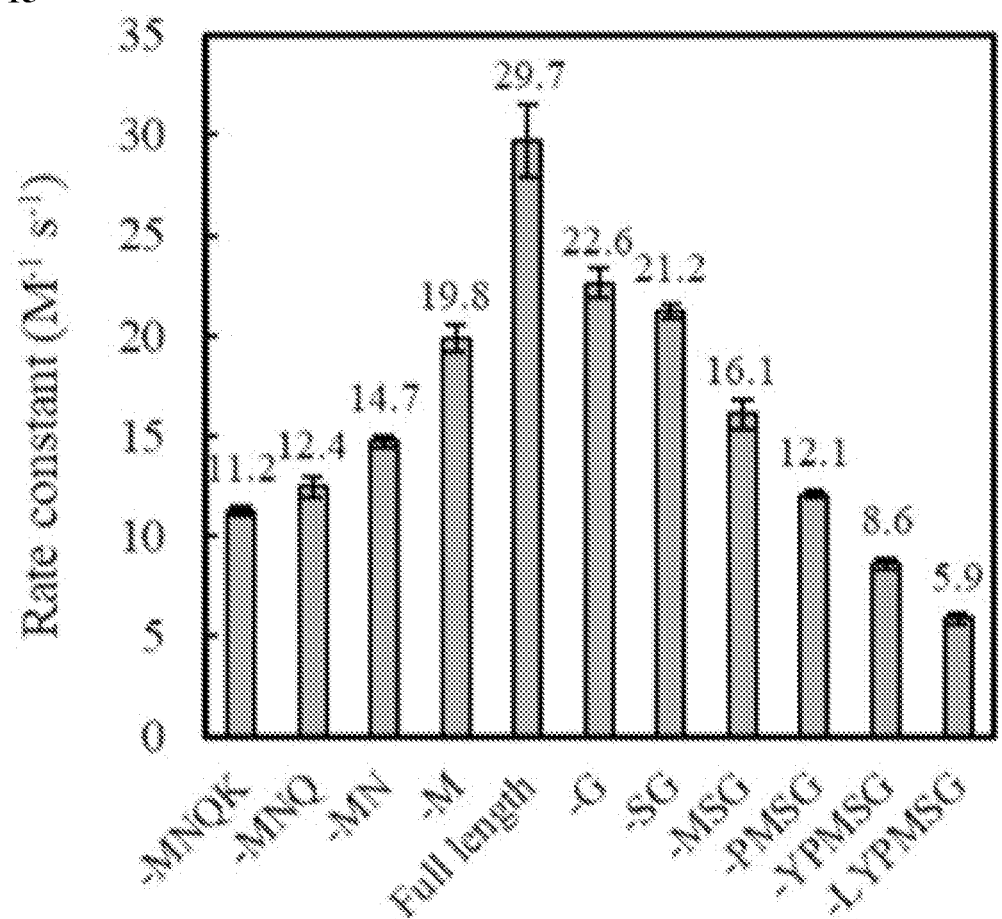
FIG. 15 shows truncation analysis of Gen4 comparing second order rate constants. Figure discloses SEQ ID NOS: 137, 132, 131, 136, 133, and 138-141 as bars and SEQ ID NOS: 329 and 326-328 as labels beneath the bars (for sequences with 4 or more residues), respectively, in order of appearance.
Figure 16:
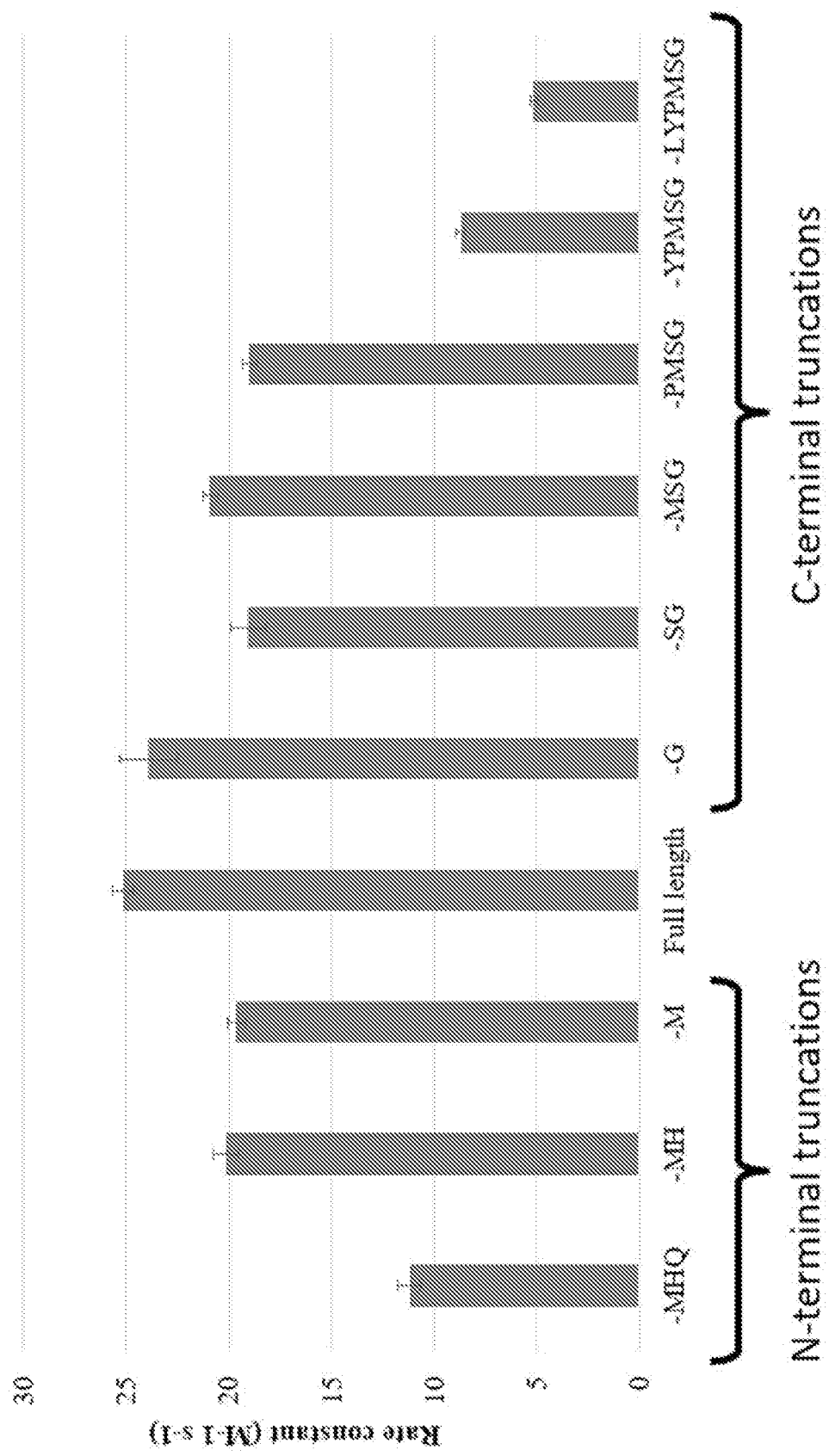
FIG. 16 shows second order rate constants of exemplary truncated miniproteins (Gen3_1). Figure discloses SEQ ID NOS: 132, 131, 130, 116, and 124-129 as bars and SEQ ID NOS: 326-328 as labels beneath the bars (for sequences with 4 or more residues), respectively, in order of appearance.

Kinetics measurements with denaturant were also conducted in a similar way only with the addition of a desired amount of guanidine HCl with pH controlled for all reactions to 7.45. Gen4 displayed kinetics sensitive to additives and truncations. Noticing a structural change induced by labeling, the importance of structure was probed during the reaction. Performing the reaction under increasing concentration of the denaturant guanidinium chloride revealed a rapid and near complete ablation of reactivity in the range of 2-3 M denaturant (FIG. 13). Such denaturation has been shown previously to not alter the mechanism of $S_NAr$ chemistry[24]. Coinciding with this, both the labeled and unlabeled Gen4 displayed increasingly random coil-like secondary structure with increasing concentration of guanidinium chloride via CD, though the labeled version appeared slightly less susceptible to structural alteration at lower concentrations of denaturant relative to the unlabeled form (1-2 µM denaturant, FIGS. 14A and 14B). Using the structure stabilizing additive, trimethylamine N-oxide[60] (TMAO) at 0.5 and 1 µM, the rate constant decreased to ~9.7 and 7.5 $\mu M^{-1} s^{-1}$ respectively, this may suggest the need for conformational flexibility prior to or during the reaction. Sodium chloride and ammonium sulfate both negatively impacted the reaction rate (3.9 $\mu M^{-1} s^{-1}$ for 2 µM ammonium sulfate and 6.1 $\mu M^{-1} s^{-1}$ for 2 µM sodium chloride). This is in contract to the it-clamp motif that also reacts with perfluoroaromatics, but displays a dramatic and beneficial salt-effect from ammonium sulfate[61]. Given a hypothesis that structural rearrangement and flexibility prior to, during or due to the reaction is important, the properties imparted by the full sequence came into question. Producing a series of N- and C-terminal truncations of the Gen4 sequence (SEQ ID NOs: 137, 132, 131, 136, 133, and 138-141) led to a rapid decrease in MP reactivity suggesting a role for the majority of the sequence (FIG. 15). Producing a series of N- and C-terminal truncations of the Gen3_1 sequence (SEQ ID NOs: 132, 131, 130, 116, and 124-129) led to a decrease in MP reactivity suggesting a role for the majority of the sequence (FIG. 16).

Figure 17:
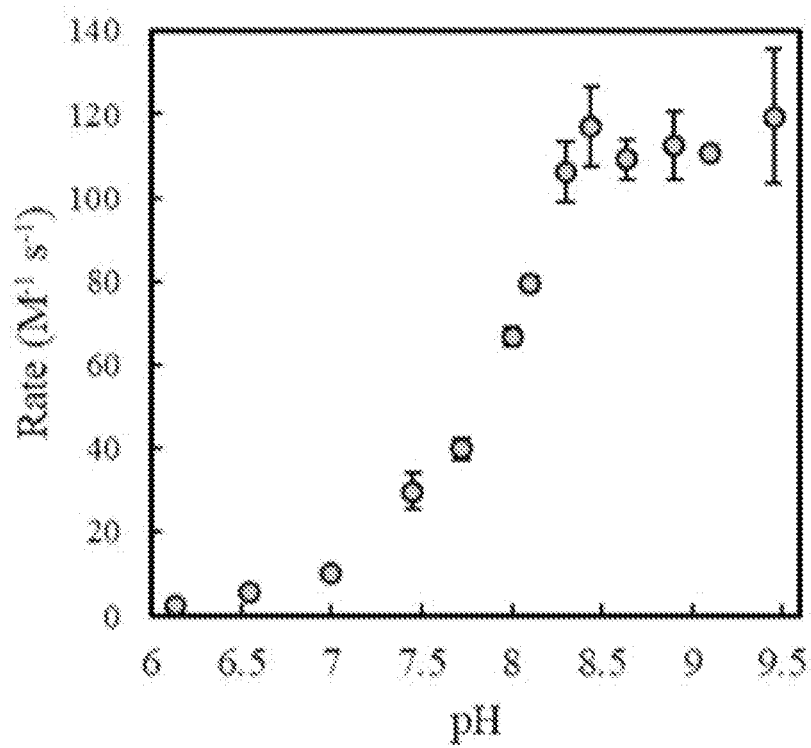
FIG. 17 shows second order rate constants of an exemplary miniprotein (Gen4) at various pH values.

MP01-Gen4 (SEQ ID NO: 133) exhibited pH dependent kinetics. Profiling the reaction rate versus pH showed a roughly sigmoidal curve with a midpoint near pH 8 (FIG. 17). Without being bound by any theory, this may, indirectly, suggest that the $pK_a$ of the active cysteine is not significantly altered from that of a typical cysteine. Furthermore, this data is consistent with a thiolate acting as the nucleophile in the reaction.

Kinetics measurements using varying pH values were conducted in a similar manner except the buffer (HEPES) was switched for an alternative buffer for different pH ranges: pH 6-6.5 used 2-(N-morpholino)ethanesulfonic acid (MES), pH 7-8 used HEPES, pH 8-9 used [tris(hydroxymethyl)methylamino]propanesulfonic acid (TAPS) and pH 9-9.5 used N-cyclohexyl-3-aminopropanesulfonic acid (CAPS).

Point Mutations of Miniproteins

Alanine Scan of MP01

Figure 18:
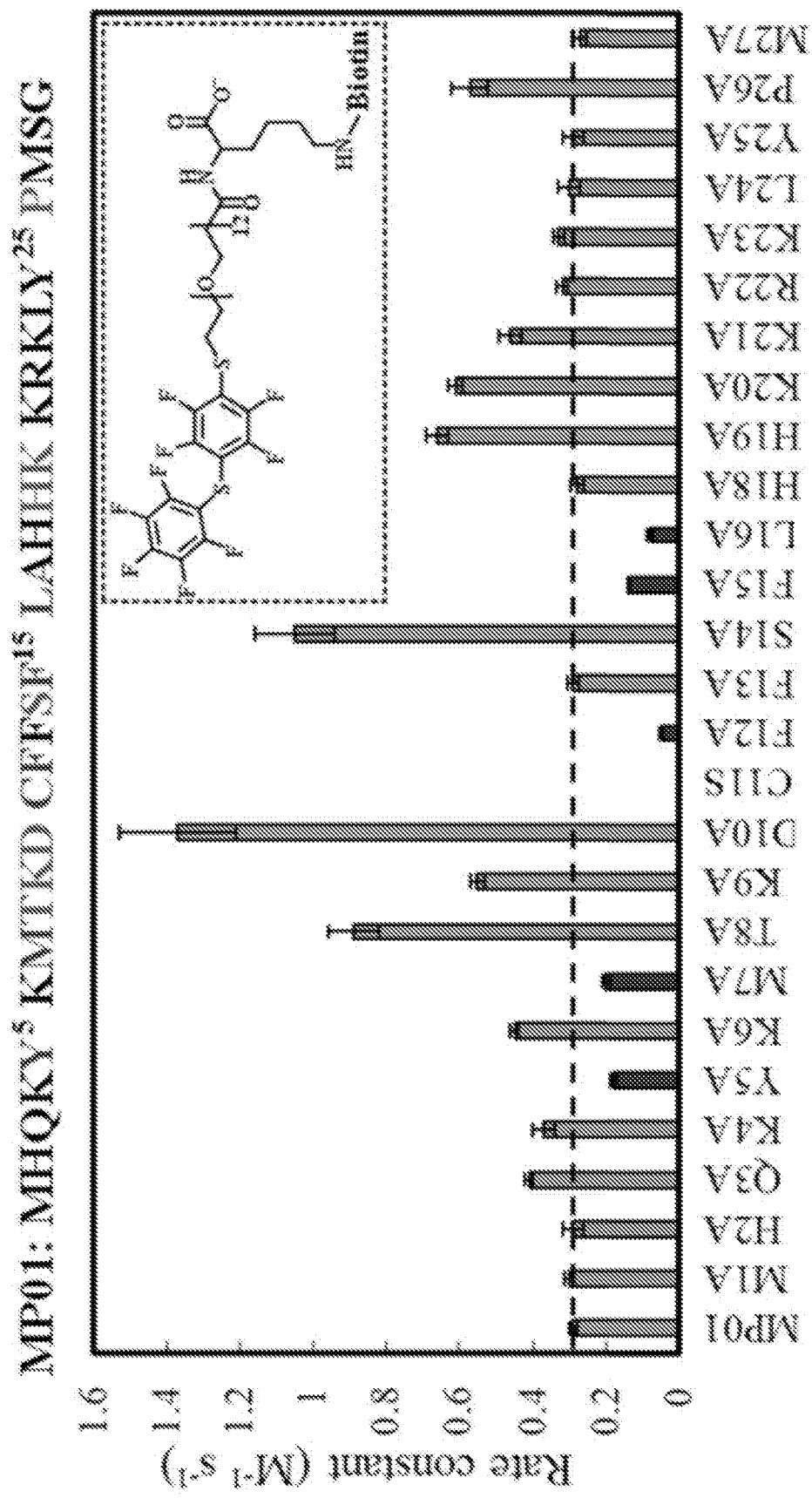
FIG. 18 shows second order rate constants of exemplary miniproteins as bars (MP01, SEQ ID NO: 13, and an alanine scan, SEQ ID NOs: 83-89, 12, 90, 64, 91-93, 63, and 94-105, respectively, in order of appearance from left to right).

To locate residues important for MP01's reactivity, an alanine scan was performed. This uncovered several residues that either helped or hindered reactivity (FIG. 18). Kinetics measurements were made on individual peptides that were chemically synthesized using an automated flow synthesizer[62], purified and then reacted using 0.1 mM peptide, 0.5 mM perfluoroaromatic probe (referred to as CA, FIG. 18 inset), 5 mM tris(2-carboxyethyl)phosphine (TCEP) and 1× selection buffer at room temperature (see Example 3, these are referred to as standard reaction conditions). The residues critical for full reactivity with the perfluoroaromatic probe were predominantly hydrophobic in nature and were concentrated within six residues of the active site cysteine. When the cysteine itself was mutated to serine (SEQ ID NO: 91), all reactivity was lost. Apart from these residues, the majority of the sequence appeared tolerant to alanine substitution. Several sites benefited from Ala substitution, suggesting that the most reactive version of MP01 had yet to be found. These beneficial mutations enhanced the rate constant from between ~1.9 to 4.7-fold and appeared both close to and far from the active cysteine in primary sequence as evident by the H19A and P26A mutations. Additionally, the properties of the residues varied from charged and polar to the rigid proline, providing little insight into their mechanism of action.

Targeted Alteration of MP01

Figure 19:
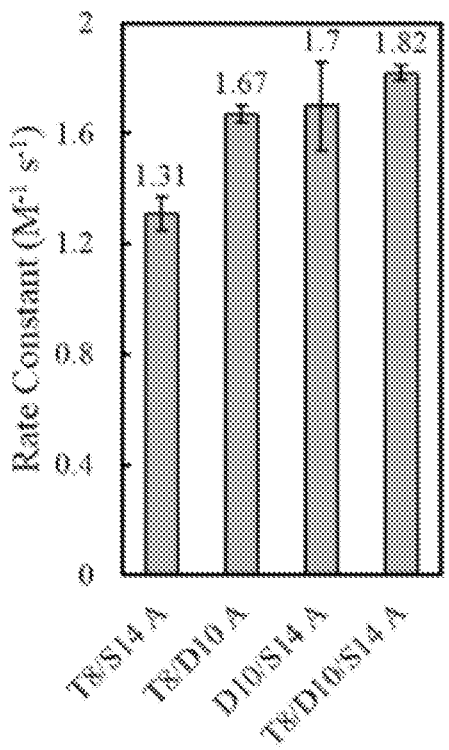
FIG. 19 shows second order rate constants of exemplary miniproteins with various alanine point mutations.

Following up on the most beneficial Ala mutants (T8, D10, S14), their synergy was tested in an attempt to understand how removing sidechain functionality during the alanine scan improved reactivity. Each combination of double mutants showed improvement, leading to the triple alanine variant with a 1.82 $\mu M^{-1} s^{-1}$ second order rate, representing a 6.3-fold increase in reactivity (FIG. 19). To gain insight on this improved reactivity, structure prediction was used. Analyzing the population changes between MP01 (SEQ ID NO: 13) and its three alanine variant (SEQ ID NO: 69) suggested a large structural landscape change. In addition to the alteration, the structural landscape may have been expanded in terms of the number of populated clusters. The major family from MP01 heavily decreased (−23.2%) with minimal alteration to its average energy while several other families both heavily increased in size and decreased in average energy (cluster-C5 for example which increased by 11.7% and decreased by 1.8 REU). In addition to potentially altering the structural landscape accessible, these mutations may have removed the steric hindrance supplied by their bulkier predecessors, improving the ability of the perfluoroaromatic to access the cysteine. Furthermore, the anionic D10 may also have destabilize the anionic Meisenheimer complex.

Figure 20:
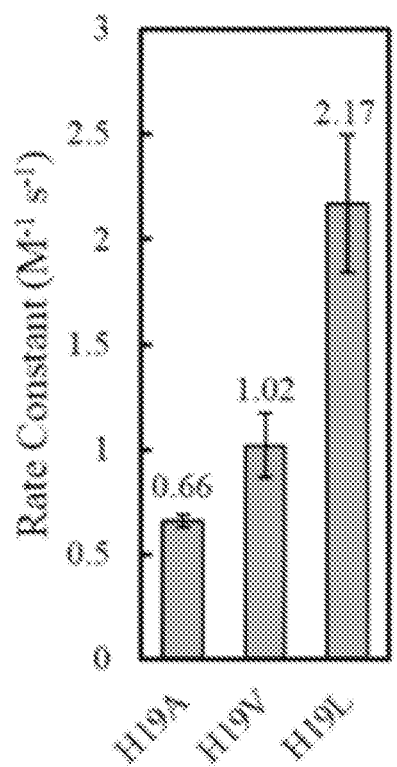
FIG. 20 shows second order rate constants of exemplary miniproteins with various H19 variants.

Merging insight on the spatial context of H19 from modeling with the experimentally beneficial H19A mutant led to an H19L mutation with a 7.5-fold increased rate constant. The spatial location of both H19 and its A mutant in reference to the critical F15 and L16 suggested that this location may benefit from placement of larger hydrophobic residues (V and L) to stabilize this interaction. Under a model that placed importance on an alpha helix, stabilization of this feature was believed important to affect change in reactivity. In line with this notion, without being bound by any theory, the chemically synthesized H19V and L mutations both showed progressively improved rate constants (FIG. 20). Population level analysis showed that while the primary family from MP01 remained dominant and its average energy decreased (−2.69 REU) in the H19L variant's landscape, its size slightly decreased (−5.19%). At the same time, the ordering and energies of the secondary families changed with a notable increase size of cluster H19L cluster-C3 that increased by 8.34% with −0.75 REU.

Figure 21:
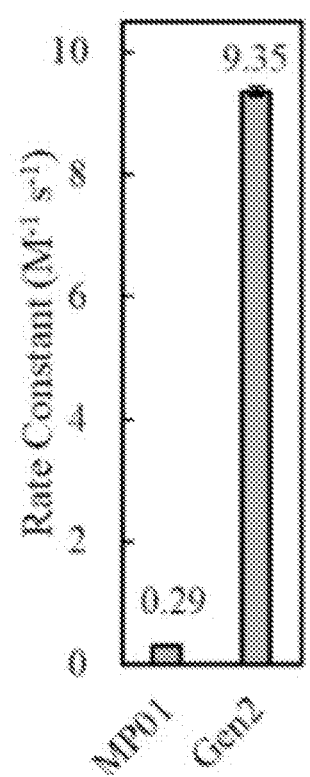
FIG. 21 shows second order rate constants of exemplary miniproteins with various point mutations.
Figure 22:
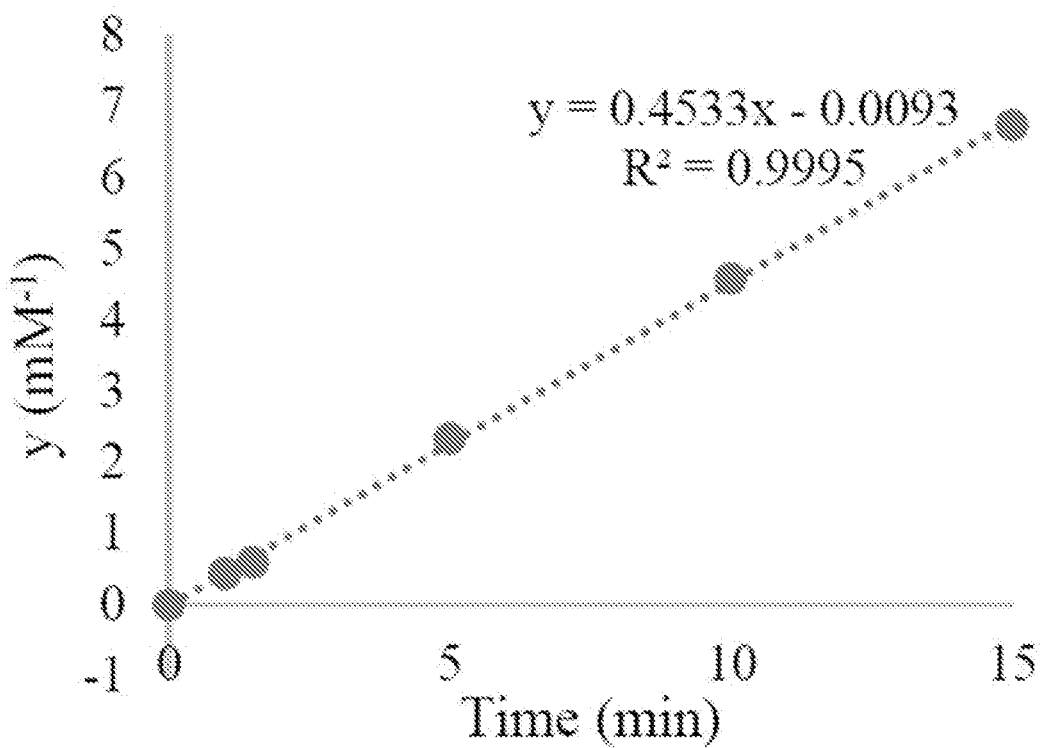
FIG. 22 shows the plot of integrated TIC peak area to determine a second order rate constant for the kinetic analysis of MP01 Gen2 Q3A.
Figure 23:
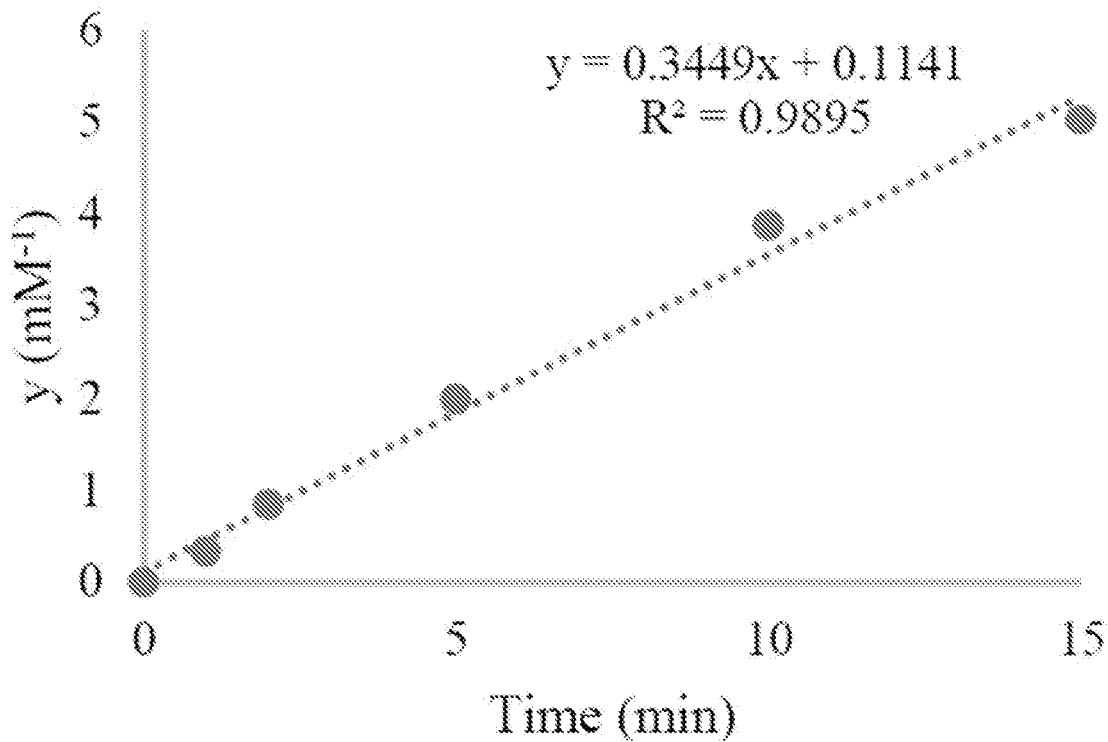
FIG. 23 shows the plot of integrated TIC peak area to determine a second order rate constant for the kinetic analysis of MP01 Gen2 K9A.
Figure 24:
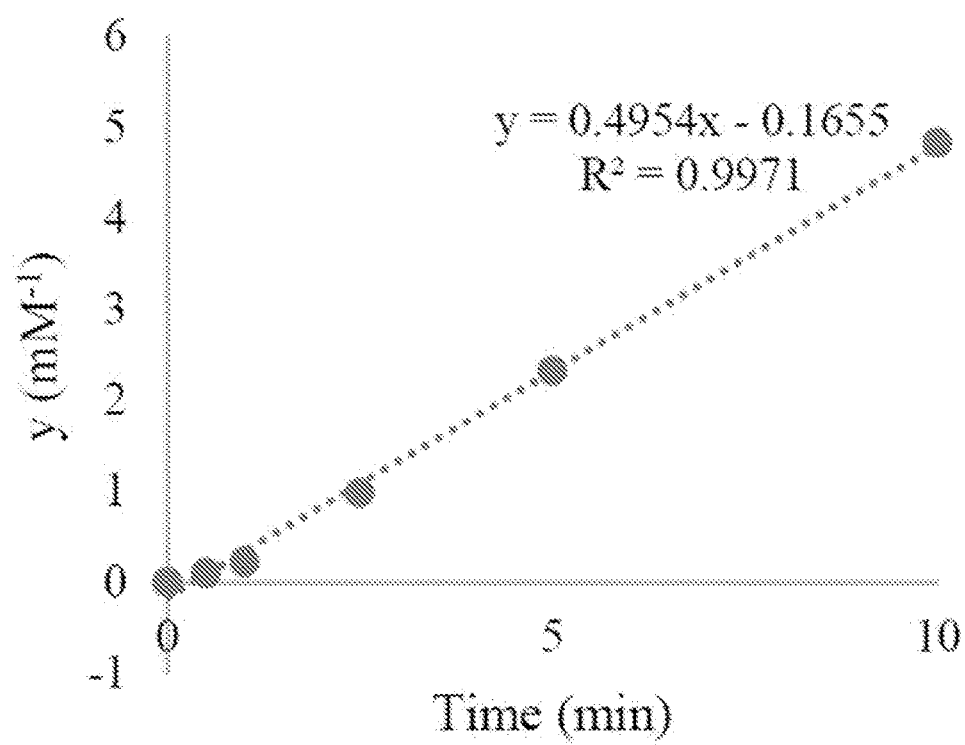
FIG. 24 shows the plot of integrated TIC peak area to determine a second order rate constant for the kinetic analysis of MP01 Gen2 K20A.

To determine whether the 3A variant (SEQ ID NO: 69) would synergize with the H19L mutation (SEQ ID NO: 62) a combined, four residue altered sequence (MP01-Gen2; SEQ ID NO: 71) was synthesized. This sequence afforded a 32.2-fold improved second order rate constant relative to MP01 (SEQ ID NO: 13) and was superior to a 4 Ala variant where H19 was replaced with an Ala (SEQ ID NO: 70) (FIG. 21). Computational modeling suggests that this peptide adopts features from both the H19L and 3A variants with a broad landscape of clusters with similar energies. Here, the major family from all previous structures has been replaced by a higher energy family (Gen2 cluster C2); however, the energetically more favorable families still appear at significant percentages. Additionally, none of the representative structures displayed a significant folding funnel or drastically decreased energy suggesting yet again that this sequence may have access to multiple states and possibly transition between states. Attempts to combine additional beneficial alanine point mutants with the Gen2 scaffold yielded no alteration (Q3A, K9A and K20A for example, FIGS. 22-24).

Figure 25:
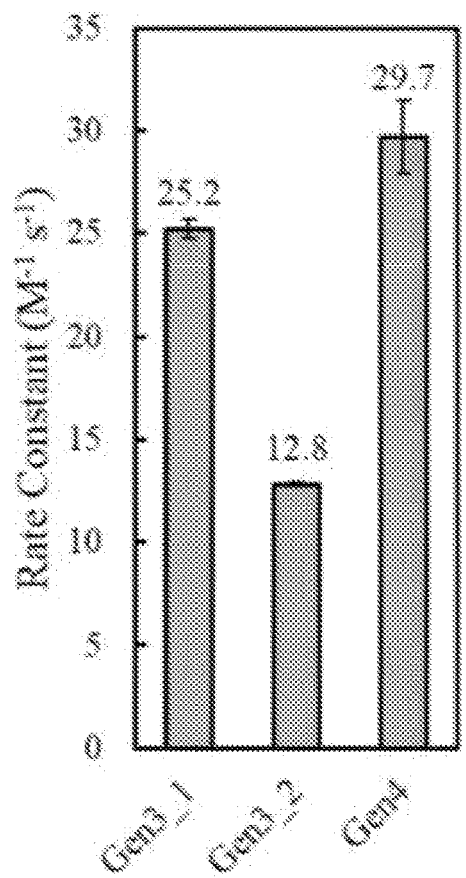
FIG. 25 shows the plot of integrated TIC peak area to determine a second order rate constant for the kinetic analysis of exemplary miniproteins (Gen3 and Gen4).
Figure 26:
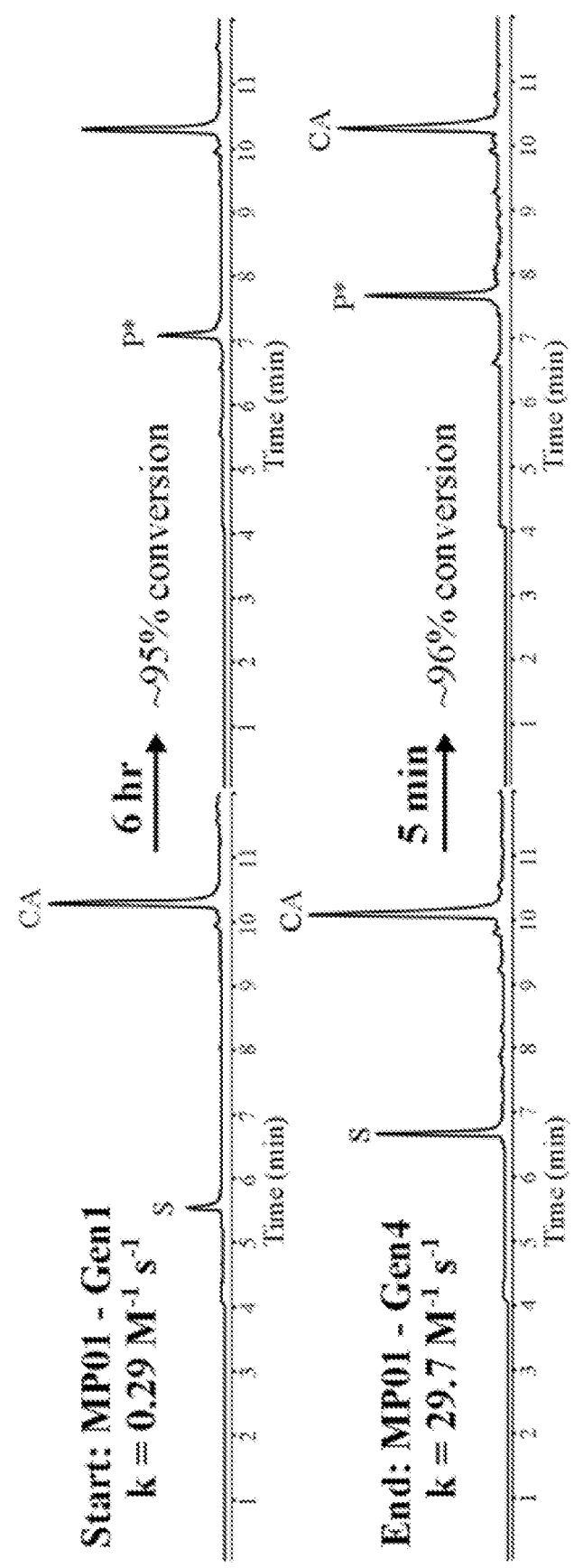
FIG. 26 shows LCMS conversion analysis and rate constant comparison between the starting peptide (MP01-Gen1) and the final peptide (MP01-Gen4).

Attempting to stabilize specific structural elements seen throughout Gen2's landscape led to a sequence possessing a second order rate constant ~100 times greater than the initial MP01 scaffold. Gen2's A17 almost always appeared in an alpha helix three and four residues prior to a positively charged amino acid (K20/21) the structure of which could be stabilized by an i, i+4 salt bridge. Furthermore it was noted that H2 may be involved in capping the N-terminal portion of a helix that could similarly be stabilized by an asparagine residue. Producing both of these variants (Gen3_1 for A17E (SEQ ID NO: 116) and Gen3_2 for H2N (SEQ ID NO: 121)) again each individually increased the rate of reaction with the CA, with a striking improvement provided by the A17E mutant (FIG. 25). Once again, combining these two alterations synergized, delivering the final MP01-Gen4 sequence (SEQ ID NO: 133) with six positions altered that is significantly more reactive than its progenitor scaffold (MP01 (SEQ ID NO: 13)) and ~4×10$^3$ times more reactive than a random cysteine containing peptide (previously measured at 0.007 $\mu M^{-1}$ $s^{-1}$). A modified miniprotein delivered high conversion in minutes rather than hours (FIG. 26). Structural landscape modeling of Gen2 to Gen4 suggested a broad conformational space and no significant folding funnels for any of the representative structures. While the mutations may have stabilized interactions, possibly helping the sequence adopt a reactive conformation, the overall conformational space is still predicted to be broad and similar in energy, so it was not expected to adopt a single form.

Labeling Site Determination

To determine the location of labeling for MP01, 07 and 10 reactions were made using 0.3 mM MP, 0.3 mM CA, 1× selection buffer, 5 mM TCEP pH 7.4 and reacted 24 hours for MP01 and 5 hours for MP07 and 10. Next the peptides were digested with 0.2 mg/mL trypsin and chymotrypsin (0.1 mg/mL for MP10) for 24 hours at 37° C. Fragments were then analyzed by LC-MS/MS of an Agilent 6550 iFunnel Q-TOF mass spectrometer. Similarly, the CA by itself was analyzed with the same LC-MS/MS protocol.

Example 5: Protein Expression and Purification

To investigate two singly labeled MPs for regioselective bioconjugation, N-terminal fusions of MP01 or MP10-Sortase A (SrtA) were expressed from *E. Coli*. SrtA is a transpeptidase with an active site cysteine nucleophile necessary for catalysis.[63] The two MP-SrtA proteins were independently reacted at 10 μM with 1 mM CA in a solution of 5 mM TCEP and 1× selection buffer, pH 8 at RT for four hours. LC-MS analysis of the crude reaction mixtures showed a 95% and 87% reaction yield for MP01- and MP10-SrtA respectively. Apparently once attached to a larger biomolecule, MP10 no longer reacts as rapidly as it does alone in solution; possibly suggesting why its sequence count was dwarfed by MP01, as MP01 retained its full reactivity when linked to SrtA.

To determine the location of the CA in the labeled MP-SrtA fusions, Tobacco Etch Virus (TEV) protease was used to cleave the TEV motif implanted between the MP and SrtA. For TEV cleavage, the following conditions were used 3 μM MP-SrtA, 0.02 mg mL$^{-1}$ TEV protease, 300 mM phosphate pH 6.0, 1 mM DTT, 24 hours, RT. Following 24 hour cleavage, LC-MS analysis revealed the presence of unlabeled SrtA for both MP constructs along with the desired product mass for both labeled miniproteins. LC-MS analysis was performed using method 3 with the MS turned off at 11 minutes to avoid over saturating the MS detector with CA. Alternatively, LC-MS analysis was performed using method 1 with the MS turned off at 10 minutes to avoid over saturating the MS detector with CA.

To orthogonally verify that the active-site cysteine of SrtA had not been labeled, both 4 hour reacted and unreacted MP-SrtAs were assayed for SrtA activity. Using 250 μM of a G5 nucleophile (S-pep-2), 50 μM YALPSTGG (SEQ ID NO: 185) (S-pep-1), 10 mM CaCl$_2$, 5 μM SrtA conjugate (either from a 4 hour CA reaction or unreacted), the integrated area for the reaction product following 1 hour was comparable for labeled and unlabeled constructs, supporting the observation that the MPs were labeled and the active site SrtA cysteine was unchanged. S-pep-1 and s-pep-2 were chosen because they were known to be good substrates for the Sortase enzyme with good chromatographic behaviour.

Full length MP01 and MP10 were appended to the sequence of Sortase A (with a TEV cleavage between the two) and then placed into a pET-SUMO vector (Thermo Fisher) following factory protocols. Expression was performed in 1 L cultures (30 μg/mL kanamycin) of appropriately transformed *E. Coli* BL21(DE3), after an O.D. value of 0.5 was obtained upon at 37° C., the cultures were cooled to 16° C. and induced with the addition of 0.2 or 0.4 mM IPTG (MP01 or MP10). Expression was conducted for 5.5 hours at 16° C. (MP01) or overnight at 18° C. (MP10) followed by cell pelleting with 10 minute centrifugation at 7,000 RPM. The cell pellet was suspended in 25 mL of Ni-NTA binding buffer (50 mM Tris pH 8.1 150 mM NaCl) with one protease inhibitor cocktail tablet (Roche Diagnostics, Switzerland), 20 mg lysozyme (Calbiochem) and ~2 mg DNase I (Sigma-Aldrich). Following sonication the cellular debris was removed by centrifugation at 17,000 RPM for 30 minutes. The supernatant was loaded directly onto a 5 mL HisTrap FF crude Ni-NTA column (GE Healthcare, UK), following binding the column was washed with 25 mL Ni-NTA binding buffer, 25 mL Ni-NTA washing buffer (50 mM Tris pH 8.1, 150 mM NaCl, 500 mM imidazole) and eluted with 10 mL of Ni-NTA elution buffer (50 mM Tris pH 8.1, 150 mM NaCl, 500 mM imidazole). The proteins were then desalted on a HiPrep 26/10 Desalting Column (GE Healthcare, UK). Following concentrating, the SUMO group was removed by addition of 30 µg of SUMO protease per mg of protein at 4° C. overnight.

MP01-SrtA and MP10-SrtA was further purified by anion exchange chromatography after being exchanged into buffer A (20 mM HEPES pH 8.5, 1 mM DTT) for MP01-SrtA or buffer A' (20 mM HEPES pH 7.8, 20 mM NaCl, 2 mM DTT). MP01-SrtA was loaded onto a HiTrap Q HP column (GE Healthcare, UK) in buffer A and eluted with buffer B (buffer A+2 µM NaCl) during a 400 mL linear gradient from 0-30% B. MP10-SrtA, on the other hand, was loaded onto a HiTrap Capto S cation exchange column (GE Healthcare, UK) and eluted with buffer B' (A'+1 µM NaCl) in a 400 mL gradient to 40% B'. Fractions for the respective proteins were combined and concentrated on a 10K spin filter and buffer exchanged into 0.5× selection buffer. The concentrations were determined spectrophotometrically using 280 nm light and extinction coefficients obtained from the ProtParam tool on web.expasy.org and a sample was taken for LCMS analysis. Both proteins were aliquoted and flash frozen in liquid nitrogen.

```
SUMO-MP01-SrtA (Calc. 36473.84).
MP01-SrtA (Calc. 23075.6, underlined):
                                         (SEQ ID NO: 194)
MGSSEIREIHHHGSGLVPRGSASMSDSEVNQEAKPEVKPEVKPETHINLK

VSDGSSEIFFKIKKTTPLRRLMEAFAKRQGKEMDSLRFLYDGIRIQADQT

PEDLDMEDNDITEAHREQIGGMHQKYKMTKDCFFSFLAHHKKRKLYPMSG

SGSLGHEIRREIHRLGENLYFQGGDPNSQAKPQIPKDKSKVAGYIEIPDA

DIKEPVYPGPATSEQLNRGVSFAEENESLDDQNISIAGHTFIDRPNYQFT

NLKAAKKGSMVYFKVGNETRKYKMTSIRNVKPTDVEVLDEQKGKDKQLTL

ITCDDYNEKTGVWETRKIFVATEVK

SUMO-MP10-SrtA (Calc. 36642.0), MP10-SrtA
(Calc. 23243.76, underlined):
                                         (SEQ ID NO: 195)
MGSSHREIFIREIGSGLVPRGSASMSDSEVNQEAKPEVKPEVKPETHINL

KVSDGSSEIFFKIKKTTPLRRLMEAFAKRQGKEMDSLRFLYDGIRIQADQ

TPEDLDMEDNDITEAHREQIGGMHNAYLRKSMRQLCYFRRTLHNIFIVMS

HRGSGSLGHEIRREIHRLGENLYFQGGDPNSQAKPQIPKDKSKVAGYIEI

PDADIKEPVYPGPATSEQLNRGVSFAEENESLDDQNISIAGHTFIDRPNY
```
-continued
```
QFTNLAAKKGSMVYFKVGNETRKYKMTSIRNVKPTDVEVLDEQKGKDKQL

TLITCDDYNEKTGVWETRKIFVATEVK
```

Example 6: Rosetta Structure Prediction and Clustering

For each sequence the following general protocol was followed:
1. launch 100 of the following, general Rosetta protocol (40,000 total predictions):
AbinitioRelax.default.linuxgccrelease-in:file:fasta./seq_name.fasta-in:file:frag3./aat000_03_05_name.200_v1_3-in:file:frag9./aat000_09_05_name.200_v1_3-abinitio:relax-dump-connect_info-connect_info_cutoff0-use_truncated_termini false-nstruct400-out:file:silent./name.silent-out:path/out/file/path/-relax::fast-abinitio::increase_cycles10-abinitio::rg_reweight0.5-abinitio::rsd_wt_helix0.5-abinitio::rsd_wt_loop 0.5-use_filters true-psipred_ss2./t000_name.psipred_ss2-kill hairpins./t000_name.psipred_ss2
2. Following the structure prediction, the output file would be cleaned to remove any lines that could not be handled by the clustering program (lines when the .silent file was being written to by multiple copies of the same program). The following protocol would then be run to generate the true clustering input (this clustering protocol was not actually used to supply any information to the actual clustering program, it simply got the input in the correct form):
cluster.linuxgccrelease-in:file:silent./path/to/file/file.silent-in:file:fullatom-out:file:silent./out/path/clustered_name.silent-cluster:radius-1-score:weights score3
3. All of the pdb files were released with the following and moved into their own directory:
extract_pdbs.linuxgccrelease-in:file:fullatom-in:file:silent./clustering_file.silent
4. These were then clustered with a custom program (single batch_full_cluster.sh on the github page below) that performed k-means clustering where k=40. This program used pymol for structure alignment and is easily customizable to cluster based on subsequences in the structure. This program is available via a github page[64]. This program was customized for a 64 core compute node using a Slurm job manager but can easily be tuned for alternative workstations. Generally, it launches a program that assigns a data chunk (structures to be assigned to a center) to each cpu along with the current centers. Each chuck is then independently clustered and each clustering program writes its output. Then a center update program is launched to update the means and the process repeated. This gives a number of useful outputs including: pdb files of the cluster centers (these are average structures so atom placement may be nonsensical but strong structural elements of clusters are visually quite apparent), a file concerning the amount the centers moved in a given cycle, a file of text mapping the center structure to the size of its cluster, another file mapping (for each cycle) the center to a list of all pdbs in the cluster (used for energy analysis later on).
5. Next, the individual structural averages were clustered because due to initial starting conditions two (or more) clusters may actually be the 'same'. To accomplish this, the 40 centers were hierarchically clustered using the cluster_means_2.sh script. To visualize this result required the following two pieces of data: the resulting pickle file from the cluster_means_2 script along with a *.txt file containing the dictionary of the final rounds' center-to-cluster size (taken from the final dictionary of the clusters_new.txt file generated from the clustering program). Visualization was then performed with plot_dendrogram.py to make a dendrogram of the centers.

6. Further visualization and sequence-to-sequence analysis was performed using heatmaps. To make a heatmap, all center distances (for either the same sequence or two different sequences) were calculated with the two_structure_distance.sh script. This script is used by providing the path to the two directories containing the centers (note only the centers should be in this directory) along with the output files generated by the plot_dendrogram.py program. The distance pickle file is then plotted with plot_heatmap.py 7. Manual inspection of the dendrogram and heatmap allow for cluster family determination as typically many clusters actually represent the same overall structure. Once families are determined, structures that best represent the family are chosen by energy and root mean square deviation (RMSD) analysis.

8. Energy analysis is performed with the energy_analysis.sh program. Generally, this script takes a text file that lists all the centers that represent a given structure for each family and outputs the energy and in family RMSD between the five lowest energy structures in each cluster and the rest of the family. In the following example there are two families where the first family is represented by center_1 and 2 from the initial clustering and family two was represented by a single center. Thus this program would located the 5 lowest energy structures for center_1, 2 and 3 and calculate the in family RMSD for each—so 10 possible structures for family 1 and five for family 2.

Example
   Center 1, center_2
   Center 3
   This program would then also release the .pdbs for each of the structures analyzed (15 in total here) and a summary csv file.

9. Following this analysis the best representative structures were determined by a combination of lowest energy and smallest in family RMSD (with this taking precedence).

In an attempt to rationalize the Ala scan results, Rosetta ab initio structure prediction was used to model MP01. These models are only used to lend molecular insight and guide experimental design, not to assign an absolute conformation. Structure clustering suggested a dominant family with several smaller, but similar neighbors. Representative structures were extracted from each family using a combination of low in-cluster energy and low in-cluster root mean square deviation (RMSD). The predominant family accounted for 45.9% of structures and possessed the lowest average Rosetta energy (REU); however, the energy difference between it and those of other clusters was minimal. This slight energy difference, along with the lack of a defined folding funnel for any of the representative structures suggested that this sequence may be structurally flexible and lack a defined conformation or that the minima wasn't sampled or scored properly. Lacking biophysical data to select just one conformation as our model, a multistate modeling approach was adopted to understand this sequence and its variants with the hypothesis that these predicted states or states similar to them may still be partially populated. The landscape predominantly suggested random coils flanking both sides of an alpha helix that possessed the active cysteine in its N-terminal region. Without being bound by any theory, sidechain-based activation of the cysteine is not believed to predominate due to minimal decreased reactivity for nearly all polar and charged residue-to-alanine mutants (H2, K4, K6, T8, K9, D10, S14, H18, H19 and K20). Structure-based activation (through a macromolecular dipole) along with small molecule-induced activation could not be ruled out as several residues that are predicted in hydrophobic interactions (which may stabilize a reactive conformation or interact with the CA) were necessary for reactivity.

Here the properties of a midsized peptide were examined with a particular interest in their effect on its reactivity. These features spanned from the effects of individual residues to structural considerations and substrate interactions. At the residue level, it appeared that select hydrophobic residues were critical for reaction, while many other sites could be mutated to alanine with marginal or beneficial change. Mixing insights from structural landscape modeling with residue mutagenesis, the properties of this sequence were improved. These believed residue-to-structural level effects suggested a flexible peptide. Importantly, through these studies it was found that residues distant from the reactive cysteine in primary sequence, as well as predicted to be spatially distant, could significantly alter the peptides' reactivity. Without being bound by any theory, it was hypothesized that the effects of these mutations alter MP01's structural landscape or its ability to interact with the CA. This peptide also showed sensitivity to truncation and denaturant addition, both of which had important, and detrimental consequences. Ultimately this uncovered that the peptide alters its structure in response to the small molecule probe, even under noncovalent conditions.

The use of structural modeling and landscape analysis was beneficial but must also be carefully considered in view of the length of the miniproteins. The modeling helped locate several mutations that were not obvious given only the amino acid sequence. Most notable of these was the A17E mutation. Given such a short sequence and the experimentally observed CD spectra, the unlabeled MP01 might actually display significantly more random-coil behavior than predicted. The modeling is useful to think about the possible accessible states, not necessarily representative of all states.

MP01 supports the notion that function can be achieved without possessing a single native conformation. In this regard, MP01-Gen4 is reminiscent of intrinsically disordered proteins that undergo disorder-to-order transitions upon performing their function[65-67] Without being bound by any theory, the observed conformation change of MP01-Gen4 upon binding to the CA may be driven by an interaction (akin to an induced fit mechanism). Alternatively, without being bound by any theory, the CA may act as more of a conformation selection probe that binds to a given subpopulation of MP01 structures, thus, stabilizing the structure.

REFERENCES CITED (1) Sletten, E. M.; Bertozzi, C. R. *Angew. Chem. Int. Ed.* 2009, 48 (38), 6974.
(2) Spicer, C. D.; Davis, B. G. *Nat. Commun.* 2014, 5, 4740.
(3) Blackman, M. L.; Royzen, M.; Fox, J. M. *J. Am. Chem. Soc.* 2008, 130 (41), 13518.

(4) Saxon, E.; Bertozzi, C. R. *Science* 2000, 287 (5460), 2007.
(5) Agard, N. J.; Prescher, J. A.; Bertozzi, C. R. *J. Am. Chem. Soc.* 2004, 126 (46), 15046.
(6) Rostovtsev, V. V.; Green, L. G.; Fokin, V. V.; Sharpless, K. B. *Angew. Chem. Int. Ed.* 2002, 41 (14), 2596.
(7) Fernandez-Suarez, M.; Baruah, H.; Martinez-Hernandez, L.; Xie, K. T.; Baskin, J. M.; Bertozzi, C. R.; Ting, A. Y. *Nat. Biotechnol.* 2007, 25 (12), 1483.
(8) Popp, M. W.; Antos, J. M.; Grotenbreg, G. M.; Spooner, E.; Ploegh, H. L. *Nat Chem Biol* 2007, 3 (11), 707.
(9) Chen, I.; Howarth, M.; Lin, W.; Ting, A. Y. *Nat Meth* 2005, 2 (2), 99.
(10) Los, G. V.; Encell, L. P.; McDougall, M. G.; Hartzell, D. D.; Karassina, N.; Zimprich, C.; Wood, M. G.; Learish, R.; Ohana, R. F.; Urh, M.; Simpson, D.; Mendez, J.; Zimmerman, K.; Otto, P.; Vidugiris, G.; Zhu, J.; Darzins, A.; Klaubert, D. H.; Bulleit, R. F.; Wood, K. V. *ACS Chem. Biol.* 2008, 3 (6), 373.
(11) Keppler, A.; Gendreizig, S.; Gronemeyer, T.; Pick, H.; Vogel, H.; Johnsson, K. *Nat. Biotechnol.* 2002, 21 (1), 86.
(12) Chen, Z.; Jing, C.; Gallagher, S. S.; Sheetz, M. P.; Cornish, V. W. *J. Am. Chem. Soc.* 2012, 134 (33), 13692.
(13) Zhang, C.; Welborn, M.; Zhu, T.; Yang, N. J.; Santos, M. S.; Van Voorhis, T.; Pentelute, B. L. *Nat. Chem.* 2016, 8, 120.
(14) Wilson, C.; Szostak, J. W. *Nature* 1995, 374 (6525), 777.
(15) Sharma, A. K.; Plant, J. J.; Rangel, A. E.; Meek, K. N.; Anamisis, A. J.; Hollien, J.; Heemstra, J. M. *ACS Chem. Biol.* 2014, 9 (8), 1680.
(16) McDonald, R. I.; Guilinger, J. P.; Mukherji, S.; Curtis, E. A.; Lee, W. I.; Liu, D. R. *Nat. Chem. Biol.* 2014, 10 (12), 1049.
(17) Lim, R. K. V.; Li, N.; Ramil, C. P.; Lin, Q. *ACS Chem. Biol.* 2014, 9 (9), 2139.
(18) Kawakami, T.; Ogawa, K.; Goshima, N.; Natsume, T. *Chem. Biol.* 2015, 22 (12), 1671.
(19) Cochran, A. G.; Skelton, N. J.; Starovasnik, M. A. *Proc. Natl. Acad. Sci.* 2001, 98 (10), 5578.
(20) Zondlo, N. J.; Schepartz, A. *J. Am. Chem. Soc.* 1999, 121 (29), 6938.
(21) Struthers, M. D.; Cheng, R. P.; Imperiali, B. *Science* 1996, 271 (5247), 342.
(22) Dahiyat, B. I.; Mayo, S. L. *Science* 1997, 278 (5335), 82.
(23) Oldfield, C. J.; Dunker, A. K. *Annu. Rev. Biochem.* 2014, 83 (1), 553.
(24) Blow, D. M.; Birktoft, J. J. & Hartley, B. S. Role of a Buried Acid Group in the Mechanism of Action of Chymotrypsin. *Nature* 221, 337 (1969).
(25) Villa, J. & Warshel, A. Energetics and Dynamics of Enzymatic Reactions. *J. Phys. Chem. B* 105, 7887-7907 (2001).
(26) PAULING, L. Nature of Forces between Large Molecules of Biological Interest*. *Nature* 161, 707 (1948).
(27) Jencks, W. P. Binding Energy, Specificity, and Enzymic Catalysis: The Circe Effect. in *Advances in Enzymology and Related Areas of Molecular Biology* (ed. Meister, A.) 219-410 (John Wiley & Sons, Inc., 1975).
(28) Warshel, A. et al. Electrostatic Basis for Enzyme Catalysis. *Chem. Rev.* 106, 3210-3235 (2006).
(29) Estell, D. A. et al. Probing Steric and Hydrophobic Effects on Enzyme-Substrate Interactions by Protein Engineering. *Science* 233, 659-663 (1986).
(30) Rucker, V. C. & Byers, L. D. An Assessment of Desolvation on Rates of Acetyl Transfer: Insights into Enzyme Catalysis. *J. Am. Chem. Soc.* 122, 8365-8369 (2000).
(31) Hammes, G. G. Multiple Conformational Changes in Enzyme Catalysis. *Biochemistry (Mosc.)* 41, 8221-8228 (2002).
(32) Tsou, C. L. Conformational flexibility of enzyme active sites. *Science* 262, 380-381 (1993).
(33) Agarwal, P. K., Billeter, S. R., Rajagopalan, P. T. R., Benkovic, S. J. & Hammes-Schiffer, S. Network of coupled promoting motions in enzyme catalysis. *Proc. Natl. Acad. Sci.* 99, 2794-2799 (2002).
(34) Chao, F.-A. et al. Structure and dynamics of a primordial catalytic fold generated by in vitro evolution. *Nat. Chem. Biol.* 9, 81 (2013).
(35) An enzymatic molten globule: Efficient coupling of folding and catalysis. Available at: http://www.pnas.org/content/101/35/12860.abstract. (Accessed: 7 Dec. 2017)
(36) Palombo, M. et al. The relationship between folding and activity in UreG, an intrinsically disordered enzyme. *Sci. Rep.* 7, 5977 (2017).
(37) Canfield, R. E. The Amino Acid Sequence of Egg White Lysozyme. *J. Biol. Chem.* 238, 2698-2707 (1963).
(38) HARTLEY, R. W. & BARKER, E. A. Amino-acid Sequence of Extracellular Ribonuclease (Barnase) of *Bacillus amyloliquefaciens*. *Nature. New Biol.* 235, 15 (1972).
(39) Chen, L. H. et al. 4-Oxalocrotonate tautomerase, an enzyme composed of 62 amino acid residues per monomer. *J. Biol. Chem.* 267, 17716-17721 (1992).
(40) Yu, W.-H., Huang, P.-T., Lou, K.-L., Yu, S.-S. C. & Lin, C. A smallest 6 kda metalloprotease, mini-matrilysin, in living world: a revolutionary conserved zinc-dependent proteolytic domain-helix-loop-helix catalytic zinc binding domain (ZBD). *J. Biomed. Sci.* 19, 54 (2012).
(41) Bhardwaj, G. et al. Accurate de novo design of hyperstable constrained peptides. *Nature* 538, 329-335 (2016).
(42) Rozinov, M. N. & Nolan, G. P. Evolution of peptides that modulate the spectral qualities of bound, small-molecule fluorophores. *Chem. Biol.* 5, 713-728 (1998).
(43) Hong Enriquez, R. P. et al. Designing Short Peptides with High Affinity for Organic Molecules: A Combined Docking, Molecular Dynamics, And Monte Carlo Approach. *J. Chem. Theory Comput.* 8, 1121-1128 (2012).
(44) Broo, K. S., Brive, L., Ahlberg, P. & Baltzer, L. Catalysis of Hydrolysis and Transesterification Reactions of p-Nitrophenyl Esters by a Designed Helix-Loop-Helix Dimer. *J. Am. Chem. Soc.* 119, 11362-11372 (1997).
(45) Davie, E. A. C., Mennen, S. M., Xu, Y. & Miller, S. J. Asymmetric Catalysis Mediated by Synthetic Peptides. *Chem. Rev.* 107, 5759-5812 (2007).
(46) Ramil, C. P., An, P., Yu, Z. & Lin, Q. Sequence-Specific 2-Cyanobenzothiazole Ligation. *J. Am. Chem. Soc.* 138, 5499-5502 (2016).
(47) Bradley, P., Misura, K. M. S. & Baker, D. Toward High-Resolution de Novo Structure Prediction for Small Proteins. *Science* 309, 1868-1871 (2005).
(48) Roberts, R. W.; Szostak, J. W. *Proc. Natl. Acad. Sci.* 1997, 94 (23), 12297.
(49) Williams, J. H. *Acc. Chem. Res.* 1993, 26 (11), 593.
(50) Ja, W. W.; Wiser, O.; Austin, R. J.; Jan, L. Y.; Roberts, R. W. *ACS Chem. Biol.* 2006, 1 (9), 570.
(51) Seelig, B. *Nat. Protoc.* 2011, 6 (4), 540.
(52) Heyduk, E.; Heyduk, T. *Anal. Biochem.* 2014, 464, 73.

(53) Ditzler, M. A.; Lange, M. J.; Bose, D.; Bottoms, C. A.; Virkler, K. F.; Sawyer, A. W.; Whatley, A. S.; Spollen, W.; Givan, S. A.; Burke, D. H. *Nucleic Acids Res.* 2013, 41 (3), 1873.
(54) Ameta, S.; Winz, M.-L.; Previti, C.; Jaschke, A. *Nucleic Acids Res.* 2014, 42 (2), 1303.
(55) Schtitze, T.; Wilhelm, B.; Greiner, N.; Braun, H.; Peter, F.; Morl, M.; Erdmann, V. A.; Lehrach, H.; Konthur, Z.; Menger, M.; Arndt, P. F.; Glokler, *J. PLoS ONE* 2011, 6 (12), e29604.
(56) Jalali-Yazdi, F.; Huong Lai, L.; Takahashi, T. T.; Roberts, R. W. *Angew. Chem. Int. Ed.* 2016, 55 (12), 4007.
(57) Olson, C. A.; Nie, J.; Diep, J.; Al-Shyoukh, I.; Takahashi, T. T.; Al-Mawsawi, L. Q.; Bolin, J. M.; Elwell, A. L.; Swanson, S.; Stewart, R.; Thomson, J. A.; Soh, H. T.; Roberts, R. W.; Sun, R. *Angew. Chem. Int. Ed.* 2012, 51 (50), 12449.
(58) Cho, M.; Xiao, Y.; Nie, J.; Stewart, R.; Csordas, A. T.; Oh, S. S.; Thomson, J. A.; Soh, H. T. *Proc. Natl. Acad. Sci.* 2010, 107 (35), 15373.
(59) Kurz, M.; Gu, K.; Lohse, P. A. *Nucleic Acids Res.* 2000, 28 (18), e83.
(60) Zou, Q., Bennion, B. J., Daggett, V. & Murphy, K. P. The Molecular Mechanism of Stabilization of Proteins by TMAO and Its Ability to Counteract the Effects of Urea. *J. Am. Chem. Soc.* 124, 1192-1202 (2002).
(61) Dai, P. et al. Salt Effect Accelerates Site-Selective Cysteine Bioconjugation. *ACS Cent. Sci.* 2, 637-646 (2016).
(62) Mijalis, A. J. et al. A fully automated flow-based approach for accelerated peptide synthesis. *Nat. Chem. Biol.* 13, 464-466 (2017).
(63) Ton-That, H.; Liu, G.; Mazmanian, S. K.; Faull, K. F.; Schneewind, O. *Proc. Natl. Acad. Sci.* 1999, 96 (22), 12424.
(64) Program available via a github page: https://github.com/ethanev/Structure_clustering
(65) Dunker, A. K., Brown, C. J., Lawson, J. D., Iakoucheva, L. M. & Obradovič, Z. Intrinsic Disorder and Protein Function. *Biochemistry (Mosc.)* 41, 6573-6582 (2002).
(66) Dyson, H. J. & Wright, P. E. Intrinsically unstructured proteins and their functions. *Nat. Rev. Mol. Cell Biol.* 6, 197-208 (2005).
(67) Demarest, S. J. et al. Mutual synergistic folding in recruitment of CBP/p300 by p160 nuclear receptor coactivators. *Nature* 415, 549-553 (2002).

INCORPORATION BY REFERENCE

All US and PCT patent application publications and US patents cited herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A method of conjugating a peptide, comprising:
providing an aqueous solution comprising a peptide consisting of an amino acid sequence selected from the group consisting of SEQ ID NOs: 131, 133, 136, and 138-140, or a peptide consisting of an amino acid sequence having at least 95% homology with a peptide selected from the group consisting of SEQ ID NOs: 131, 133, 136, and 138-140;
adding to the solution a reactive drug or a reactive probe; thereby covalently binding the drug or the probe to the peptide at one amino acid residue to produce a conjugated peptide.

2. The method of claim 1, wherein the peptide consists of an amino acid sequence selected from the group consisting of SEQ ID NOs: 131, 133, 136, and 138-140.

3. The method of claim 1, wherein the peptide consists of an amino acid sequence 30 having at least 95% homology with a peptide selected from the group consisting of SEQ ID NOs: 131, 133, 136, and 138-140.

4. The method of claim 1, wherein the probe is a capture agent.

5. The method of claim 4, wherein the capture agent comprises a biotin moiety.

6. The method of claim 1, wherein the probe is a fluorophore or dye.

7. The method of claim 1, wherein the probe is covalently bound to a cysteine residue.

8. A method of conjugating a fusion protein, comprising:
providing an aqueous solution comprising a fusion protein, wherein the fusion protein comprises a protein and a peptide consisting of an amino acid sequence selected from the group consisting of SEQ ID NOs: 131, 133, 136, and 138-140, or a protein and a peptide consisting of an amino acid sequence having at least 95% homology with a peptide selected from the group consisting of SEQ ID NOs: 131, 133, 136, and 138-140;
adding to the solution a reactive drug or a reactive probe; thereby covalently binding the drug or the probe to the fusion protein at one amino acid residue to produce a conjugated fusion protein.

9. The method of claim 8, wherein the peptide consists of an amino acid sequence selected from the group consisting of SEQ ID NOs: 131, 133, 136, and 138-140.

10. The method of claim 8, wherein the peptide consists of an amino acid sequence having at least 95% homology with a peptide selected from the group consisting of SEQ ID NOs: 131, 133, 136, and 138-140.

11. The method of claim 8, wherein the probe is a capture agent.

12. The method of claim 11, wherein the capture agent comprises a biotin moiety.

13. The method of claim 8, wherein the probe is a fluorophore or dye.

14. The method of claim 8, wherein the probe is covalently bound to a cysteine residue.

15. The method of claim 8, wherein the peptide is attached to the protein at the C-terminus or at the N-terminus.

16. The method of claim 8, wherein the peptide is attached to the protein at the N-terminus.

17. The method of claim 8, wherein the protein is selected from the group consisting of sortase A, c-Myc, giutathione S-transferase (GST), hemagglutinin (HA), and maltose-binding protein.

18. The method of claim 17, wherein the protein is sortase A.

19. The method of claim 8, wherein the protein is an antibody.

20. The method of claim 19, wherein the antibody is selected from the group consisting of protein A, protein G, protein A/G, and protein L.

* * * * *

SEQUENCE LISTING

```
<160> NUMBER OF SEQ ID NOS: 332

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met His Gln Lys Tyr Lys Met Thr Lys Asp Cys Phe Phe Ser Phe Leu
1               5                   10                  15

Ala His His Lys Gln Arg Lys Leu Tyr Pro Met Ser Gly
            20                  25

<210> SEQ ID NO 2
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met His Gln Lys Tyr Lys Met Thr Lys Asp Cys Phe Phe Ser Phe Leu
1               5                   10                  15

Ala His Arg Lys Lys Arg Lys Leu Tyr Pro Met Ser Gly
            20                  25
```

```
<210> SEQ ID NO 3
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met His Gln Lys Tyr Lys Met Thr Lys Asp Cys Phe Phe Pro Phe Leu
1               5                   10                  15

Ala His His Lys Lys Arg Lys Leu Tyr Pro Met Ser Gly
            20                  25

<210> SEQ ID NO 4
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met His Gln Lys Tyr Lys Met Thr Lys Asp Cys Phe Phe Ser Phe Leu
1               5                   10                  15

Ala His His Lys Met Arg Lys Leu Tyr Pro Met Ser Gly
            20                  25

<210> SEQ ID NO 5
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met His Gln Lys Tyr Lys Met Thr Lys Asp Cys Phe Phe Ser Phe Leu
1               5                   10                  15

Ala His His Arg Lys Arg Lys Leu Tyr Pro Met Ser Gly
            20                  25

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met His Gln Lys Tyr Lys Val Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 7
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Met His Arg Lys Tyr Lys Met Thr Lys Asp Cys Phe Phe Ser Phe Leu
```

Ala His His Lys Lys Arg Lys Leu Tyr Pro Met Ser Gly
            20                  25

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met His Gln Lys Tyr Lys Met Thr Lys Asp Cys Phe Phe Ser Phe Leu
1               5                   10                  15

Ala His His Lys Lys Arg Lys Leu Tyr Pro Met Gly Gly
            20                  25

<210> SEQ ID NO 9
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met His Gln Lys Tyr Lys Met Thr Lys Asp Cys Phe Phe Ser Phe Leu
1               5                   10                  15

Ala His His Lys Lys Arg Lys Ser Tyr Pro Met Ser Gly
            20                  25

<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met His Gln Lys Tyr Lys Met Thr Lys Asp Cys Phe Phe Ser Ser Leu
1               5                   10                  15

Ala His His Lys Lys Arg Lys Leu Tyr Pro Met Ser Gly
            20                  25

<210> SEQ ID NO 11
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met His Gln Lys Tyr Lys Met Thr Lys Asp Cys Phe Phe Ser Phe Leu
1               5                   10                  15

Ser His His Lys Lys Arg Lys Leu Tyr Pro Met Ser Gly
            20                  25

<210> SEQ ID NO 12
<211> LENGTH: 29
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 12

Met His Gln Lys Tyr Lys Met Ala Lys Asp Cys Phe Phe Ser Phe Leu
1               5                   10                  15

Ala His His Lys Lys Arg Lys Leu Tyr Pro Met Ser Gly
            20                  25

<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Met His Gln Lys Tyr Lys Met Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 14
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met His Arg Lys Tyr Lys Met Lys Lys Asp Cys Phe Phe Ser Phe Leu
1               5                   10                  15

Ala His His Lys Lys Arg Lys Leu Tyr Pro Met Ser Gly
            20                  25

<210> SEQ ID NO 15
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Met His Gln Lys Tyr Glu Met Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 16
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met Tyr Gln Lys Tyr Lys Met Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 17
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met His Gln Lys His Lys Met Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 18
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met His Gln Lys Tyr Lys Met Thr Glu Asp Cys Phe Phe Ser Phe Leu
1               5                   10                  15

Ala His His Lys Lys Arg Lys Leu Tyr Pro Met Ser Gly
            20                  25

<210> SEQ ID NO 19
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met His Gln Lys Tyr Lys Met Thr Arg Asp Cys Phe Phe Ser Phe Leu
1               5                   10                  15

Ala His His Lys Lys Arg Lys Leu Tyr Pro Met Ser Gly
            20                  25

<210> SEQ ID NO 20
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met His Gln Lys Tyr Lys Met Thr Lys Asn Cys Phe Phe Ser Phe Leu
1               5                   10                  15

Ala His His Lys Lys Arg Lys Leu Tyr Pro Met Ser Gly
            20                  25

<210> SEQ ID NO 21
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Met His Gln Lys Tyr Lys Ile Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 22
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met His Gln Lys Tyr Lys Met Thr Lys Asp Cys Phe Phe Ser Phe Leu
1               5                   10                  15

Ala His His Lys Lys Arg Lys Leu Tyr Pro Met Asn Gly
            20                  25

<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Met His Gln Lys Tyr Lys Met Thr Lys Asp Cys Phe Phe Ser Phe Leu
1               5                   10                  15

Ala His His Lys Lys Arg Lys Leu Tyr Pro Thr Ser Gly
            20                  25

<210> SEQ ID NO 24
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met His Gln Lys Tyr Lys Met Thr Lys Asp Cys Phe Phe Ser Phe Leu
1               5                   10                  15

Ala Tyr His Lys Lys Arg Lys Leu Tyr Pro Met Ser Gly
            20                  25

<210> SEQ ID NO 25
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Met Gln Gln Lys Tyr Lys Met Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 26
<211> LENGTH: 29
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 26

Met His Gln Lys Cys Lys Met Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 27
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Met His Gln Lys Tyr Lys Met Thr Lys Asp Cys Phe Phe Ser Phe Leu
1               5                   10                  15

Ala His His Lys Lys Arg Arg Leu Tyr Pro Met Ser Gly
            20                  25

<210> SEQ ID NO 28
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Met His Gln Lys Tyr Lys Met Thr Lys Asp Cys Phe Phe Ser Phe Leu
1               5                   10                  15

Thr His His Lys Lys Arg Lys Leu Tyr Pro Met Ser Gly
            20                  25

<210> SEQ ID NO 29
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Met His Gln Lys Tyr Lys Met Thr Lys Asp Cys Phe Leu Ser Phe Leu
1               5                   10                  15

Ala His His Lys Lys Arg Lys Leu Tyr Pro Met Ser Gly
            20                  25

<210> SEQ ID NO 30
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Met His Gln Lys Tyr Lys Met Thr Lys Asp Cys Phe Phe Ser Phe Leu
1               5                   10                  15

Ala His His Lys Lys Arg Lys Leu Tyr Pro Val Ser Gly
            20                  25
```

```
<210> SEQ ID NO 31
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Met His Gln Lys Tyr Lys Met Thr Lys Asp Cys Phe Ser Ser Phe Leu
1               5                   10                  15

Ala His His Lys Lys Arg Lys Leu Tyr Pro Met Ser Gly
            20                  25

<210> SEQ ID NO 32
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Met His Gln Lys Tyr Lys Met Thr Lys Asp Cys Phe Phe Ser Phe Leu
1               5                   10                  15

Ala His His Lys Lys Arg Lys Leu His Pro Met Ser Gly
            20                  25

<210> SEQ ID NO 33
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Arg Gln Lys Tyr Lys Met Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 34
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Met His Gln Lys Tyr Lys Met Thr Lys Asp Cys Phe Phe Ser Phe Leu
1               5                   10                  15

Ala His His Lys Lys Gly Lys Leu Tyr Pro Met Ser Gly
            20                  25

<210> SEQ ID NO 35
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35
```

Met Pro Asn Tyr Gly Pro Leu Ser Pro Ser Gln Pro Ser Arg Gly Tyr
1               5                   10                  15

Thr Phe Trp Met Val Pro Ile Trp Asp Asn Ser His Asn Ala Ala Gly
            20                  25                  30

<210> SEQ ID NO 36
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Pro Asn His Gly Pro Leu Ser Pro Ser Gln Pro Ser His Gly Tyr
1               5                   10                  15

Thr Phe Trp Met Val Pro Ile Trp Asp Asn Ser His Asn Ala Ala Gly
            20                  25                  30

<210> SEQ ID NO 37
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Pro Asn Tyr Gly Leu Leu Ser Pro Ser Gln Pro Ser His Gly Tyr
1               5                   10                  15

Thr Phe Trp Met Val Pro Ile Trp Asp Asn Ser His Asn Ala Ala Gly
            20                  25                  30

<210> SEQ ID NO 38
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Pro Asn Tyr Gly Pro Leu Ser Pro Ser Gln Pro Ser His Gly Tyr
1               5                   10                  15

Thr Phe Trp Met Val Pro Ile Trp Asp Asn Ser Ser Ala Ala Gly
            20                  25                  30

<210> SEQ ID NO 39
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Pro Asn Tyr Gly Pro Leu Ser Pro Ser Gln Pro Ser His Gly Tyr
1               5                   10                  15

Thr Phe Trp Met Val Pro Ile Trp Asp Asn Ser His Asn Ala Ala Gly
            20                  25                  30

<210> SEQ ID NO 40
<211> LENGTH: 29
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 40

Met Thr Ser Val Thr Ala Ser Leu Leu Met His Phe Cys Pro Ile Arg
1               5                   10                  15

Ala His Ile Thr Asn Lys Pro Ser Phe Asn Pro Ser Gly
            20                  25

<210> SEQ ID NO 41
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Met Thr Ser Val Thr Ala Ser Pro Leu Met His Leu Cys Pro Ile Arg
1               5                   10                  15

Ala His Ile Thr Asn Lys Pro Ser Phe Asn Pro Ser Gly
            20                  25

<210> SEQ ID NO 42
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Arg Thr Pro Ile Lys Phe Ala Pro Arg Leu Ser Gln Pro Phe Cys
1               5                   10                  15

Pro Phe Arg Lys Gln His Gln Leu His Leu His Pro Leu Ile Glu Gly
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Arg Thr Pro Ile Lys Phe Ala Pro Arg Leu Ser Gln Pro Phe Cys
1               5                   10                  15

Pro Phe Arg Lys Gln Arg Gln Leu His Leu His Pro Leu Ile Glu Gly
            20                  25                  30

<210> SEQ ID NO 44
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Met Arg Pro Cys Ala Arg Arg Asp Arg Thr Leu Trp Cys Pro Phe Asp
1               5                   10                  15

Ser Pro Ala Trp Phe Leu Leu Ser Gly Phe Ser Cys Gly
```

```
            20                  25

<210> SEQ ID NO 45
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Met Arg Pro Cys Ala Arg Arg Gly Arg Thr Leu Trp Cys Pro Phe Asp
1               5                   10                  15

Ser Pro Ala Trp Phe Leu Leu Ser Gly Phe Ser Cys Gly
            20                  25

<210> SEQ ID NO 46
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Gly Ile Val His Asn Ala Thr Arg Phe Pro Lys Arg Cys Phe Tyr
1               5                   10                  15

Ser Phe Ile Ala Thr Arg Gln Ser Met Asn Ser Ile Arg Val Ser Gly
            20                  25                  30

<210> SEQ ID NO 47
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Gly Ile Val His Asn Ala Thr Arg Phe Pro Lys Arg Cys Phe Tyr
1               5                   10                  15

Ser Phe Ile Ala Thr Arg Gln Ser Lys Asp Ser Ile Arg Val Ser Gly
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Gly Ile Val His Asn Ala Thr Arg Leu Pro Lys Arg Cys Phe Tyr
1               5                   10                  15

Ser Phe Ile Ala Thr Arg Gln Ser Lys Asn Ser Ile Arg Val Ser Gly
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 49

Met Gly Ile Val His Asn Ala Thr Arg Phe Pro Lys Arg Cys Phe Tyr
1               5                   10                  15

Ser Phe Ile Ala Thr Arg Gln Ser Lys Asn Ser Ile Arg Val Ser Gly
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Arg Thr Phe Ser Ser Asp Gln Arg Phe Ser Lys Lys Cys Tyr Arg
1               5                   10                  15

Ile Tyr Phe His Lys Leu Arg Gln Arg Asn Arg Asn Thr Ser Val Gly
            20                  25                  30

<210> SEQ ID NO 51
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Lys Thr Phe Ser Ser Asp Gln Arg Phe Ser Lys Lys Cys Tyr Arg
1               5                   10                  15

Ile Tyr Phe His Lys Leu Arg Gln Gly Asn His Asn Thr Ser Val Gly
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Lys Thr Phe Ser Ser Asp Gln Arg Phe Ser Lys Lys Cys Tyr Arg
1               5                   10                  15

Ile Tyr Phe His Lys Leu Arg Gln Arg Asn His Asn Thr Ser Val Gly
            20                  25                  30

<210> SEQ ID NO 53
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Met Gln His Glu Asp Leu Cys Thr Trp Tyr Gly Phe Cys Pro Ser Gly
1               5                   10                  15

Asn Phe Thr Pro Arg Asn Leu Arg Gly Asp Ser Asp Gly
            20                  25

<210> SEQ ID NO 54
<211> LENGTH: 31
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Arg Tyr Ile Tyr Val Leu Arg Leu Lys Ser Trp Cys Gly Gly Ala
1               5                   10                  15

Ser Ala Arg Ser Pro Pro Arg Ser Cys Ala Thr Lys Leu Leu Gly
            20                  25                  30

<210> SEQ ID NO 55
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Arg Tyr Val Tyr Val Leu Arg Leu Lys Ser Trp Cys Gly Gly Ala
1               5                   10                  15

Ser Ala Arg Ser Ser Pro Arg Ser Cys Ala Thr Lys Leu Leu Gly
            20                  25                  30

<210> SEQ ID NO 56
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Arg Tyr Ile Tyr Val Leu Arg Leu Lys Ser Trp Cys Gly Gly Ala
1               5                   10                  15

Ser Ala Arg Ser Ser Pro Arg Ser Cys Ala Thr Lys Leu Leu Gly
            20                  25                  30

<210> SEQ ID NO 57
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Arg Tyr Ile Tyr Val Leu Arg Leu Lys Ser Trp Cys Gly Gly Ala
1               5                   10                  15

Ser Ala Arg Ser Pro Pro Arg Ser Cys Ala Thr Lys Leu Leu Gly
            20                  25                  30

<210> SEQ ID NO 58
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met His Ser Ala Tyr Leu Arg Lys Ser Met Arg Gln Leu Cys Tyr Ser
1               5                   10                  15
```

```
Arg Arg Thr Leu His Asn Ile His Val Met Ser His Arg Gly
            20                  25                  30

<210> SEQ ID NO 59
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met His Asn Ala Tyr Leu Arg Lys Ser Met Arg Gln Leu Cys Tyr Phe
1               5                   10                  15

Arg Arg Thr Leu His Asn Ile His Val Met Ser His Arg Gly
            20                  25                  30

<210> SEQ ID NO 60
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Met His Gln Lys Tyr Lys Met Ile Lys Asp Cys Phe Phe Ser Phe Leu
1               5                   10                  15

Ala His Ala Lys Lys Arg Lys Leu Tyr Pro Met Ser Gly
            20                  25

<210> SEQ ID NO 61
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Met His Gln Lys Tyr Lys Met Thr Lys Asp Cys Phe Phe Ser Phe Leu
1               5                   10                  15

Ala His Val Lys Lys Arg Lys Leu Tyr Pro Met Ser Gly
            20                  25

<210> SEQ ID NO 62
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Met His Gln Lys Tyr Lys Met Thr Lys Asp Cys Phe Phe Ser Phe Leu
1               5                   10                  15

Ala His Leu Lys Lys Arg Lys Leu Tyr Pro Met Ser Gly
            20                  25

<210> SEQ ID NO 63
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 63

Met His Gln Lys Tyr Lys Met Thr Lys Asp Cys Phe Phe Ala Phe Leu
1               5                   10                  15

Ala His His Lys Lys Arg Lys Leu Tyr Pro Met Ser Gly
            20                  25

<210> SEQ ID NO 64
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Met His Gln Lys Tyr Lys Met Thr Lys Ala Cys Phe Phe Ser Phe Leu
1               5                   10                  15

Ala His His Lys Lys Arg Lys Leu Tyr Pro Met Ser Gly
            20                  25

<210> SEQ ID NO 65
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Met His Gln Lys Tyr Lys Met Ala Lys Asp Cys Phe Phe Ser Phe Leu
1               5                   10                  15

Ala His His Lys Lys Arg Lys Leu Tyr Pro Met Ser Gly
            20                  25

<210> SEQ ID NO 66
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Met His Gln Lys Tyr Lys Met Ala Lys Ala Cys Phe Phe Ser Phe Leu
1               5                   10                  15

Ala His His Lys Lys Arg Lys Leu Tyr Pro Met Ser Gly
            20                  25

<210> SEQ ID NO 67
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Met His Gln Lys Tyr Lys Met Ala Lys Asp Cys Phe Phe Ala Phe Leu
1               5                   10                  15

Ala His His Lys Lys Arg Lys Leu Tyr Pro Met Ser Gly
            20                  25

<210> SEQ ID NO 68

```
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Met His Gln Lys Tyr Lys Met Ile Lys Ala Cys Phe Phe Ala Phe Leu
1               5                   10                  15

Ala His His Lys Lys Arg Lys Leu Tyr Pro Met Ser Gly
            20                  25

<210> SEQ ID NO 69
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Met His Gln Lys Tyr Lys Met Ala Lys Ala Cys Phe Phe Ala Phe Leu
1               5                   10                  15

Ala His His Lys Lys Arg Lys Leu Tyr Pro Met Ser Gly
            20                  25

<210> SEQ ID NO 70
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Met His Gln Lys Tyr Lys Met Ala Lys Ala Cys Phe Phe Ala Phe Leu
1               5                   10                  15

Ala His Ala Lys Lys Arg Lys Leu Tyr Pro Met Ser Gly
            20                  25

<210> SEQ ID NO 71
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Met His Gln Lys Tyr Lys Met Ala Lys Ala Cys Phe Phe Ala Phe Leu
1               5                   10                  15

Ala His Leu Lys Lys Arg Lys Leu Tyr Pro Met Ser Gly
            20                  25

<210> SEQ ID NO 72
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Met His Gln Lys Tyr Lys Met Ala Lys Ala Cys Phe Leu Ala Phe Leu
1               5                   10                  15
```

Ala His Leu Lys Lys Arg Lys Leu Tyr Pro Met Ser Gly
            20                  25

<210> SEQ ID NO 73
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Met His Gln Lys Phe Lys Met Ala Lys Ala Cys Phe Phe Ala Phe Leu
1               5                   10                  15

Ala His Leu Lys Lys Arg Lys Leu Tyr Pro Met Ser Gly
            20                  25

<210> SEQ ID NO 74
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Met His Gln Lys Tyr Lys Met Ala Ala Ala Cys Phe Phe Ala Phe Leu
1               5                   10                  15

Ala His Leu Lys Lys Arg Lys Leu Tyr Pro Met Ser Gly
            20                  25

<210> SEQ ID NO 75
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Met His Gln Lys Tyr Lys Met Ala Lys Ala Cys Phe Phe Ala Phe Leu
1               5                   10                  15

Ala His Leu Lys Lys Arg Lys Leu Tyr Pro Val Ser Gly
            20                  25

<210> SEQ ID NO 76
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Met His Ala Lys Tyr Lys Met Ala Lys Ala Cys Phe Phe Ala Phe Leu
1               5                   10                  15

Ala His Leu Lys Lys Arg Lys Leu Tyr Pro Met Ser Gly
            20                  25

<210> SEQ ID NO 77
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Met His Gln Lys Tyr Lys Met Ala Arg Ala Cys Phe Phe Ala Phe Leu
1               5                   10                  15

Ala His Leu Lys Lys Arg Lys Leu Tyr Pro Met Ser Gly
            20                  25

<210> SEQ ID NO 78
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Met Arg Gln Lys Tyr Lys Met Ala Lys Ala Cys Phe Phe Ala Phe Leu
1               5                   10                  15

Ala His Leu Lys Lys Arg Lys Leu Tyr Pro Met Ser Gly
            20                  25

<210> SEQ ID NO 79
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Met His Gln Lys Tyr Lys Met Ala Lys Ala Cys Phe Phe Ala Phe Leu
1               5                   10                  15

Ala Tyr Leu Lys Lys Arg Lys Leu Tyr Pro Met Ser Gly
            20                  25

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Met Thr His Tyr Arg Asp Asn Tyr Tyr Leu Gln Leu Gln Cys Thr Thr
1               5                   10                  15

<210> SEQ ID NO 81
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met His Gln Lys Tyr Lys Met Thr Lys Asp Cys Phe Phe Ser Phe Leu
1               5                   10                  15

Ala His His Lys Lys Arg Lys Leu Tyr Pro Met Ser Gly Ser Gly Ser
            20                  25                  30

Leu Gly His His His His His His Arg Leu
        35                  40

```
<210> SEQ ID NO 82
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Pro Asn Tyr Gly Pro Leu Ser Pro Ser Gln Pro Ser His Gly Tyr
1               5                   10                  15

Thr Phe Trp Met Val Pro Ile Trp Asp Asn Ser His Asn Ala Ala Gly
            20                  25                  30

Ser Gly Ser Leu Gly His His His His His Arg Leu
        35                  40                  45

<210> SEQ ID NO 83
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala His Gln Lys Tyr Lys Met Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 84
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Met Ala Gln Lys Tyr Lys Met Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 85
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Met His Ala Lys Tyr Lys Met Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 86
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 86

Met His Gln Ala Tyr Lys Met Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 87
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Met His Gln Lys Ala Lys Met Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 88
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Met His Gln Lys Tyr Ala Met Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 89
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Met His Gln Lys Tyr Lys Ala Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 90
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Met His Gln Lys Tyr Lys Met Thr Ala Asp Cys Phe Phe Ser Phe Leu
1               5                   10                  15

Ala His His Lys Lys Arg Lys Leu Tyr Pro Met Ser Gly
            20                  25

<210> SEQ ID NO 91
<211> LENGTH: 29
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Met His Gln Lys Tyr Lys Met Thr Lys Asp Ser Phe Phe Ser Phe Leu
1               5                   10                  15

Ala His His Lys Lys Arg Lys Leu Tyr Pro Met Ser Gly
            20                  25

<210> SEQ ID NO 92
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Met His Gln Lys Tyr Lys Met Thr Lys Asp Cys Ala Phe Ser Phe Leu
1               5                   10                  15

Ala His His Lys Lys Arg Lys Leu Tyr Pro Met Ser Gly
            20                  25

<210> SEQ ID NO 93
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Met His Gln Lys Tyr Lys Met Thr Lys Asp Cys Phe Ala Ser Phe Leu
1               5                   10                  15

Ala His His Lys Lys Arg Lys Leu Tyr Pro Met Ser Gly
            20                  25

<210> SEQ ID NO 94
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Met His Gln Lys Tyr Lys Met Thr Lys Asp Cys Phe Phe Ser Ala Leu
1               5                   10                  15

Ala His His Lys Lys Arg Lys Leu Tyr Pro Met Ser Gly
            20                  25

<210> SEQ ID NO 95
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Met His Gln Lys Tyr Lys Met Thr Lys Asp Cys Phe Phe Ser Phe Ala
1               5                   10                  15
```

Ala His His Lys Lys Arg Lys Leu Tyr Pro Met Ser Gly
            20                  25

<210> SEQ ID NO 96
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Met His Gln Lys Tyr Lys Met Thr Lys Asp Cys Phe Phe Ser Phe Leu
1               5                   10                  15

Ala Ala His Lys Lys Arg Lys Leu Tyr Pro Met Ser Gly
            20                  25

<210> SEQ ID NO 97
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Met His Gln Lys Tyr Lys Met Thr Lys Asp Cys Phe Phe Ser Phe Leu
1               5                   10                  15

Ala His Ala Lys Lys Arg Lys Leu Tyr Pro Met Ser Gly
            20                  25

<210> SEQ ID NO 98
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Met His Gln Lys Tyr Lys Met Thr Lys Asp Cys Phe Phe Ser Phe Leu
1               5                   10                  15

Ala His His Ala Lys Arg Lys Leu Tyr Pro Met Ser Gly
            20                  25

<210> SEQ ID NO 99
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Met His Gln Lys Tyr Lys Met Thr Lys Asp Cys Phe Phe Ser Phe Leu
1               5                   10                  15

Ala His His Lys Ala Arg Lys Leu Tyr Pro Met Ser Gly
            20                  25

<210> SEQ ID NO 100
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Met His Gln Lys Tyr Lys Met Thr Lys Asp Cys Phe Phe Ser Phe Leu
1               5                   10                  15

Ala His His Lys Lys Ala Lys Leu Tyr Pro Met Ser Gly
            20                  25

<210> SEQ ID NO 101
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Met His Gln Lys Tyr Lys Met Thr Lys Asp Cys Phe Phe Ser Phe Leu
1               5                   10                  15

Ala His His Lys Lys Arg Ala Leu Tyr Pro Met Ser Gly
            20                  25

<210> SEQ ID NO 102
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Met His Gln Lys Tyr Lys Met Thr Lys Asp Cys Phe Phe Ser Phe Leu
1               5                   10                  15

Ala His His Lys Lys Arg Lys Ala Tyr Pro Met Ser Gly
            20                  25

<210> SEQ ID NO 103
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Met His Gln Lys Tyr Lys Met Thr Lys Asp Cys Phe Phe Ser Phe Leu
1               5                   10                  15

Ala His His Lys Lys Arg Lys Leu Ala Pro Met Ser Gly
            20                  25

<210> SEQ ID NO 104
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Met His Gln Lys Tyr Lys Met Thr Lys Asp Cys Phe Phe Ser Phe Leu
1               5                   10                  15

Ala His His Lys Lys Arg Lys Leu Tyr Ala Met Ser Gly
            20                  25

<210> SEQ ID NO 105

```
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Met His Gln Lys Tyr Lys Met Thr Lys Asp Cys Phe Phe Ser Phe Leu
1               5                   10                  15

Ala His His Lys Lys Arg Lys Leu Tyr Pro Ala Ser Gly
            20                  25

<210> SEQ ID NO 106
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Met Asn Gln Lys Tyr Lys Met Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 107
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Met His Glu Lys Tyr Lys Met Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 108
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Met His Gln Lys Tyr Lys Lys Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 109
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Met His Gln Lys Tyr Lys Met Thr Lys Asp Cys Phe Phe Ser Phe Leu
1               5                   10                  15
```

Glu His His Lys Lys Arg Lys Leu Tyr Pro Met Ser Gly
            20                  25

<210> SEQ ID NO 110
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Met His Gln Lys Tyr Lys Met Thr Lys Asp Cys Phe Phe Ser Phe Leu
1               5                   10                  15

Ala His Leu Lys Lys Arg Lys Leu Tyr Pro Met Ser Gly
            20                  25

<210> SEQ ID NO 111
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Leu His Gln Lys Tyr Lys Met Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 112
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Met His Gln Lys Tyr Lys Met Thr Lys Ala Cys Phe Phe Ala Phe Leu
1               5                   10                  15

Ala His His Lys Lys Arg Lys Leu Tyr Pro Met Ser Gly
            20                  25

<210> SEQ ID NO 113
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Leu His Ala Lys Tyr Lys Met Thr Lys Asp Cys Phe Phe Ser Phe Leu
1               5                   10                  15

Ala His His Lys Lys Arg Lys Leu Tyr Pro Met Ser Gly
            20                  25

<210> SEQ ID NO 114
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Leu His Gln Lys Tyr Lys Met Ala Lys Ala Cys Phe Phe Ala Phe Leu
1               5                   10                  15

Glu His Leu Lys Lys Arg Lys Leu Tyr Pro Met Ser Gly
            20                  25

<210> SEQ ID NO 115
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Leu His Gln Lys Tyr Lys Met Ala Lys Ala Cys Phe Phe Ala Phe Leu
1               5                   10                  15

Ala His Leu Lys Lys Arg Lys Leu Tyr Pro Met Ser Gly
            20                  25

<210> SEQ ID NO 116
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Met His Gln Lys Tyr Lys Met Ala Lys Ala Cys Phe Phe Ala Phe Leu
1               5                   10                  15

Glu His Leu Lys Lys Arg Lys Leu Tyr Pro Met Ser Gly
            20                  25

<210> SEQ ID NO 117
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Met His Glu Lys Tyr Lys Met Ala Lys Ala Cys Phe Phe Ala Phe Leu
1               5                   10                  15

Ala His Leu Lys Lys Arg Lys Leu Tyr Pro Met Ser Gly
            20                  25

<210> SEQ ID NO 118
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Met His Ala Lys Tyr Lys Met Ala Lys Ala Cys Phe Phe Ala Phe Leu
1               5                   10                  15

Ala His Leu Lys Lys Arg Lys Leu Tyr Pro Met Ser Gly
            20                  25

-continued

```
<210> SEQ ID NO 119
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Met His Gln Lys Tyr Lys Met Ala Ala Ala Cys Phe Phe Ala Phe Leu
1               5                   10                  15

Ala His Leu Lys Lys Arg Lys Leu Tyr Pro Met Ser Gly
            20                  25

<210> SEQ ID NO 120
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Met His Gln Lys Tyr Lys Met Ala Lys Ala Cys Phe Phe Ala Phe Leu
1               5                   10                  15

Ala His Leu Ala Lys Arg Lys Leu Tyr Pro Met Ser Gly
            20                  25

<210> SEQ ID NO 121
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Met Asn Gln Lys Tyr Lys Met Ala Lys Ala Cys Phe Phe Ala Phe Leu
1               5                   10                  15

Ala His Leu Lys Lys Arg Lys Leu Tyr Pro Met Ser Gly
            20                  25

<210> SEQ ID NO 122
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Met His Glu Lys Tyr Lys Met Ala Lys Ala Cys Phe Phe Ala Phe Leu
1               5                   10                  15

Glu His Leu Lys Lys Arg Lys Leu Tyr Pro Met Ser Gly
            20                  25

<210> SEQ ID NO 123
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Met His Glu Lys Tyr Lys Lys Ala Lys Ala Cys Phe Phe Ala Phe Leu
```

```
                1               5                  10                  15
Glu His Leu Lys Lys Arg Lys Leu Tyr Pro Met Ser Gly
            20                  25

<210> SEQ ID NO 124
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Met His Gln Lys Tyr Lys Met Ala Lys Ala Cys Phe Phe Ala Phe Leu
1               5                   10                  15

Glu His Leu Lys Lys Arg Lys Leu Tyr Pro Met Ser
            20                  25

<210> SEQ ID NO 125
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Met His Gln Lys Tyr Lys Met Ala Lys Ala Cys Phe Phe Ala Phe Leu
1               5                   10                  15

Glu His Leu Lys Lys Arg Lys Leu Tyr Pro Met
            20                  25

<210> SEQ ID NO 126
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Met His Gln Lys Tyr Lys Met Ala Lys Ala Cys Phe Phe Ala Phe Leu
1               5                   10                  15

Glu His Leu Lys Lys Arg Lys Leu Tyr Pro
            20                  25

<210> SEQ ID NO 127
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Met His Gln Lys Tyr Lys Met Ala Lys Ala Cys Phe Phe Ala Phe Leu
1               5                   10                  15

Glu His Leu Lys Lys Arg Lys Leu Tyr
            20                  25

<210> SEQ ID NO 128
<211> LENGTH: 24
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 128

Met His Gln Lys Tyr Lys Met Ala Lys Ala Cys Phe Phe Ala Phe Leu
1               5                   10                  15

Glu His Leu Lys Lys Arg Lys Leu
            20

<210> SEQ ID NO 129
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Met His Gln Lys Tyr Lys Met Ala Lys Ala Cys Phe Phe Ala Phe Leu
1               5                   10                  15

Glu His Leu Lys Lys Arg Lys
            20

<210> SEQ ID NO 130
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

His Gln Lys Tyr Lys Met Ala Lys Ala Cys Phe Phe Ala Phe Leu Glu
1               5                   10                  15

His Leu Lys Lys Arg Lys Leu Tyr Pro Met Ser Gly
            20                  25

<210> SEQ ID NO 131
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gln Lys Tyr Lys Met Ala Lys Ala Cys Phe Phe Ala Phe Leu Glu His
1               5                   10                  15

Leu Lys Lys Arg Lys Leu Tyr Pro Met Ser Gly
            20                  25

<210> SEQ ID NO 132
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Lys Tyr Lys Met Ala Lys Ala Cys Phe Phe Ala Phe Leu Glu His Leu
1               5                   10                  15

Lys Lys Arg Lys Leu Tyr Pro Met Ser Gly
            20                  25
```

<210> SEQ ID NO 133
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Met Asn Gln Lys Tyr Lys Met Ala Lys Ala Cys Phe Phe Ala Phe Leu
1               5                   10                  15

Glu His Leu Lys Lys Arg Lys Leu Tyr Pro Met Ser Gly
            20                  25

<210> SEQ ID NO 134
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Met Asn Gln Lys Tyr Lys Met Ala Lys Ala Ala Phe Phe Ala Phe Leu
1               5                   10                  15

Glu His Leu Lys Lys Arg Lys Leu Tyr Pro Met Ser Gly
            20                  25

<210> SEQ ID NO 135
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Met Asn Gln Lys Tyr Lys Met Ala Lys Ala Ser Phe Phe Ala Phe Leu
1               5                   10                  15

Glu His Leu Lys Lys Arg Lys Leu Tyr Pro Met Ser Gly
            20                  25

<210> SEQ ID NO 136
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asn Gln Lys Tyr Lys Met Ala Lys Ala Cys Phe Phe Ala Phe Leu Glu
1               5                   10                  15

His Leu Lys Lys Arg Lys Leu Tyr Pro Met Ser Gly
            20                  25

<210> SEQ ID NO 137
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

```
Tyr Lys Met Ala Lys Ala Cys Phe Phe Ala Phe Leu Glu His Leu Lys
1               5                   10                  15

Lys Arg Lys Leu Tyr Pro Met Ser Gly
            20                  25

<210> SEQ ID NO 138
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Met Asn Gln Lys Tyr Lys Met Ala Lys Ala Cys Phe Phe Ala Phe Leu
1               5                   10                  15

Glu His Leu Lys Lys Arg Lys Leu Tyr Pro Met Ser
            20                  25

<210> SEQ ID NO 139
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Met Asn Gln Lys Tyr Lys Met Ala Lys Ala Cys Phe Phe Ala Phe Leu
1               5                   10                  15

Glu His Leu Lys Lys Arg Lys Leu Tyr Pro Met
            20                  25

<210> SEQ ID NO 140
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Met Asn Gln Lys Tyr Lys Met Ala Lys Ala Cys Phe Phe Ala Phe Leu
1               5                   10                  15

Glu His Leu Lys Lys Arg Lys Leu Tyr Pro
            20                  25

<210> SEQ ID NO 141
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Met Asn Gln Lys Tyr Lys Met Ala Lys Ala Cys Phe Phe Ala Phe Leu
1               5                   10                  15

Glu His Leu Lys Lys Arg Lys Leu Tyr
            20                  25

<210> SEQ ID NO 142
<211> LENGTH: 24
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 142

Met Asn Gln Lys Tyr Lys Met Ala Lys Ala Cys Phe Phe Ala Phe Leu
1               5                   10                  15

Glu His Leu Lys Lys Arg Lys Leu
            20

<210> SEQ ID NO 143
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Met Asn Gln Lys Tyr Lys Met Ala Lys Ala Cys Phe Phe Ala Phe Leu
1               5                   10                  15

Glu His Leu Lys Lys Arg Lys
            20

<210> SEQ ID NO 144
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Met Val Lys Leu Ser Gly Lys Glu Arg Thr Thr Arg Asn Cys Phe Phe
1               5                   10                  15

Ser Phe Leu Ala Ser Arg Arg Thr Lys Lys Phe Asn Asn Leu Ser Gly
            20                  25                  30

<210> SEQ ID NO 145
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Met Gly His Leu His Ile Cys Met Val Trp Arg Val Asn Thr Ser Gly
1               5                   10                  15

His Ile Leu Ser Val Gly His Lys Ser Tyr Ser Ser His Lys Thr Gly
            20                  25                  30

<210> SEQ ID NO 146
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Met Ser Ser Gly Thr His Tyr Gly Ile Leu Asn Met Val Ile Arg Cys
1               5                   10                  15

His Leu Val Lys Asn Gln Thr Ser Gln Met Val Val Leu Thr Thr Gly
            20                  25                  30

<210> SEQ ID NO 147
<211> LENGTH: 31
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 147

Met His His Tyr Cys Ser Lys Met Lys Arg Arg Ile Leu Met His Tyr
1               5                   10                  15

Leu Phe Ala Asn Thr Met Ala His Arg Asp Leu Gly Thr Asn Gly
            20                  25                  30

<210> SEQ ID NO 148
<211> LENGTH: 32
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 148

Met His Leu Arg Met Ile Arg Tyr Leu Asn Arg Arg His Leu Cys
1               5                   10                  15

His Val Val Glu Ile Arg His Gly Leu Phe Ala Ser Arg Glu Ile Gly
            20                  25                  30

<210> SEQ ID NO 149
<211> LENGTH: 31
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 149

Met Asn Gly His Tyr Pro Cys Tyr Leu Ile Thr Ser Val Leu Val Gly
1               5                   10                  15

Ala Thr Thr Ser Gly Val Pro Val Val His Leu Arg Val Gly
            20                  25                  30

<210> SEQ ID NO 150
<211> LENGTH: 29
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 150

Met Arg His Tyr His Leu Thr Cys Phe Gln Gly Phe Arg Ile Phe Arg
1               5                   10                  15

Arg Thr Val Asp Ser Leu Glu Met Glu Ile Ser Leu Gly
            20                  25

<210> SEQ ID NO 151
<211> LENGTH: 32
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 151

```
Met His Met His Lys Thr Thr Ser Tyr Arg Ile Arg Val Leu Val Gly
1               5                   10                  15

Val Asp Val Tyr Arg Met Ser His Thr Cys Leu Thr Ser Ser Ser Gly
            20                  25                  30

<210> SEQ ID NO 152
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Met His Thr Ser Leu Arg Ser Arg Ala Lys Ser His Ser Arg Ser Phe
1               5                   10                  15

Gly Lys Cys Ala Ser Ile Tyr Thr Arg Tyr Leu Lys Met Gly
            20                  25                  30

<210> SEQ ID NO 153
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Met Gln Asn Ser Lys His Arg Pro Arg Arg Cys Leu Arg Leu Leu Pro
1               5                   10                  15

Leu Leu Arg Gly His Leu His Arg Met Phe Arg Glu Arg Gly
            20                  25                  30

<210> SEQ ID NO 154
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Met Arg Ser Thr His Gln Arg Val Arg Arg Pro Arg Asn Leu Cys Ser
1               5                   10                  15

Phe Lys His Lys Trp Leu Ile Lys Phe Leu Lys Thr Leu Thr Gly
            20                  25                  30

<210> SEQ ID NO 155
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Met Arg Arg Thr Pro Ser Thr Arg Ala Arg Gly Arg Val Phe Leu Leu
1               5                   10                  15

Pro Thr Leu Arg Phe Phe Ile Thr Leu Cys Asn Leu Asn Gly
            20                  25                  30

<210> SEQ ID NO 156
<211> LENGTH: 32
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 156

Met Asn Arg Ile Phe His Lys Arg Ser Thr Tyr Gln Met Val Phe Gly
1               5                   10                  15

Arg Cys Ser Asp Phe Thr Ser Thr Tyr His Val Leu Ile Ser Tyr Gly
            20                  25                  30

<210> SEQ ID NO 157
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Met Thr Ala Thr Ser Ser Ser Thr Ser Arg Gly Cys Arg Pro Ser Thr
1               5                   10                  15

Ala Gln Val Val Gln Arg Leu Arg Gly Leu Leu Leu Val Val Gly
            20                  25                  30

<210> SEQ ID NO 158
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Met Leu Phe Met Arg Leu Thr Lys Lys Thr Met Ala Thr Lys Phe Cys
1               5                   10                  15

Pro Phe Arg Arg Lys Arg Lys His Arg Glu Arg Arg Ala Leu Tyr Gly
            20                  25                  30

<210> SEQ ID NO 159
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Lys Met Thr Lys Asp Cys Phe Phe Ser Phe Leu
1               5                   10

<210> SEQ ID NO 160
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Phe Cys His Phe
1

<210> SEQ ID NO 161
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 161

Phe Cys Ala Phe
1

<210> SEQ ID NO 162
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Phe Gly Pro Phe
1

<210> SEQ ID NO 163
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Phe Cys Pro Leu
1

<210> SEQ ID NO 164
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Phe Cys Pro Phe
1

<210> SEQ ID NO 165
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Phe Cys Ser Phe
1

<210> SEQ ID NO 166
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Cys Pro Phe Arg
1
```

<210> SEQ ID NO 167
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Phe Cys Leu Phe
1

<210> SEQ ID NO 168
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Leu Leu Leu Leu
1

<210> SEQ ID NO 169
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Phe Cys Thr Phe
1

<210> SEQ ID NO 170
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Leu Cys Pro Phe
1

<210> SEQ ID NO 171
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Phe Arg Pro Phe
1

<210> SEQ ID NO 172
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 172

Phe Ser Pro Phe
1

<210> SEQ ID NO 173
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Phe Cys Arg Phe
1

<210> SEQ ID NO 174
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Phe Cys Pro Ser
1

<210> SEQ ID NO 175
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ser Phe Cys Pro
1

<210> SEQ ID NO 176
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Val Cys Pro Phe
1

<210> SEQ ID NO 177
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Cys Pro Phe Leu
1

<210> SEQ ID NO 178
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Cys Pro Phe Ser
1

<210> SEQ ID NO 179
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Arg Phe Cys Pro
1

<210> SEQ ID NO 180
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Cys Cys Pro Phe
1

<210> SEQ ID NO 181
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Phe Cys Pro Ile
1

<210> SEQ ID NO 182
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Trp Cys Pro Phe
1

<210> SEQ ID NO 183
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

His His His His His His Arg Leu
```

```
1               5
```

<210> SEQ ID NO 184
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

```
Gly Cys Pro Gly Gly Leu Leu Lys Asn Lys
1               5                   10
```

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

```
Tyr Ala Leu Pro Ser Thr Gly Gly
1               5
```

<210> SEQ ID NO 186
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

```
Gly Gly Gly Gly Gly Ala Gly Tyr Leu Leu Gly Lys Ile Asn Leu Lys
1               5                   10                  15

Ala Leu Ala Ala Leu Ala Lys Lys Ile Leu
            20                  25
```

<210> SEQ ID NO 187
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

```
Ser Gly Ser Leu Gly His His His His His His Arg Leu
1               5                   10
```

<210> SEQ ID NO 188
<211> LENGTH: 188
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (46)..(47)
<223> OTHER INFORMATION: a, c, t, g, unknown or other
<220> FEATURE:
<221> NAME/KEY: modified_base
<222> LOCATION: (49)..(50)
<223> OTHER INFORMATION: a, c, t, g, unknown or other
<220> FEATURE:
<221> NAME/KEY: modified_base -continued

```
<222> LOCATION: (52)..(53)
<223> OTHER INFORMATION: a, c, t, g, unknown or other
<220> FEATURE:
<221> NAME/KEY: modified_base
<222> LOCATION: (55)..(56)
<223> OTHER INFORMATION: a, c, t, g, unknown or other
<220> FEATURE:
<221> NAME/KEY: modified_base
<222> LOCATION: (58)..(59)
<223> OTHER INFORMATION: a, c, t, g, unknown or other
<220> FEATURE:
<221> NAME/KEY: modified_base
<222> LOCATION: (61)..(62)
<223> OTHER INFORMATION: a, c, t, g, unknown or other
<220> FEATURE:
<221> NAME/KEY: modified_base
<222> LOCATION: (64)..(65)
<223> OTHER INFORMATION: a, c, t, g, unknown or other
<220> FEATURE:
<221> NAME/KEY: modified_base
<222> LOCATION: (67)..(68)
<223> OTHER INFORMATION: a, c, t, g, unknown or other
<220> FEATURE:
<221> NAME/KEY: modified_base
<222> LOCATION: (70)..(71)
<223> OTHER INFORMATION: a, c, t, g, unknown or other
<220> FEATURE:
<221> NAME/KEY: modified_base
<222> LOCATION: (73)..(74)
<223> OTHER INFORMATION: a, c, t, g, unknown or other
<220> FEATURE:
<221> NAME/KEY: modified_base
<222> LOCATION: (76)..(77)
<223> OTHER INFORMATION: a, c, t, g, unknown or other
<220> FEATURE:
<221> NAME/KEY: modified_base
<222> LOCATION: (79)..(80)
<223> OTHER INFORMATION: a, c, t, g, unknown or other
<220> FEATURE:
<221> NAME/KEY: modified_base
<222> LOCATION: (82)..(83)
<223> OTHER INFORMATION: a, c, t, g, unknown or other
<220> FEATURE:
<221> NAME/KEY: modified_base
<222> LOCATION: (85)..(86)
<223> OTHER INFORMATION: a, c, t or g
<220> FEATURE:
<221> NAME/KEY: modified_base
<222> LOCATION: (88)..(89)
<223> OTHER INFORMATION: a, c, t or g
<220> FEATURE:
<221> NAME/KEY: modified_base
<222> LOCATION: (91)..(92)
<223> OTHER INFORMATION: a, c, t or g
<220> FEATURE:
<221> NAME/KEY: modified_base
<222> LOCATION: (94)..(95)
<223> OTHER INFORMATION: a, c, t or g
<220> FEATURE:
<221> NAME/KEY: modified_base
<222> LOCATION: (97)..(98)
<223> OTHER INFORMATION: a, c, t, g, unknown or other
<220> FEATURE:
<221> NAME/KEY: modified_base
<222> LOCATION: (100)..(101)
<223> OTHER INFORMATION: a, c, t, g, unknown or other
<220> FEATURE:
<221> NAME/KEY: modified_base
<222> LOCATION: (103)..(104)
<223> OTHER INFORMATION: a, c, t, g, unknown or other
<220> FEATURE:
<221> NAME/KEY: modified_base
<222> LOCATION: (106)..(107)
<223> OTHER INFORMATION: a, c, t, g, unknown or other
<220> FEATURE:
<221> NAME/KEY: modified_base
<222> LOCATION: (109)..(110)
<223> OTHER INFORMATION: a, c, t, g, unknown or other
<220> FEATURE:
```

```
<221> NAME/KEY: modified_base
<222> LOCATION: (112)..(113)
<223> OTHER INFORMATION: a, c, t, g, unknown or other
<220> FEATURE:
<221> NAME/KEY: modified_base
<222> LOCATION: (115)..(116)
<223> OTHER INFORMATION: a, c, t, g, unknown or other
<220> FEATURE:
<221> NAME/KEY: modified_base
<222> LOCATION: (118)..(119)
<223> OTHER INFORMATION: a, c, t, g, unknown or other
<220> FEATURE:
<221> NAME/KEY: modified_base
<222> LOCATION: (121)..(122)
<223> OTHER INFORMATION: a, c, t, g, unknown or other
<220> FEATURE:
<221> NAME/KEY: modified_base
<222> LOCATION: (124)..(125)
<223> OTHER INFORMATION: a, c, t, g, unknown or other
<220> FEATURE:
<221> NAME/KEY: modified_base
<222> LOCATION: (127)..(128)
<223> OTHER INFORMATION: a, c, t, g, unknown or other
<220> FEATURE:
<221> NAME/KEY: modified_base
<222> LOCATION: (130)..(131)
<223> OTHER INFORMATION: a, c, t, g, unknown or other
<220> FEATURE:
<221> NAME/KEY: modified_base
<222> LOCATION: (133)..(134)
<223> OTHER INFORMATION: a, c, t, g, unknown or other

<400> SEQUENCE: 188
taatacgact cactataggg acaattacta tttacaatta caatgnnsnn snnsnnsnns     60
nnsnnsnnsn nsnnsnnsnn snnsnnsnns nnsnnsnnsn nsnnsnnsnn snnsnnsnns    120
nnsnnsnnsn nsnnsggctc cggtagctta ggccaccatc accatcacca ccggctatag    180
gtagctag                                                             188

<210> SEQ ID NO 189
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (40)..(41)
<223> OTHER INFORMATION: a, c, t, g, unknown or other
<220> FEATURE:
<221> NAME/KEY: modified_base
<222> LOCATION: (43)..(44)
<223> OTHER INFORMATION: a, c, t, g, unknown or other
<220> FEATURE:
<221> NAME/KEY: modified_base
<222> LOCATION: (46)..(47)
<223> OTHER INFORMATION: a, c, t, g, unknown or other
<220> FEATURE:
<221> NAME/KEY: modified_base
<222> LOCATION: (49)..(50)
<223> OTHER INFORMATION: a, c, t, g, unknown or other
<220> FEATURE:
<221> NAME/KEY: modified_base
<222> LOCATION: (52)..(53)
<223> OTHER INFORMATION: a, c, t, g, unknown or other
<220> FEATURE:
<221> NAME/KEY: modified_base
<222> LOCATION: (55)..(56)
<223> OTHER INFORMATION: a, c, t, g, unknown or other
<220> FEATURE:
```

```
<221> NAME/KEY: modified_base
<222> LOCATION: (58)..(59)
<223> OTHER INFORMATION: a, c, t, g, unknown or other
<220> FEATURE:
<221> NAME/KEY: modified_base
<222> LOCATION: (61)..(62)
<223> OTHER INFORMATION: a, c, t, g, unknown or other
<220> FEATURE:
<221> NAME/KEY: modified_base
<222> LOCATION: (64)..(65)
<223> OTHER INFORMATION: a, c, t, g, unknown or other
<220> FEATURE:
<221> NAME/KEY: modified_base
<222> LOCATION: (67)..(68)
<223> OTHER INFORMATION: a, c, t, g, unknown or other
<220> FEATURE:
<221> NAME/KEY: modified_base
<222> LOCATION: (70)..(71)
<223> OTHER INFORMATION: a, c, t, g, unknown or other
<220> FEATURE:
<221> NAME/KEY: modified_base
<222> LOCATION: (73)..(74)
<223> OTHER INFORMATION: a, c, t, g, unknown or other
<220> FEATURE:
<221> NAME/KEY: modified_base
<222> LOCATION: (76)..(77)
<223> OTHER INFORMATION: a, c, t or g
<220> FEATURE:
<221> NAME/KEY: modified_base
<222> LOCATION: (79)..(80)
<223> OTHER INFORMATION: a, c, t or g
<220> FEATURE:
<221> NAME/KEY: modified_base
<222> LOCATION: (82)..(83)
<223> OTHER INFORMATION: a, c, t or g
<220> FEATURE:
<221> NAME/KEY: modified_base
<222> LOCATION: (85)..(86)
<223> OTHER INFORMATION: a, c, t or g
<220> FEATURE:
<221> NAME/KEY: modified_base
<222> LOCATION: (88)..(89)
<223> OTHER INFORMATION: a, c, t, g, unknown or other
<220> FEATURE:
<221> NAME/KEY: modified_base
<222> LOCATION: (91)..(92)
<223> OTHER INFORMATION: a, c, t, g, unknown or other
<220> FEATURE:
<221> NAME/KEY: modified_base
<222> LOCATION: (94)..(95)
<223> OTHER INFORMATION: a, c, t, g, unknown or other
<220> FEATURE:
<221> NAME/KEY: modified_base
<222> LOCATION: (97)..(98)
<223> OTHER INFORMATION: a, c, t, g, unknown or other
<220> FEATURE:
<221> NAME/KEY: modified_base
<222> LOCATION: (100)..(101)
<223> OTHER INFORMATION: a, c, t, g, unknown or other
<220> FEATURE:
<221> NAME/KEY: modified_base
<222> LOCATION: (103)..(104)
<223> OTHER INFORMATION: a, c, t, g, unknown or other
<220> FEATURE:
<221> NAME/KEY: modified_base
<222> LOCATION: (106)..(107)
<223> OTHER INFORMATION: a, c, t, g, unknown or other
<220> FEATURE:
<221> NAME/KEY: modified_base
<222> LOCATION: (109)..(110)
<223> OTHER INFORMATION: a, c, t, g, unknown or other
<220> FEATURE:
<221> NAME/KEY: modified_base
<222> LOCATION: (112)..(113)
<223> OTHER INFORMATION: a, c, t, g, unknown or other
<220> FEATURE:
<221> NAME/KEY: modified_base
<222> LOCATION: (115)..(116)
<223> OTHER INFORMATION: a, c, t, g, unknown or other
```

```
<220> FEATURE:
<221> NAME/KEY: modified_base
<222> LOCATION: (118)..(119)
<223> OTHER INFORMATION: a, c, t, g, unknown or other
<220> FEATURE:
<221> NAME/KEY: modified_base
<222> LOCATION: (121)..(122)
<223> OTHER INFORMATION: a, c, t, g, unknown or other
<220> FEATURE:
<221> NAME/KEY: modified_base
<222> LOCATION: (124)..(125)
<223> OTHER INFORMATION: a, c, t, g, unknown or other

<400> SEQUENCE: 189
tcactatagg gacaattact atttacaatt acaatgnnsn nsnnsnnsnn snnsnnsnns      60
nnsnnsnnsn nsnnsnnsnn snnsnnsnns nnsnnsnnsn nsnnsnnsnn snnsnnsnns     120
nnsnnsggct ccggtagctt aggc                                           144

<210> SEQ ID NO 190
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
taatacgact cactataggg acaattacta tttacaatta ca                        42

<210> SEQ ID NO 191
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
ctagctacct atagccggtg gtgatggtga tggtggccta agctaccgga gcc             53

<210> SEQ ID NO 192
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
tttttttttt tttttgtgat ggtgatggtg gcctaa                               36

<210> SEQ ID NO 193
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
uagccgguga aaaaaaaaaa aaaa                                            24

<210> SEQ ID NO 194
<211> LENGTH: 321
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 194

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly Met His Gln Lys Tyr Lys Met Thr Lys
        115                 120                 125

Asp Cys Phe Phe Ser Phe Leu Ala His Ile Lys Lys Arg Lys Leu Tyr
130                 135                 140

Pro Met Ser Gly Ser Gly Ser Leu Gly His His His His His His Arg
145                 150                 155                 160

Leu Gly Glu Asn Leu Tyr Phe Gln Gly Gly Asp Pro Asn Ser Gln Ala
                165                 170                 175

Lys Pro Gln Ile Pro Lys Asp Lys Ser Lys Val Ala Gly Tyr Ile Glu
            180                 185                 190

Ile Pro Asp Ala Asp Ile Lys Glu Pro Val Tyr Pro Gly Pro Ala Thr
        195                 200                 205

Ser Glu Gln Leu Asn Arg Gly Val Ser Phe Ala Glu Glu Asn Glu Ser
210                 215                 220

Leu Asp Asp Gln Asn Ile Ser Ile Ala Gly His Thr Phe Ile Asp Arg
225                 230                 235                 240

Pro Asn Tyr Gln Phe Thr Asn Leu Lys Ala Ala Lys Lys Gly Ser Met
                245                 250                 255

Val Tyr Phe Lys Val Gly Asn Glu Thr Arg Lys Tyr Lys Met Thr Ser
            260                 265                 270

Ile Arg Asn Val Lys Pro Thr Asp Val Glu Val Leu Asp Glu Gln Lys
        275                 280                 285

Gly Lys Asp Lys Gln Leu Thr Leu Ile Thr Cys Asp Asp Tyr Asn Glu
290                 295                 300

Lys Thr Gly Val Trp Glu Thr Arg Lys Ile Phe Val Ala Thr Glu Val
305                 310                 315                 320

Lys

<210> SEQ ID NO 195
<211> LENGTH: 321
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Met Gly Ser Ser His His His His His His Gly Ser Gly Leu Val Pro

```
                1               5                  10                  15
        Arg Gly Ser Ala Ser Met Ser Asp Ser Glu Val Asn Gln Glu Ala Lys
                        20                  25                  30

Pro Glu Val Lys Pro Glu Val Lys Pro Glu Thr His Ile Asn Leu Lys
                        35                  40                  45

Val Ser Asp Gly Ser Ser Glu Ile Phe Phe Lys Ile Lys Lys Thr Thr
                        50                  55                  60

Pro Leu Arg Arg Leu Met Glu Ala Phe Ala Lys Arg Gln Gly Lys Glu
         65                 70                  75                  80

Met Asp Ser Leu Arg Phe Leu Tyr Asp Gly Ile Arg Ile Gln Ala Asp
                        85                  90                  95

Gln Thr Pro Glu Asp Leu Asp Met Glu Asp Asn Asp Ile Ile Glu Ala
                        100                 105                 110

His Arg Glu Gln Ile Gly Gly Met His Asn Ala Tyr Leu Arg Lys Ser
                        115                 120                 125

Met Arg Gln Leu Cys Tyr Phe Arg Arg Thr Leu His Asn Ile His Val
                        130                 135                 140

Met Ser His Arg Gly Ser Gly Ser Leu Gly His His His His His His
        145                 150                 155                 160

Arg Leu Gly Glu Asn Leu Tyr Phe Gln Gly Gly Asp Pro Asn Ser Gln
                        165                 170                 175

Ala Lys Pro Gln Ile Pro Lys Asp Lys Ser Lys Val Ala Gly Tyr Ile
                        180                 185                 190

Glu Ile Pro Asp Ala Asp Ile Lys Glu Pro Val Tyr Pro Gly Pro Ala
                        195                 200                 205

Thr Ser Glu Gln Leu Asn Arg Gly Val Ser Phe Ala Glu Glu Asn Glu
                        210                 215                 220

Ser Leu Asp Asp Gln Asn Ile Ser Ile Ala Gly His Thr Phe Ile Asp
        225                 230                 235                 240

Arg Pro Asn Tyr Gln Phe Thr Asn Leu Ala Ala Lys Lys Gly Ser Met
                        245                 250                 255

Val Tyr Phe Lys Val Gly Asn Glu Thr Arg Lys Tyr Lys Met Thr Ser
                        260                 265                 270

Ile Arg Asn Val Lys Pro Thr Asp Val Glu Val Leu Asp Glu Gln Lys
                        275                 280                 285

Gly Lys Asp Lys Gln Leu Thr Leu Ile Thr Cys Asp Asp Tyr Asn Glu
                        290                 295                 300

Lys Thr Gly Val Trp Glu Thr Arg Lys Ile Phe Val Ala Thr Glu Val
        305                 310                 315                 320

Lys

<210> SEQ ID NO 196
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Arg Phe Cys Pro Phe
1               5

<210> SEQ ID NO 197
<211> LENGTH: 5
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 197

Ser Phe Cys Pro Phe
1               5

<210> SEQ ID NO 198
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Phe Cys Pro Phe Arg
1               5

<210> SEQ ID NO 199
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Phe Cys Pro Phe Ser
1               5

<210> SEQ ID NO 200
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Thr Phe Cys Pro Phe
1               5

<210> SEQ ID NO 201
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Phe Cys Pro Phe Thr
1               5

<210> SEQ ID NO 202
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Arg Phe Cys Pro Phe
1               5

<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ser Phe Cys Pro Phe
1               5

<210> SEQ ID NO 204
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Phe Cys Pro Phe Leu
1               5

<210> SEQ ID NO 205
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Phe Cys Pro Phe Arg
1               5

<210> SEQ ID NO 206
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Phe Cys Pro Phe Ser
1               5

<210> SEQ ID NO 207
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Gly Phe Cys Pro Phe
1               5

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Leu Phe Cys Pro Phe
1               5

<210> SEQ ID NO 209
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Phe Cys Pro Phe Arg Ser
1               5

<210> SEQ ID NO 210
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Phe Cys Pro Phe Arg Arg
1               5

<210> SEQ ID NO 211
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Leu Ser Phe Cys Pro Phe
1               5

<210> SEQ ID NO 212
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Leu Arg Phe Cys Pro Phe
1               5

<210> SEQ ID NO 213
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Phe Cys Pro Phe Arg Thr
1               5

<210> SEQ ID NO 214
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Phe Cys Pro Phe Arg Leu
1               5

<210> SEQ ID NO 215
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Val Arg Phe Cys Pro Phe
1               5

<210> SEQ ID NO 216
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Thr Phe Cys Pro Phe Arg
1               5

<210> SEQ ID NO 217
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Arg Phe Cys Pro Phe Ser
1               5

<210> SEQ ID NO 218
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Arg Leu Phe Cys Pro Phe
1               5

<210> SEQ ID NO 219
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Arg Ser Phe Cys Pro Phe
```

```
1               5
```

<210> SEQ ID NO 220
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

```
Ser Ser Phe Cys Pro Phe
1               5
```

<210> SEQ ID NO 221
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

```
Ser Arg Phe Cys Pro Phe
1               5
```

<210> SEQ ID NO 222
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

```
Arg Phe Cys Pro Phe Leu
1               5
```

<210> SEQ ID NO 223
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

```
Phe Cys Pro Phe Leu Leu
1               5
```

<210> SEQ ID NO 224
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

```
Phe Cys Pro Phe Ser Arg
1               5
```

<210> SEQ ID NO 225
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 225

Phe Cys Pro Phe Ser Ser
1               5

<210> SEQ ID NO 226
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Arg Phe Cys Pro Phe Arg
1               5

<210> SEQ ID NO 227
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Phe Cys Pro Phe Leu Ser
1               5

<210> SEQ ID NO 228
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Phe Cys Pro Phe Leu Arg
1               5

<210> SEQ ID NO 229
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ser Phe Cys Pro Phe Leu
1               5

<210> SEQ ID NO 230
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Leu Phe Cys Pro Phe Arg
1               5

<210> SEQ ID NO 231

<210> SEQ ID NO 231
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Arg Thr Phe Cys Pro Phe
1               5

<210> SEQ ID NO 232
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Arg Arg Phe Cys Pro Phe
1               5

<210> SEQ ID NO 233
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ser Phe Cys Pro Phe Arg
1               5

<210> SEQ ID NO 234
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ser Phe Cys Pro Phe Ser
1               5

<210> SEQ ID NO 235
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Phe Cys Pro Phe Arg Ser
1               5

<210> SEQ ID NO 236
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Phe Cys Pro Phe Arg Arg
1               5

<210> SEQ ID NO 237
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Arg Ala Phe Cys Pro Phe
1               5

<210> SEQ ID NO 238
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Leu Arg Phe Cys Pro Phe
1               5

<210> SEQ ID NO 239
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Phe Cys Pro Phe Arg Thr
1               5

<210> SEQ ID NO 240
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Phe Cys Pro Phe Arg Leu
1               5

<210> SEQ ID NO 241
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Phe Cys Pro Phe Arg Gly
1               5

<210> SEQ ID NO 242
<211> LENGTH: 6
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 242

Thr Phe Cys Pro Phe Arg
1               5

<210> SEQ ID NO 243
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Phe Cys Pro Phe Thr Arg
1               5

<210> SEQ ID NO 244
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Gly Phe Cys Pro Phe Arg
1               5

<210> SEQ ID NO 245
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Arg Phe Cys Pro Phe Ser
1               5

<210> SEQ ID NO 246
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Arg Leu Phe Cys Pro Phe
1               5

<210> SEQ ID NO 247
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Arg Phe Cys Pro Phe Thr
1               5
```

```
<210> SEQ ID NO 248
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Arg Ser Phe Cys Pro Phe
1               5

<210> SEQ ID NO 249
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Thr Arg Phe Cys Pro Phe
1               5

<210> SEQ ID NO 250
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Ser Ser Phe Cys Pro Phe
1               5

<210> SEQ ID NO 251
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ser Arg Phe Cys Pro Phe
1               5

<210> SEQ ID NO 252
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Arg Phe Cys Pro Phe Leu
1               5

<210> SEQ ID NO 253
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253
```

```
Phe Cys Pro Phe Ser Arg
1               5

<210> SEQ ID NO 254
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Phe Cys Pro Phe Ser Ser
1               5

<210> SEQ ID NO 255
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Arg Phe Cys Pro Phe Arg
1               5

<210> SEQ ID NO 256
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Phe Cys Pro Phe Leu Ser
1               5

<210> SEQ ID NO 257
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Phe Cys Pro Phe Leu Arg
1               5

<210> SEQ ID NO 258
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Arg Cys Phe Cys Pro Phe
1               5

<210> SEQ ID NO 259
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 259

Ser Phe Cys Pro Phe Leu
1               5

<210> SEQ ID NO 260
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Leu Phe Cys Pro Phe Arg
1               5

<210> SEQ ID NO 261
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Arg Thr Phe Cys Pro Phe
1               5

<210> SEQ ID NO 262
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Arg Gly Phe Cys Pro Phe
1               5

<210> SEQ ID NO 263
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Arg Arg Phe Cys Pro Phe
1               5

<210> SEQ ID NO 264
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ser Phe Cys Pro Phe Arg
1               5
```

<210> SEQ ID NO 265
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Ser Phe Cys Pro Phe Ser
1               5

<210> SEQ ID NO 266
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Thr Lys Asp Cys Phe Phe Ser
1               5

<210> SEQ ID NO 267
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Arg Arg Ser Phe Cys Pro Phe
1               5

<210> SEQ ID NO 268
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Arg Val Arg Phe Cys Pro Phe
1               5

<210> SEQ ID NO 269
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Arg Phe Cys Pro Phe Leu Arg
1               5

<210> SEQ ID NO 270
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 270

Leu Arg Phe Cys Pro Phe Arg
1               5

<210> SEQ ID NO 271
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Leu Arg Phe Cys Pro Phe Ser
1               5

<210> SEQ ID NO 272
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Asp Cys Phe Phe Ser Phe Leu
1               5

<210> SEQ ID NO 273
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Phe Cys Pro Phe Arg Arg Arg
1               5

<210> SEQ ID NO 274
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Phe Cys Pro Phe Arg Arg Ser
1               5

<210> SEQ ID NO 275
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Ser Phe Cys Pro Phe Arg Arg
1               5

<210> SEQ ID NO 276
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 276

Tyr Tyr Leu Gln Leu Gln Cys
1               5

<210> SEQ ID NO 277
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Arg Arg Phe Cys Pro Phe Arg
1               5

<210> SEQ ID NO 278
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Arg Leu Arg Phe Cys Pro Phe
1               5

<210> SEQ ID NO 279
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Cys Phe Phe Ser Phe Leu Ala
1               5

<210> SEQ ID NO 280
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Lys Met Thr Lys Asp Cys Phe
1               5

<210> SEQ ID NO 281
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Arg Phe Cys Pro Phe Ser Arg
1               5
```

<210> SEQ ID NO 282
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Arg Ser Phe Cys Pro Phe Ser
1               5

<210> SEQ ID NO 283
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Arg Ser Phe Cys Pro Phe Arg
1               5

<210> SEQ ID NO 284
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Arg Phe Cys Pro Phe Arg Leu
1               5

<210> SEQ ID NO 285
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Phe Cys Pro Phe Arg Leu Arg
1               5

<210> SEQ ID NO 286
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Phe Cys Pro Phe Leu Arg Ser
1               5

<210> SEQ ID NO 287
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 287

Met Thr Lys Asp Cys Phe Phe
1               5

<210> SEQ ID NO 288
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Tyr Lys Met Thr Lys Asp Cys
1               5

<210> SEQ ID NO 289
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Leu Leu Arg Phe Cys Pro Phe
1               5

<210> SEQ ID NO 290
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Lys Asp Cys Phe Phe Ser Phe
1               5

<210> SEQ ID NO 291
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Ser Phe Cys Pro Phe Leu Arg
1               5

<210> SEQ ID NO 292
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Arg Phe Cys Pro Phe Arg Arg
1               5

<210> SEQ ID NO 293
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Arg Phe Cys Pro Phe Arg Ser
1               5

<210> SEQ ID NO 294
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Arg Arg Leu Phe Cys Pro Phe
1               5

<210> SEQ ID NO 295
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Ser Ser Phe Cys Pro Phe Arg
1               5

<210> SEQ ID NO 296
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Phe Cys Pro Phe Ser Arg Arg
1               5

<210> SEQ ID NO 297
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Arg Arg Ser Phe Cys Pro Phe
1               5

<210> SEQ ID NO 298
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Arg Arg Arg Phe Cys Pro Phe
```

```
1               5

<210> SEQ ID NO 299
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Arg Ser Arg Phe Cys Pro Phe
1               5

<210> SEQ ID NO 300
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Arg Phe Cys Pro Phe Leu Arg
1               5

<210> SEQ ID NO 301
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Phe Cys Pro Phe Arg Leu Arg
1               5

<210> SEQ ID NO 302
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Phe Cys Pro Phe Arg Arg Arg
1               5

<210> SEQ ID NO 303
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Phe Cys Pro Phe Arg Arg Ser
1               5

<210> SEQ ID NO 304
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 304

Ser Arg Ser Phe Cys Pro Phe
1               5

<210> SEQ ID NO 305
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Ser Phe Cys Pro Phe Arg Arg
1               5

<210> SEQ ID NO 306
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Ser Arg Arg Phe Cys Pro Phe
1               5

<210> SEQ ID NO 307
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Ser Arg Phe Cys Pro Phe Ser
1               5

<210> SEQ ID NO 308
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Ser Arg Phe Cys Pro Phe Arg
1               5

<210> SEQ ID NO 309
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Arg Ser Ser Phe Cys Pro Phe
1               5

<210> SEQ ID NO 310

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Arg Arg Phe Cys Pro Phe Arg
1               5

<210> SEQ ID NO 311
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Arg Arg Phe Cys Pro Phe Ser
1               5

<210> SEQ ID NO 312
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Arg Phe Cys Pro Phe Ser Ser
1               5

<210> SEQ ID NO 313
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Arg Thr Phe Cys Pro Phe Arg
1               5

<210> SEQ ID NO 314
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Arg Phe Cys Pro Phe Ser Arg
1               5

<210> SEQ ID NO 315
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315
```

```
Arg Leu Arg Phe Cys Pro Phe
1               5

<210> SEQ ID NO 316
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Arg Leu Phe Cys Pro Phe Arg
1               5

<210> SEQ ID NO 317
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Arg Ser Phe Cys Pro Phe Arg
1               5

<210> SEQ ID NO 318
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Leu Arg Phe Cys Pro Phe Arg
1               5

<210> SEQ ID NO 319
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Arg Arg Phe Cys Pro Phe Leu
1               5

<210> SEQ ID NO 320
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Ser Phe Cys Pro Phe Leu Arg
1               5

<210> SEQ ID NO 321
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 321

Arg Phe Cys Pro Phe Arg Arg
1               5

<210> SEQ ID NO 322
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Arg Phe Cys Pro Phe Arg Ser
1               5

<210> SEQ ID NO 323
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Arg Phe Cys Pro Phe Arg Thr
1               5

<210> SEQ ID NO 324
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Phe Cys Pro Phe Arg Ser Arg
1               5

<210> SEQ ID NO 325
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Gln Leu Cys Tyr
1

<210> SEQ ID NO 326
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Pro Met Ser Gly
1
```

```
<210> SEQ ID NO 327
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Tyr Pro Met Ser Gly
1               5

<210> SEQ ID NO 328
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Leu Tyr Pro Met Ser Gly
1               5

<210> SEQ ID NO 329
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Met Asn Gln Lys
1

<210> SEQ ID NO 330
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
tttttttttt tttttttttt ttttt                                              25

<210> SEQ ID NO 331
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(14)
<223> OTHER INFORMATION: Any amino acid
<220> FEATURE:
<221> NAME/KEY: MOD_RES
<222> LOCATION: (19)..(31)
<223> OTHER INFORMATION: Any amino acid

<400> SEQUENCE: 331

Met Xaa Xaa Xaa Xaa Xaa Xaa Xaa Xaa Xaa Xaa Xaa Xaa Xaa Phe Cys
1               5                   10                  15

Pro Phe Xaa Xaa Xaa Xaa Xaa Xaa Xaa Xaa Xaa Xaa Xaa Xaa Xaa Gly
            20                  25                  30
```

```
Ser Gly Ser Leu Gly His His His His His Arg Leu
        35                  40                  45

<210> SEQ ID NO 332
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Asp Cys Phe Phe
1
```